US012714436B2

(12) United States Patent
Center et al.

(10) Patent No.: US 12,714,436 B2
(45) **Date of Patent: *Aug. 25, 2026**

(54) DEVICES AND METHODS FOR OCCLUSION OF AN ATRIAL APPENDAGE

(71) Applicant: W. L. Gore & Associates, Inc., Newark, DE (US)

(72) Inventors: Charles J. Center, Flagstaff, AZ (US); Aaron D. Fox, Flagstaff, AZ (US); Nathan C. Korey, Flagstaff, AZ (US); Edward E. Shaw, Flagstaff, AZ (US); Nicholas S. Webster, Flagstaff, AZ (US); Brett J. Wham, Flagstaff, AZ (US); Roark N. Wolfe, Flagstaff, AZ (US); Peter J. Zeller, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 184 days.

This patent is subject to a terminal disclaimer.

(21) Appl. No.: 18/519,740

(22) Filed: Nov. 27, 2023

(65) Prior Publication Data

US 2024/0245407 A1 Jul. 25, 2024

Related U.S. Application Data

(63) Continuation of application No. 17/400,830, filed on Aug. 12, 2021, now Pat. No. 11,826,052, which is a (Continued)

(51) Int. Cl.
*A61B 17/12* (2006.01)
*A61B 17/00* (2006.01)

(52) U.S. Cl.
CPC .. *A61B 17/12172* (2013.01); *A61B 17/12031* (2013.01); *A61B 17/12122* (2013.01);
(Continued)

(58) Field of Classification Search
CPC ........ A61B 17/12031; A61B 17/12122; A61B 17/12172; A61B 17/12177;
(Continued)

(56) References Cited

U.S. PATENT DOCUMENTS

| | | | |
|---|---|---|---|
| 654,799 | A | 7/1900 | Levett |
| 1,851,314 | A | 3/1932 | Knoche |

(Continued)

FOREIGN PATENT DOCUMENTS

| | | | |
|---|---|---|---|
| CN | 1342056 A | 3/2002 |
| CN | 2820130 Y | 9/2006 |

(Continued)

OTHER PUBLICATIONS

European Search Report for European Application No. 16155556.0 mailed Aug. 1, 2016, 10 pages.

(Continued)

*Primary Examiner* — Mohamed G Gabr

(57) ABSTRACT

Various aspects of the present disclosure are directed toward apparatuses, methods, and systems as relating to occlusion. In certain instances, the apparatuses, methods, and systems may include a device for placement in vessels, appendages, and openings in a body. The device may include a unitary frame having a face portion that includes a center frame portion a plurality of elongate members.

20 Claims, 20 Drawing Sheets

Related U.S. Application Data continuation of application No. 15/154,695, filed on May 13, 2016, now Pat. No. 11,129,622.

(60) Provisional application No. 62/161,742, filed on May 14, 2015.

(52) U.S. Cl.
CPC .................. *A61B 17/12177* (2013.01); *A61B 2017/00575* (2013.01); *A61B 2017/00579* (2013.01); *A61B 2017/00592* (2013.01); *A61B 2017/00597* (2013.01); *A61B 2017/00632* (2013.01); *A61B 2017/00867* (2013.01); *A61B 2017/00986* (2013.01)

(58) Field of Classification Search
CPC ........... A61B 2017/00575; A61B 2017/00579; A61B 2017/00592; A61B 2017/00597; A61B 2017/00632; A61B 2017/00867; A61B 2017/00986
See application file for complete search history.

(56) References Cited

U.S. PATENT DOCUMENTS 3,625,451 A 12/1971 Anderson
3,915,167 A 10/1975 Waterman
3,953,566 A 4/1976 Gore
4,222,126 A 9/1980 Boretos et al.
4,265,694 A 5/1981 Boretos et al.
4,339,831 A 7/1982 Johnson
4,340,091 A 7/1982 Skelton et al.
4,349,498 A 9/1982 Ellis et al.
4,425,908 A 1/1984 Simon
4,626,255 A 12/1986 Reichart et al.
4,629,459 A 12/1986 Ionescu et al.
4,655,246 A 4/1987 Philipot et al.
4,692,369 A 9/1987 Nomi
4,731,074 A 3/1988 Rousseau et al.
4,851,000 A 7/1989 Gupta
4,858,810 A 8/1989 Intlekofer
4,877,661 A 10/1989 House et al.
4,955,899 A 9/1990 Della et al.
5,026,513 A 6/1991 House et al.
5,071,609 A 12/1991 Tu et al.
5,217,486 A 6/1993 Rice et al.
5,234,458 A 8/1993 Metais
5,325,746 A 7/1994 Anderson
5,344,427 A 9/1994 Cottenceau et al.
5,397,355 A 3/1995 Marin
5,476,589 A 12/1995 Bacino
5,491,704 A 2/1996 Duron
5,527,338 A 6/1996 Purdy
5,534,007 A 7/1996 St et al.
5,549,663 A 8/1996 Cottone, Jr.
5,554,183 A 9/1996 Nazari
5,562,726 A 10/1996 Chuter
5,693,083 A 12/1997 Baker et al.
5,707,376 A 1/1998 Kavteladze et al.
5,708,044 A 1/1998 Branca
5,709,704 A 1/1998 Nott et al.
5,713,917 A 2/1998 Leonhardt et al.
5,713,948 A 2/1998 Ulfacker
5,718,973 A 2/1998 Lewis et al.
5,720,776 A 2/1998 Chuter et al.
5,725,552 A 3/1998 Kotula
5,759,192 A 6/1998 Saunders
5,769,884 A 6/1998 Solovay
5,772,884 A 6/1998 Tanaka et al.
5,776,141 A 7/1998 Klein et al.
5,776,186 A 7/1998 Uflacker
5,782,909 A 7/1998 Quiachon et al.
5,824,043 A 10/1998 Cottone, Jr.
5,824,050 A 10/1998 Karwoski et al.
5,843,158 A 12/1998 Lenker et al.
5,843,161 A 12/1998 Solovay
5,843,162 A 12/1998 Inoue
5,904,703 A 5/1999 Gilson
5,935,162 A 8/1999 Dang
5,961,546 A 10/1999 Robinson et al.
6,010,529 A 1/2000 Herweck et al.
6,013,093 A 1/2000 Nott et al.
6,013,854 A 1/2000 Moriuchi
6,015,431 A 1/2000 Thornton et al.
6,019,785 A 2/2000 Strecker
6,027,779 A 2/2000 Campbell et al.
6,042,588 A 3/2000 Munsinger et al.
6,042,606 A 3/2000 Frantzen
6,143,021 A 11/2000 Staeghle
6,152,144 A 11/2000 Lesh
6,165,195 A 12/2000 Wilson
6,174,331 B1 1/2001 Moe et al.
6,190,406 B1 2/2001 Duerig et al.
6,214,025 B1 4/2001 Thistle et al.
6,231,561 B1 5/2001 Frazier et al.
6,231,581 B1 5/2001 Shank et al.
6,231,589 B1 5/2001 Wessman et al.
6,245,012 B1 6/2001 Kleshinski
6,245,939 B1 6/2001 Hsu et al.
6,261,320 B1 7/2001 Tam et al.
6,264,671 B1 7/2001 Stack
6,273,900 B1 8/2001 Nott et al.
6,283,994 B1 9/2001 Moe et al.
6,322,585 B1 11/2001 Khosravi et al.
6,328,727 B1 12/2001 Frazier et al.
6,346,117 B1 2/2002 Greenhalgh
6,352,561 B1 3/2002 Leopold et al.
6,372,870 B1 4/2002 Kitahara et al.
6,428,571 B1 8/2002 Lentz et al.
6,436,132 B1 8/2002 Patel et al.
6,451,051 B2 9/2002 Drasler et al.
6,451,396 B1 9/2002 Zumbrum et al.
6,461,665 B1 10/2002 Scholander
6,485,513 B1 11/2002 Fan
6,488,701 B1 12/2002 Nolting et al.
6,491,704 B2 12/2002 Gifford, III et al.
6,524,335 B1 2/2003 Hartley et al.
6,527,779 B1 3/2003 Rourke
6,541,589 B1 4/2003 Baillie
6,551,303 B1 4/2003 Van Tassel et al.
6,551,350 B1 4/2003 Thornton et al.
6,562,069 B2 5/2003 Cai et al.
6,572,643 B1 6/2003 Gharibadeh
6,572,646 B1 6/2003 Boylan et al.
6,620,190 B1 9/2003 Colone
6,626,939 B1 9/2003 Burnside et al.
6,652,556 B1 11/2003 Vantassel et al.
6,666,885 B2 12/2003 Moe
6,673,455 B2 1/2004 Zumbrum et al.
6,689,150 B1 2/2004 VanTassel
6,705,563 B2 3/2004 Luo et al.
6,712,836 B1 3/2004 Berg et al.
6,712,842 B1 3/2004 Gifford, III et al.
6,726,715 B2 4/2004 Sutherland
6,730,108 B2 5/2004 Van Tassel
6,730,120 B2 5/2004 Berg et al.
6,743,210 B2 6/2004 Hart et al.
6,746,472 B2 6/2004 Frazier et al.
6,755,854 B2 6/2004 Gillick et al.
6,755,856 B2 6/2004 Fierens et al.
6,755,857 B2 6/2004 Peterson et al.
6,758,858 B2 7/2004 Mccrea et al.
6,770,579 B1 8/2004 Dawson et al.
6,776,604 B1 8/2004 Chobotov et al.
6,827,731 B2 12/2004 Armstrong et al.
6,866,669 B2 3/2005 Buzzard et al.
6,884,259 B2 4/2005 Tran et al.
6,926,732 B2 8/2005 Derus et al.
6,939,352 B2 9/2005 Buzzard et al.
6,945,990 B2 9/2005 Greenan
6,949,113 B2 9/2005 Van Tassel
6,953,332 B1 10/2005 Kurk et al.
6,974,471 B2 12/2005 Shie et al.

(56) References Cited

U.S. PATENT DOCUMENTS

| | | | |
|---|---|---|---|
| 6,994,092 | B2 | 2/2006 | Van Der Burg et al. |
| 7,033,368 | B2 | 4/2006 | Rourke |
| 7,044,134 | B2 | 5/2006 | Khairkhahan |
| 7,049,380 | B1 | 5/2006 | Chang |
| 7,052,511 | B2 | 5/2006 | Weldon et al. |
| 7,066,951 | B2 | 6/2006 | Chovotov |
| 7,083,642 | B2 | 8/2006 | Sirhan et al. |
| 7,105,018 | B1 | 9/2006 | Yip et al. |
| 7,122,050 | B2 | 10/2006 | Randall et al. |
| 7,128,073 | B1 | 10/2006 | Van Der Burg et al. |
| 7,147,657 | B2 | 12/2006 | Chiang et al. |
| 7,169,160 | B1 | 1/2007 | Middleman et al. |
| 7,198,636 | B2 | 4/2007 | Cully et al. |
| 7,208,003 | B2 | 4/2007 | Davis et al. |
| 7,238,200 | B2 | 7/2007 | Lee et al. |
| 7,252,680 | B2 | 8/2007 | Freitag |
| 7,306,729 | B2 | 12/2007 | Bacino et al. |
| 7,331,992 | B2 | 2/2008 | Randall et al. |
| 7,396,359 | B1 | 7/2008 | DeRowe |
| 7,419,678 | B2 | 9/2008 | Falotico |
| 7,448,122 | B1 | 11/2008 | Kokish et al. |
| 7,462,675 | B2 | 12/2008 | Chang et al. |
| 7,531,611 | B2 | 5/2009 | Sabol et al. |
| 7,555,034 | B2 | 6/2009 | Shin et al. |
| 7,566,336 | B2 | 7/2009 | Corcoran et al. |
| 7,572,289 | B2 | 8/2009 | Sisken et al. |
| 7,601,159 | B2 | 10/2009 | Ewers et al. |
| 7,611,528 | B2 | 11/2009 | Goodson et al. |
| 7,628,803 | B2 | 12/2009 | Pavcnik et al. |
| 7,655,034 | B2 | 2/2010 | Mitchell et al. |
| 7,678,123 | B2 | 3/2010 | Chanduszko |
| 7,771,455 | B2 | 8/2010 | Ken |
| 7,789,908 | B2 | 9/2010 | Sowinski et al. |
| 7,803,186 | B1 | 9/2010 | Li et al. |
| 7,811,314 | B2 | 10/2010 | Fierens et al. |
| 7,815,591 | B2 | 10/2010 | Levine et al. |
| 7,815,763 | B2 | 10/2010 | Fierens et al. |
| 7,833,565 | B2 | 11/2010 | O'Connor et al. |
| 7,846,179 | B2 | 12/2010 | Belef et al. |
| 7,887,580 | B2 | 2/2011 | Randall et al. |
| 7,927,364 | B2 | 4/2011 | Fierens et al. |
| 7,927,365 | B2 | 4/2011 | Fierens et al. |
| 7,935,141 | B2 | 5/2011 | Randall et al. |
| 7,967,829 | B2 | 6/2011 | Gunderson et al. |
| 7,976,575 | B2 | 7/2011 | Hartley |
| 7,998,189 | B2 | 8/2011 | Kolbel et al. |
| 8,029,557 | B2 | 10/2011 | Sobrino-Serrano et al. |
| 8,029,559 | B2 | 10/2011 | Sisken et al. |
| 8,029,563 | B2 | 10/2011 | House et al. |
| 8,048,440 | B2 | 11/2011 | Chang |
| 8,062,349 | B2 | 11/2011 | Moore et al. |
| 8,080,032 | B2 | 12/2011 | van der Burg |
| 8,157,810 | B2 | 4/2012 | Case et al. |
| 8,167,935 | B2 | 5/2012 | Mcguckin et al. |
| 8,231,650 | B2 | 7/2012 | Cully |
| 8,241,350 | B2 | 8/2012 | Randall et al. |
| 8,273,105 | B2 | 9/2012 | Cohen et al. |
| 8,287,583 | B2 | 10/2012 | LaDuca et al. |
| 8,349,000 | B2 | 1/2013 | Schreck |
| 8,424,166 | B2 | 4/2013 | Dorneman et al. |
| 8,449,595 | B2 | 5/2013 | Ouellette et al. |
| 8,469,990 | B2 | 6/2013 | McGuckin |
| 8,475,512 | B2 | 7/2013 | Hunt |
| 8,523,897 | B2 | 9/2013 | van der Burg |
| 8,529,597 | B2 | 9/2013 | Linder |
| 8,585,757 | B2 | 11/2013 | Agathos |
| 8,637,144 | B2 | 1/2014 | Ford |
| 8,685,055 | B2 | 4/2014 | Van Tassel |
| 8,709,077 | B2 | 4/2014 | Schreck |
| 8,801,746 | B1 | 8/2014 | Kreidler |
| 8,834,519 | B2 | 9/2014 | van der Burg |
| 8,870,947 | B2 | 10/2014 | Shaw |
| 8,945,212 | B2 | 2/2015 | Bruchman et al. |
| 8,961,599 | B2 | 2/2015 | Bruchman et al. |
| 9,109,310 | B2 | 8/2015 | Baaijens et al. |
| 9,254,204 | B2 | 2/2016 | Roeder |
| 9,314,249 | B2 | 4/2016 | Kreidler |
| 9,399,085 | B2 | 7/2016 | Cleek et al. |
| 9,504,565 | B2 | 11/2016 | Armstrong |
| 9,554,806 | B2 | 1/2017 | Larsen et al. |
| 9,554,900 | B2 | 1/2017 | Bruchman et al. |
| 9,597,086 | B2 | 3/2017 | Larsen et al. |
| 9,743,932 | B2 | 8/2017 | Amplatz |
| 9,744,033 | B2 | 8/2017 | Bruchman et al. |
| 9,770,327 | B2 | 9/2017 | Bruchman et al. |
| 9,795,475 | B2 | 10/2017 | Bruchman et al. |
| 9,801,712 | B2 | 10/2017 | Bruchman et al. |
| 10,022,219 | B2 | 7/2018 | Bruchman et al. |
| 10,342,658 | B2 | 7/2019 | Bruchman et al. |
| 10,470,878 | B2 | 11/2019 | Bruchman et al. |
| 11,129,622 | B2 * | 9/2021 | Center ............ A61B 17/12122 |
| 2001/0037142 | A1 | 11/2001 | Stelter et al. |
| 2001/0051824 | A1 | 12/2001 | Hopkins et al. |
| 2002/0007208 | A1 | 1/2002 | Strecker et al. |
| 2002/0022860 | A1 | 2/2002 | Borillo et al. |
| 2002/0029077 | A1 | 3/2002 | Leopold et al. |
| 2002/0045936 | A1 | 4/2002 | Moe |
| 2002/0055773 | A1 | 5/2002 | Campbell et al. |
| 2002/0099431 | A1 | 7/2002 | Armstrong et al. |
| 2002/0151953 | A1 | 10/2002 | Chobotov et al. |
| 2002/0198588 | A1 | 12/2002 | Armstrong et al. |
| 2002/0198594 | A1 | 12/2002 | Schreck |
| 2003/0004559 | A1 | 1/2003 | Lentz et al. |
| 2003/0004560 | A1 | 1/2003 | Chobotov et al. |
| 2003/0012905 | A1 | 1/2003 | Zumbrum et al. |
| 2003/0023303 | A1 | 1/2003 | Palmaz et al. |
| 2003/0040771 | A1 | 2/2003 | Hyodoh et al. |
| 2003/0055492 | A1 | 3/2003 | Shaolian et al. |
| 2003/0055495 | A1 | 3/2003 | Pease et al. |
| 2003/0055496 | A1 | 3/2003 | Cai et al. |
| 2003/0057156 | A1 | 3/2003 | Peterson et al. |
| 2003/0060871 | A1 | 3/2003 | Hill et al. |
| 2003/0097175 | A1 | 5/2003 | O'Connor et al. |
| 2003/0098383 | A1 | 5/2003 | Luo et al. |
| 2003/0114917 | A1 | 6/2003 | Holloway et al. |
| 2003/0120337 | A1 | 6/2003 | Van et al. |
| 2003/0139806 | A1 | 7/2003 | Haverkost et al. |
| 2003/0149467 | A1 | 8/2003 | Linder et al. |
| 2003/0181942 | A1 | 9/2003 | Sutton |
| 2003/0211264 | A1 | 11/2003 | Farnsworth et al. |
| 2003/0229394 | A1 | 12/2003 | Ogle et al. |
| 2004/0019374 | A1 | 1/2004 | Hojeibane et al. |
| 2004/0024442 | A1 | 2/2004 | Sowinski et al. |
| 2004/0024448 | A1 | 2/2004 | Chang et al. |
| 2004/0034366 | A1 | 2/2004 | Van der Burg et al. |
| 2004/0044361 | A1 | 3/2004 | Frazier et al. |
| 2004/0054396 | A1 | 3/2004 | Hartley |
| 2004/0073289 | A1 | 4/2004 | Hartley |
| 2004/0093070 | A1 | 5/2004 | Hojeibane et al. |
| 2004/0122503 | A1 | 6/2004 | Campbell et al. |
| 2004/0138734 | A1 | 7/2004 | Chobotov et al. |
| 2004/0143315 | A1 | 7/2004 | Bruun et al. |
| 2004/0167619 | A1 | 8/2004 | Case et al. |
| 2004/0176839 | A1 | 9/2004 | Huynh et al. |
| 2004/0260393 | A1 | 12/2004 | Rahdert et al. |
| 2005/0038470 | A1 | 2/2005 | Van der Burg et al. |
| 2005/0049667 | A1 | 3/2005 | Arbefeuille et al. |
| 2005/0070820 | A1 | 3/2005 | Boutillette |
| 2005/0080476 | A1 | 4/2005 | Gunderson et al. |
| 2005/0085890 | A1 | 4/2005 | Rasmussen |
| 2005/0113861 | A1 | 5/2005 | Corcoran |
| 2005/0125031 | A1 | 6/2005 | Pipenhagen et al. |
| 2005/0137682 | A1 | 6/2005 | Justino |
| 2005/0240257 | A1 | 10/2005 | Ishimaru et al. |
| 2005/0261765 | A1 | 11/2005 | Liddicoat |
| 2005/0283224 | A1 | 12/2005 | King |
| 2005/0288767 | A1 | 12/2005 | Kujawski et al. |
| 2006/0004433 | A1 | 1/2006 | Greenberg et al. |
| 2006/0015171 | A1 | 1/2006 | Armstrong |
| 2006/0036311 | A1 | 2/2006 | Nakayama et al. |
| 2006/0058833 | A1 | 3/2006 | Vancamp |
| 2006/0058889 | A1 | 3/2006 | Case et al. |
| 2006/0135947 | A1 | 6/2006 | Soltesz et al. |
| 2006/0155366 | A1 | 7/2006 | LaDuca et al. |

(56) References Cited

U.S. PATENT DOCUMENTS

2006/0190074 A1 8/2006 Hill et al.
2006/0254569 A1 11/2006 Chipman
2006/0259133 A1 11/2006 Sowinski et al.
2006/0264980 A1 11/2006 Khairkhahan
2006/0265053 A1 11/2006 Hunt
2006/0276883 A1 12/2006 Greenberg et al.
2006/0276888 A1 12/2006 Lee et al.
2006/0290027 A1 12/2006 O'Connor et al.
2007/0012624 A1 1/2007 Bacino et al.
2007/0027528 A1 2/2007 Agnew
2007/0027535 A1 2/2007 Purdy et al.
2007/0060999 A1 3/2007 Randall et al.
2007/0066993 A1 3/2007 Kreidler
2007/0067021 A1 3/2007 Haverkost et al.
2007/0088424 A1 4/2007 Greenberg
2007/0100427 A1 5/2007 Perouse
2007/0118209 A1 5/2007 Strecker
2007/0118210 A1 5/2007 Pinchuk
2007/0129786 A1 6/2007 Beach et al.
2007/0162048 A1 7/2007 Quinn et al.
2007/0167955 A1 7/2007 Arnault de la Menardiere et al.
2007/0198077 A1 8/2007 Cully et al.
2007/0198078 A1 8/2007 Berra et al.
2007/0208421 A1 9/2007 Quigley
2007/0213800 A1 9/2007 Fierens et al.
2007/0219467 A1 9/2007 Clark
2007/0248640 A1 10/2007 Karabey et al.
2007/0249980 A1 10/2007 Carrez et al.
2007/0250146 A1 10/2007 Cully et al.
2007/0250153 A1 10/2007 Cully et al.
2007/0254012 A1 11/2007 Ludwig et al.
2007/0255390 A1 11/2007 Ducke et al.
2007/0270891 A1 11/2007 McGuckin
2007/0288087 A1 12/2007 Fearnot et al.
2008/0027529 A1 1/2008 Hartley et al.
2008/0033527 A1 2/2008 Nunez et al.
2008/0033534 A1 2/2008 Cook
2008/0039925 A1 2/2008 Ishimaru et al.
2008/0051876 A1 2/2008 Ta et al.
2008/0091261 A1 4/2008 Long et al.
2008/0114440 A1 5/2008 Hlavka et al.
2008/0119943 A1 5/2008 Armstrong et al.
2008/0125711 A1 5/2008 Alpini et al.
2008/0133004 A1 6/2008 White
2008/0147111 A1 6/2008 Johnson
2008/0178434 A1 7/2008 Bulanda
2008/0200977 A1 8/2008 Paul et al.
2008/0208329 A1 8/2008 Bishop
2008/0269785 A1 10/2008 Lampropoulos
2008/0319531 A1 12/2008 Doran et al.
2009/0004239 A1 1/2009 Ladet et al.
2009/0005854 A1 1/2009 Huang et al.
2009/0030499 A1 1/2009 Bebb et al.
2009/0036976 A1 2/2009 Beach et al.
2009/0043373 A1 2/2009 Arnault et al.
2009/0048656 A1 2/2009 Wen
2009/0054723 A1 2/2009 Khairkhahan et al.
2009/0062838 A1 3/2009 Brumleve et al.
2009/0082844 A1 3/2009 Zacharias et al.
2009/0099596 A1 4/2009 McGuckin, Jr
2009/0099640 A1 4/2009 Weng
2009/0112249 A1 4/2009 Miles
2009/0117334 A1 5/2009 Sogard et al.
2009/0157175 A1 6/2009 Benichou
2009/0171386 A1 7/2009 Amplatz
2009/0182413 A1 7/2009 Burkart et al.
2009/0187197 A1 7/2009 Roeber et al.
2009/0216308 A1 8/2009 Hartley
2009/0216321 A1 8/2009 Osborne et al.
2009/0259291 A1 10/2009 Kolbel et al.
2010/0011564 A1 1/2010 Millwee et al.
2010/0016943 A1 1/2010 Chobotov
2010/0023048 A1 1/2010 Mach
2010/0023114 A1 1/2010 Chambers et al.
2010/0057195 A1 3/2010 Roeder et al.
2010/0094394 A1 4/2010 Beach et al.
2010/0094401 A1 4/2010 Kolbel
2010/0094405 A1 4/2010 Cottone
2010/0106240 A1 4/2010 Duggal et al.
2010/0159171 A1 6/2010 Clough
2010/0190254 A1 7/2010 Chian et al.
2010/0211052 A1 8/2010 Brown et al.
2010/0248324 A1 9/2010 Xu et al.
2010/0249922 A1 9/2010 Li et al.
2010/0280591 A1 11/2010 Shin
2010/0298931 A1 11/2010 Quadri et al.
2011/0039690 A1 2/2011 Niu
2011/0040366 A1 2/2011 Goetz et al.
2011/0049757 A1 3/2011 O'Connor et al.
2011/0054515 A1* 3/2011 Bridgeman ...... A61B 17/12122 606/200
2011/0054519 A1 3/2011 Neuss
2011/0064781 A1 3/2011 Cleek et al.
2011/0066221 A1 3/2011 White et al.
2011/0125252 A1 5/2011 Goddard
2011/0130821 A1 6/2011 Perouse
2011/0142804 A1 6/2011 Gaudette et al.
2011/0218619 A1 9/2011 Benichou et al.
2011/0250689 A1 10/2011 Baaijens et al.
2011/0311746 A1 12/2011 Ma et al.
2011/0313503 A1 12/2011 Berra et al.
2012/0022630 A1 1/2012 Wubbeling
2012/0022638 A1 1/2012 Leewood et al.
2012/0046652 A1 2/2012 Sokel
2012/0058100 A1 3/2012 Shastri et al.
2012/0061314 A1 3/2012 Choi et al.
2012/0065667 A1 3/2012 Javois et al.
2012/0078357 A1 3/2012 Conklin
2012/0116496 A1 5/2012 Chuter et al.
2012/0123529 A1 5/2012 Levi et al.
2012/0123530 A1 5/2012 Carpentier et al.
2012/0129150 A1 5/2012 Carbonell
2012/0130473 A1 5/2012 Norris et al.
2012/0130474 A1 5/2012 Buckley
2012/0130475 A1 5/2012 Shaw
2012/0143242 A1 6/2012 Masters
2012/0143305 A1 6/2012 Berra et al.
2012/0172927 A1 7/2012 Cambell et al.
2012/0172965 A1 7/2012 Kratzberg et al.
2012/0172968 A1 7/2012 Chuter et al.
2012/0253450 A1 10/2012 Case et al.
2012/0253453 A1 10/2012 Bruchman et al.
2012/0283585 A1 11/2012 Werneth et al.
2012/0283773 A1 11/2012 Van Tassel
2012/0290082 A1 11/2012 Quint et al.
2012/0296160 A1 11/2012 Hill et al.
2012/0296360 A1 11/2012 Norris et al.
2012/0296418 A1 11/2012 Bonyuet et al.
2012/0323211 A1 12/2012 Ogle et al.
2012/0323270 A1 12/2012 Lee
2012/0323315 A1 12/2012 Bruchman et al.
2013/0023981 A1 1/2013 Dierking et al.
2013/0046371 A1 2/2013 Greenberg et al.
2013/0073029 A1 3/2013 Shaw
2013/0103074 A1 4/2013 Riina et al.
2013/0123896 A1 5/2013 Bloss et al.
2013/0123908 A1 5/2013 Hinchliffe et al.
2013/0138138 A1 5/2013 Clark
2013/0150947 A1 6/2013 Kaufmann et al.
2013/0158647 A1 6/2013 Norris et al.
2013/0166021 A1 6/2013 Bruchman et al.
2013/0178889 A1 7/2013 Miles
2013/0184807 A1 7/2013 Kovach et al.
2013/0184808 A1 7/2013 Hall et al.
2013/0197631 A1 8/2013 Bruchman et al.
2013/0218192 A1 8/2013 Erzberger et al.
2013/0245666 A1 9/2013 Larsen et al.
2013/0245742 A1 9/2013 Norris
2013/0296912 A1 11/2013 Ottma
2013/0310924 A1 11/2013 Groothuis et al.
2013/0331929 A1 12/2013 Mitra et al.
2014/0005773 A1 1/2014 Wheatley
2014/0012303 A1 1/2014 Heipl
2014/0018841 A1 1/2014 Peiffer

(56) References Cited

U.S. PATENT DOCUMENTS

| | | | | |
|---|---|---|---|---|
| 2014/0031927 | A1 | 1/2014 | Bruchman et al. | |
| 2014/0046360 | A1 | 2/2014 | van der Burg | |
| 2014/0135817 | A1 | 5/2014 | Tischler | |
| 2014/0135897 | A1 | 5/2014 | Cully et al. | |
| 2014/0142617 | A1 | 5/2014 | Larsen | |
| 2014/0163671 | A1 | 6/2014 | Bruchman et al. | |
| 2014/0163673 | A1 | 6/2014 | Bruchman et al. | |
| 2014/0172066 | A1 | 6/2014 | Goepfrich et al. | |
| 2014/0172080 | A1 | 6/2014 | Bruchman et al. | |
| 2014/0172081 | A1 | 6/2014 | Bruchman et al. | |
| 2014/0172082 | A1 | 6/2014 | Bruchman et al. | |
| 2014/0172083 | A1 | 6/2014 | Bruchman et al. | |
| 2014/0180400 | A1 | 6/2014 | Bruchman et al. | |
| 2014/0180402 | A1 | 6/2014 | Bruchman et al. | |
| 2014/0188220 | A1 | 7/2014 | Seguin | |
| 2014/0228878 | A1 | 8/2014 | Scandurra et al. | |
| 2014/0253453 | A1 | 9/2014 | Lo | |
| 2014/0288642 | A1 | 9/2014 | Yoshida et al. | |
| 2014/0296908 | A1 | 10/2014 | Ottma | |
| 2014/0296909 | A1 | 10/2014 | Heipl | |
| 2014/0350592 | A1 | 11/2014 | Kreidler | |
| 2014/0371786 | A1 | 12/2014 | Kornblau et al. | |
| 2014/0379019 | A1 | 12/2014 | Larsen | |
| 2014/0379020 | A1 | 12/2014 | Campbell et al. | |
| 2015/0005809 | A1 | 1/2015 | Ayres et al. | |
| 2015/0005810 | A1 | 1/2015 | Center | |
| 2015/0039017 | A1 | 2/2015 | Cragg et al. | |
| 2015/0051695 | A1 | 2/2015 | Shaw | |
| 2015/0135537 | A1 | 5/2015 | Bruchman et al. | |
| 2015/0196300 | A1 | 7/2015 | Tischler et al. | |
| 2015/0223757 | A1* | 8/2015 | Werneth ............... | A61B 5/0205 600/301 |
| 2015/0224231 | A1 | 8/2015 | Bruchman et al. | |
| 2015/0257875 | A1 | 9/2015 | Bruchman et al. | |
| 2015/0257876 | A1 | 9/2015 | Bruchman et al. | |
| 2015/0257882 | A1 | 9/2015 | Bortlein et al. | |
| 2015/0265744 | A1 | 9/2015 | Baaijens | |
| 2015/0283297 | A1 | 10/2015 | Baaijens et al. | |
| 2015/0305749 | A1 | 10/2015 | Alferness | |
| 2015/0305862 | A1 | 10/2015 | Bruchman et al. | |
| 2015/0306277 | A1 | 10/2015 | Pathak et al. | |
| 2015/0351904 | A1 | 12/2015 | Cooper et al. | |
| 2015/0366663 | A1 | 12/2015 | Bruchman et al. | |
| 2016/0008133 | A9 | 1/2016 | Day et al. | |
| 2016/0067374 | A1 | 3/2016 | Puckett et al. | |
| 2016/0074161 | A1 | 3/2016 | Bennett | |
| 2016/0100939 | A1 | 4/2016 | Armstrong et al. | |
| 2016/0175095 | A1 | 6/2016 | Dienno et al. | |
| 2016/0175096 | A1 | 6/2016 | Dienno et al. | |
| 2016/0317299 | A1 | 11/2016 | Alkhatib | |
| 2016/0317301 | A1 | 11/2016 | Quadri et al. | |
| 2016/0331382 | A1 | 11/2016 | Center | |
| 2017/0042674 | A1 | 2/2017 | Armstrong | |
| 2017/0079768 | A1 | 3/2017 | Chanduszko et al. | |
| 2017/0156898 | A1 | 6/2017 | Obradovic | |
| 2017/0181751 | A1 | 6/2017 | Larsen | |
| 2017/0319338 | A1 | 11/2017 | Bruchman et al. | |
| 2018/0008406 | A1 | 1/2018 | Bruchman et al. | |
| 2018/0116678 | A1 | 5/2018 | Melanson et al. | |
| 2018/0193027 | A1 | 7/2018 | Wang et al. | |
| 2018/0200050 | A1 | 7/2018 | Bruchman et al. | |
| 2018/0206850 | A1 | 7/2018 | Wang et al. | |
| 2019/0110880 | A1 | 4/2019 | Fox et al. | |
| 2019/0114303 | A1 | 4/2019 | Peloski | |
| 2019/0247053 | A1 | 8/2019 | Inouye | |
| 2019/0258641 | A1 | 8/2019 | Peloski | |
| 2019/0269506 | A1 | 9/2019 | Bruchman et al. | |
| 2019/0274668 | A1 | 9/2019 | Glimsdale et al. | |
| 2021/0038230 | A1 | 2/2021 | Larsen et al. | |
| 2021/0228351 | A1 | 7/2021 | Bruchman et al. | |
| 2022/0031442 | A1 | 2/2022 | Fox et al. | |
| 2022/0125567 | A1 | 4/2022 | Center et al. | |
| 2022/0401105 | A1 | 12/2022 | Inc | |
| 2024/0041467 | A1 | 2/2024 | Larsen et al. | |
| 2024/0390129 | A1 | 11/2024 | Center et al. | |

FOREIGN PATENT DOCUMENTS

| | | | |
|---|---|---|---|
| CN | 2904980 | Y | 5/2007 |
| CN | 101304693 | A | 11/2008 |
| CN | 101554343 | A | 10/2009 |
| CN | 101780306 | A | 7/2010 |
| CN | 101965161 | | 2/2011 |
| CN | 201879866 | U | 6/2011 |
| CN | 201930098 | U | 8/2011 |
| CN | 202335893 | U | 7/2012 |
| CN | 102908174 | A | 2/2013 |
| CN | 103347467 | A | 10/2013 |
| CN | 103917169 | A | 7/2014 |
| CN | 104958087 | A | 10/2015 |
| CN | 105054985 | A | 11/2015 |
| CN | 106163425 | A | 11/2016 |
| CN | 106333725 | A | 1/2017 |
| CN | 107205743 | A | 9/2017 |
| DE | 102014102725 | A1 | 9/2015 |
| EP | 0150608 | A1 | 8/1985 |
| EP | 0293090 | A2 | 11/1988 |
| EP | 0313263 | A2 | 4/1989 |
| EP | 0664107 | A1 | 7/1995 |
| EP | 0679372 | A2 | 11/1995 |
| EP | 0773971 | A1 | 5/1997 |
| EP | 0815806 | A2 | 1/1998 |
| EP | 0893108 | A2 | 1/1999 |
| EP | 1318775 | A1 | 6/2003 |
| EP | 1977719 | A2 | 10/2008 |
| EP | 2074953 | A1 | 7/2009 |
| EP | 2481381 | | 8/2012 |
| EP | 2596754 | A1 | 5/2013 |
| FR | 2896405 | A1 | 7/2007 |
| GB | 2344054 | A | 5/2000 |
| JP | 02-000645 | A | 1/1990 |
| JP | 1996126704 | | 5/1996 |
| JP | 09-501759 | A | 2/1997 |
| JP | 09-241412 | A | 9/1997 |
| JP | 2001506902 | A | 7/1998 |
| JP | 11-290448 | A | 10/1999 |
| JP | 2002503114 | A | 1/2002 |
| JP | 2002518086 | A | 6/2002 |
| JP | 2003-512129 | A | 4/2003 |
| JP | 2004-506469 | A | 3/2004 |
| JP | 2004-510471 | A | 4/2004 |
| JP | 2004167239 | A | 6/2004 |
| JP | 2004188219 | A | 7/2004 |
| JP | 2005-505320 | A | 2/2005 |
| JP | 2005-530549 | A | 10/2005 |
| JP | 2007502689 | A1 | 2/2007 |
| JP | 2007518465 | A | 7/2007 |
| JP | 2008-506459 | A | 3/2008 |
| JP | 2008-531117 | A | 8/2008 |
| JP | 2009-542421 | A | 12/2009 |
| JP | 2010527742 | A | 8/2010 |
| JP | 2010-535075 | A | 11/2010 |
| JP | 2011-005292 | A | 1/2011 |
| JP | 2011509117 | A | 3/2011 |
| JP | 2011511693 | A | 4/2011 |
| JP | 2011516202 | | 5/2011 |
| JP | 2012-523894 | A | 10/2012 |
| JP | 2013-545515 | A | 12/2013 |
| JP | 2014501563 | A | 1/2014 |
| JP | 2014501565 | A | 1/2014 |
| JP | 2014502180 | A | 1/2014 |
| JP | 2014-531249 | A | 11/2014 |
| JP | 2014-533970 | A | 12/2014 |
| JP | 2014533189 | A | 12/2014 |
| JP | 2015-534881 | A | 12/2015 |
| JP | 7299216 | B2 | 6/2023 |
| JP | 7410206 | B2 | 1/2024 |
| RU | 2124986 | C1 | 1/1999 |
| WO | 95/05555 | A1 | 2/1995 |
| WO | 95/28899 | A1 | 11/1995 |
| WO | 1996018361 | A1 | 6/1996 |
| WO | 97/10871 | A1 | 3/1997 |
| WO | 1997048350 | A1 | 12/1997 |
| WO | 98/26731 | A2 | 6/1998 |
| WO | 1999065420 | A1 | 12/1999 |

(56) References Cited

FOREIGN PATENT DOCUMENTS

| | | | |
|---|---|---|---|
| WO | 2000013613 | A1 | 3/2000 |
| WO | 00/41649 | A1 | 7/2000 |
| WO | 00/62716 | A1 | 10/2000 |
| WO | 2001021109 | A1 | 3/2001 |
| WO | 01/30266 | A1 | 5/2001 |
| WO | 01/74272 | A2 | 10/2001 |
| WO | 02/15793 | A2 | 2/2002 |
| WO | 02/24118 | A1 | 3/2002 |
| WO | 02/24119 | A1 | 3/2002 |
| WO | 2002028317 | A2 | 4/2002 |
| WO | 02/60506 | A1 | 8/2002 |
| WO | 2002/100454 | A1 | 12/2002 |
| WO | 03/47468 | A1 | 6/2003 |
| WO | 2004/000375 | A1 | 12/2003 |
| WO | 2007092354 | A2 | 8/2004 |
| WO | 2008063464 | A2 | 5/2005 |
| WO | 2005072652 | | 8/2005 |
| WO | 2006/000763 | A2 | 1/2006 |
| WO | 2006007389 | A1 | 1/2006 |
| WO | 2006/019626 | A2 | 2/2006 |
| WO | 2006/091382 | A1 | 8/2006 |
| WO | 2006/127756 | A2 | 11/2006 |
| WO | 2007/002320 | A1 | 1/2007 |
| WO | 2007/016251 | A2 | 2/2007 |
| WO | 2008/006003 | A2 | 1/2008 |
| WO | 2008/028964 | A2 | 3/2008 |
| WO | 2008/036870 | A2 | 3/2008 |
| WO | 2008/049045 | A2 | 4/2008 |
| WO | 2008047092 | A1 | 4/2008 |
| WO | 2009/017827 | A1 | 2/2009 |
| WO | 2009/038761 | A1 | 3/2009 |
| WO | 2009/045332 | A2 | 4/2009 |
| WO | 2009088905 | | 7/2009 |
| WO | 2009/100210 | A1 | 8/2009 |
| WO | 2009102441 | A1 | 8/2009 |
| WO | 2009126227 | A2 | 10/2009 |
| WO | 2009/149462 | A2 | 12/2009 |
| WO | 2009148594 | A1 | 12/2009 |
| WO | 2010/006783 | A1 | 1/2010 |
| WO | 2010001012 | A1 | 1/2010 |
| WO | 2010/030766 | A1 | 3/2010 |
| WO | 2010024881 | | 3/2010 |
| WO | 2010041038 | A1 | 4/2010 |
| WO | 2010044854 | A1 | 4/2010 |
| WO | 2010063795 | A1 | 6/2010 |
| WO | 2010081041 | | 7/2010 |
| WO | 2010090699 | A1 | 8/2010 |
| WO | 2010105195 | A2 | 9/2010 |
| WO | 2010/132707 | A1 | 11/2010 |
| WO | 2011031981 | | 3/2011 |
| WO | 2011062858 | A1 | 5/2011 |
| WO | 2011/065809 | A2 | 6/2011 |
| WO | 2012068257 | A2 | 5/2012 |
| WO | 2012/109297 | A2 | 8/2012 |
| WO | 2012/135603 | A2 | 10/2012 |
| WO | 2012/163257 | A1 | 12/2012 |
| WO | 2012/167131 | A1 | 12/2012 |
| WO | 2013040431 | A1 | 3/2013 |
| WO | 2013137977 | A1 | 9/2013 |
| WO | 2014/036439 | A2 | 3/2014 |
| WO | 2014/078078 | A1 | 5/2014 |
| WO | 2014/078531 | A1 | 5/2014 |
| WO | 2014/210263 | A1 | 12/2014 |
| WO | 2015/085138 | A1 | 6/2015 |
| WO | 2015132668 | A1 | 9/2015 |
| WO | 2016/028591 | A1 | 2/2016 |
| WO | 2016/044223 | A1 | 3/2016 |
| WO | 2016/183495 | A2 | 11/2016 |
| WO | 2017/148102 | A1 | 9/2017 |
| WO | 2019/079262 | A1 | 4/2019 |

OTHER PUBLICATIONS

European Search Report from EP17166472.5, mailed Nov. 7, 2017, 7 pages.

International Preliminary Report on Patentability for PCT/US2012/055537, issued Mar. 18, 2014, 10 pages.

International Preliminary Report on Patentability for PCT/U.S. Pat. No. 2012055445 issued Mar. 18, 2014, 9 pages.

International Search Report & Written Opinion in International Application No. PCT/US/2012/055445, mailed Dec. 5, 2012, 15 pages.

International Search Report and Written Opinion for PCT/US2012/055537, mailed Dec. 5, 2012, 5 pages.

International Search Report and Written Opinion for PCT/US2012/061928 mailed Jan. 22, 2013, corresponding to U.S. Appl. No. 13/658,597, 8 pages.

International Search Report and Written Opinion for PCT/US2013/022404 mailed May 8, 2013, corresponding to USSN 13/743, 118, 7 pages.

International Search Report and Written Opinion for PCT/US2014/066153 mailed Feb. 17, 2015, corresponding to U.S. Appl. No. 14/084,592, 5 pages.

International Search Report and Written Opinion from PCT/US2016/032487, mailed Dec. 14, 2016, 20 pages.

Search Report and Written Opinion from PCT/US2018/056031, mailed Feb. 1, 2019, 18.

Ueda et al, Incomplete Endograft Apposition to the Aortic Arch: Bird-Beak Configuration Increases Risk of Endoleak Formation after Thoracic Endovascular Aortic Repair, Radiology: vol. 255" No. 2; May 2010, pp. 645-652.

European Search Report for EP Patent Application No. 24191022.3, Issued on Oct. 16, 2024, 10 pages.

International Preliminary Report on Patentability received for PCT Patent Application No. PCT/US2016/032487, mailed on Nov. 23, 2017, 13 pages.

Nakayama, Yasuhide. Microporous Stent Achieves Brain Aneurysm Occlusion Without Disturbing Branching Flow. NeuroNews Nov. 2012; 8:1-2.

Nishi S, Nakayama Y, Ishibashi-Ueda H, Okamoto Y, Yoshida M. Development of microporous self-expanding stent grafts for treating cerebral aneurysms: designing micropores to control intimal hyperplasia. J Artif Organs 2011; 14:348-356.

* cited by examiner

DEVICES AND METHODS FOR OCCLUSION OF AN ATRIAL APPENDAGE

CROSS-REFERENCE TO RELATED APPLICATION

This application is a continuation of U.S. application Ser. No. 17/400,830, filed Aug. 12, 2021, which is a continuation of U.S. application Ser. No. 15/154,695, filed May 13, 2016, which claims priority to Provisional Application No. 62/161,742, filed May 14, 2015, all of which are herein incorporated by reference in their entireties.

TECHNICAL FIELD

The present disclosure relates to implantable medical devices that may be used to occlude apertures, conduits, spaces, organs, and other structures within a patient.

BACKGROUND

Cardiac structures such as atrial appendages can contribute to cardiac blood flow disturbance, which is associated with a number of cardiac-related pathologies. For example, complications caused by blood flow disturbance within an appendage and associated with atrial fibrillation can contribute to embolic stroke.

SUMMARY

Various aspects of the present disclosure provide implantable medical devices that may be used to occlude apertures, conduits, space, organs and other structures within a patient, including structures within the heart. For example, this disclosure provides occlusion devices that can be deployed into a patient. Deployment may occur using transcatheter techniques, although various deployment techniques are contemplated.

The devices, consistent with various aspects of the present disclosure may be deployed into an atrial appendage of the patient. The heart has left and right atrial appendages. Various aspects of the present disclosure are directed toward occlusive devices that provide enhanced conformability of a frame of the device (including the occlusive face) relative to the atrial appendage walls under physiological conditions. In addition, the present disclosure is directed toward occlusive devices that may provide more complete and rapid closure of the appendages including improved sealing of the appendages around the ostium thereof, enhanced clinical outcomes including reduced thrombus formation, reduced occluder embolization, greater conformability, and enhanced clinical ease-of-use, patient safety, and overall efficacy.

Various aspects of the present disclosure are directed toward apparatuses, methods, and systems as relating to occlusion. In certain embodiments, devices for placement in vessels, appendages, and openings in a body may include a unitary self-expanding frame having a proximal end, a distal end, and a longitudinal axis. In certain embodiments, the unitary self-expanding frame may include a face portion having a pre-loaded flat configuration and (i) a center frame portion arranged at the proximal end and (ii) a plurality of elongate members extending from the center frame portion, and a body portion. In certain embodiments, devices may include a membrane attached to the unitary self-expanding frame. In certain embodiments, the plurality of elongate members may be configured to bend or flex substantially in a plane orthogonal to the longitudinal axis and mitigate longitudinal movement of the face portion in response to a compressive force applied to the body portion of the unitary self-expanding frame.

In certain embodiments, devices for placement in vessels, appendages, and openings in a body having an elongated configuration and a deployed configuration may include a nitinol cut-tube frame having a proximal end and a distal end. In certain embodiments, the nitinol cut-tube frame may include a face portion having a center frame portion arranged at the proximal end and including a plurality of arcs arranged around a circumference of the center frame portion, and a plurality of elongate members extending from the center frame portion, and a body portion. In certain instances, the devices may also include a membrane attached to the nitinol cut-tube frame. In addition and in certain instances, the center frame portion and the plurality of elongate members may form a substantially uniform surface, and the center frame portion may be configured to provide an attachment point for a delivery system for the device.

In certain embodiments, methods of reducing thrombus formation in treatment of left atrial appendage of a patient may include positioning a transcatheter assembly through an ostium of the left atrial appendage. In certain embodiments, the methods may also include deploying a device from the transcatheter assembly, the device comprising: a unitary self-expanding frame having a proximal end, a distal end, and a longitudinal axis, the unitary self-expanding frame including a face portion having a center frame portion arranged at the proximal end and a plurality of elongate members extending from the center frame portion, a body portion arranged substantially orthogonal to the face portion, and a membrane attached to the unitary self-expanding frame, wherein the face portion and the membrane define an occlusive face of the device. In addition and in certain embodiments, the methods may include absorbing one or more forces from the left atrial appendage with thereby flexing the plurality of elongate members in a plane orthogonal to the longitudinal axis to mitigate longitudinal movement of the face portion in response thereto.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1B:
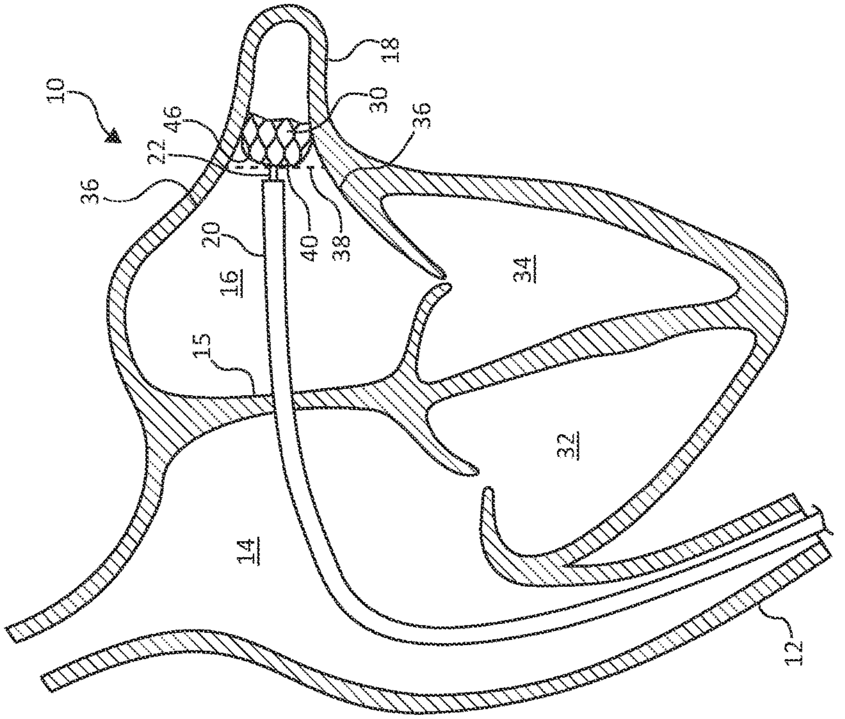
FIG. 1B shows the configuration of FIG. 1A with the occlusive device deployed from the delivery system and positioned within the LAA, in accordance with various aspects of the present disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

Figure 1A:
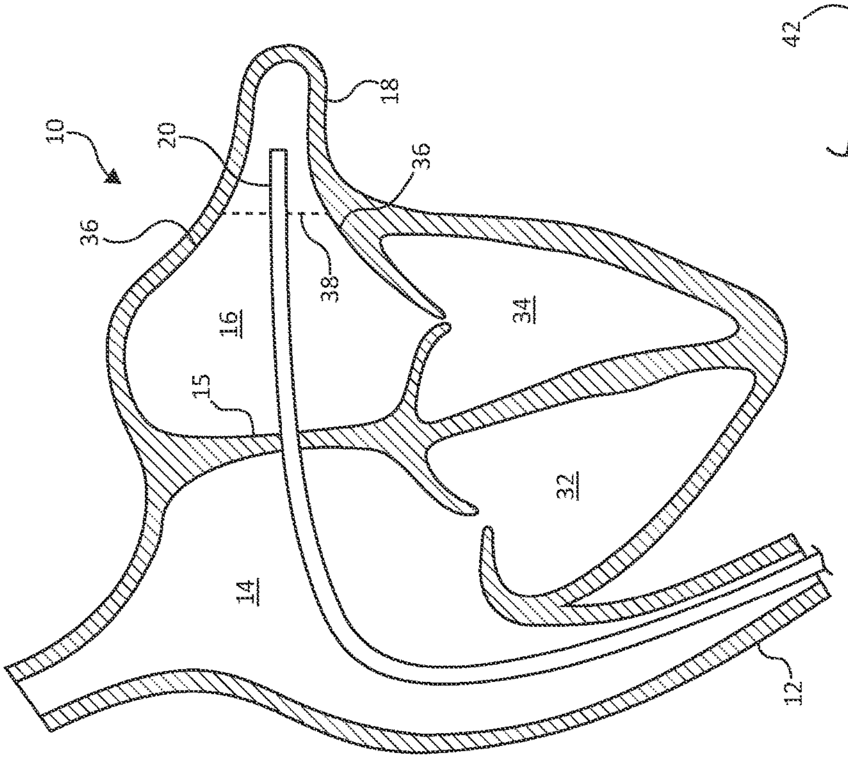
FIG. 1A is a cross-sectional view of a human heart in which a delivery system is positioned in preparation for deployment of an occlusive device into a LAA of the heart, in accordance with various aspects of the present disclosure.

FIGS. 1A-B are a cross-sectional views of a human heart 10 in which a delivery system 20 is positioned in preparation for deployment of an occlusive device 30 into an appendage 18 of the heart, in accordance with various aspects of the present disclosure. FIGS. 1A-B show a depiction of includes a right atrium 14, a left atrium 16, a right ventricle 32, and a left ventricle 34 of the heart 10. As is shown, the appendage 18 is located in the left atrium 16 of the heart 10, and thus, the appendage 18 may be considered the left atrial appendage 18. Although the following discussion focuses on deployment of the occlusive device 30 into the left atrial appendage 18, the occlusive device 30 may be deployed in other appendages or openings within the human heart 10 or in other locations of the human body.

The left atrial appendage 18 may be considered a muscular pouch extending from the anterolateral wall 36 of the left atrium 16 of the heart 10, which serves as a reservoir for the left atrium 16. In a normal cardiac cycle, the left atrial appendage 18 may contract rhythmically with the rest of the left atrium 16 during contraction of the heart 10. Thus, during a normal cardiac cycle, the left atrial appendage 18 contracts with the left atrium 16 and pumps blood that may gather or collect within the left atrial appendage 18 to circulate therefrom. However, during cardiac cycles characterized by arrhythmias (e.g., atrial fibrillation), the left atrial appendage 18 may fail to sufficiently contract along with the left atrium 16, which can allow blood to stagnate within the left atrial appendage 18. Stagnant blood within the atrial appendage 18 is susceptible to coagulating and forming a thrombus, which can dislodge from the atrial appendage 18 and ultimately result in an embolic stroke. The occlusive device 30, consistent with various aspects of the present disclosure, may be delivered to the left atrial appendage 18 to help prevent and militate against blood stagnation within the left atrial appendage 18.

In certain instances and as is shown in FIGS. 1A-B, the occlusive device 30 may be delivered to the left atrial appendage 18 by way of a minimally invasive transcatheter procedure. More specifically, the delivery system 20 may be navigated through a vena cava 12, into the right atrium 14, through an atrial septum 15, and into the left atrium 16 towards the appendage 18. In some implementations, the percutaneous access to the patient's vasculature can be at the patient's femoral vein, for example. It should be understood that this example technique is merely one example, and many other access techniques can also be performed to deploy the occlusive devices provided herein. At this point of the deployment process, the occlusive device is contained within a lumen of the delivery system 20, and is configured in a collapsed low-profile delivery configuration. Although transcatheter systems are generally shown and described, other delivery systems (e.g., thoracoscopic) are also contemplated.

FIG. 1B shows the configuration of FIG. 1A with the occlusive device 30 deployed from the delivery system 20 and positioned within the left atrial appendage 18, in accordance with various aspects of the present disclosure. As shown, a control catheter 22 may releasably couple to the occlusive device 30, and is slidably disposed within the lumen of the delivery system 20. The control catheter 22 can be used by a clinician operator to make the occlusive device 30 deploy from the delivery system 20. For example, after positioning the occlusive device 30 through an ostium 38 of the left atrial appendage 18, the clinician operator can retract the delivery system 20 in relation to the control catheter 22 to unsheath and deploy the occlusive device 30. The ostium 38 may be considered a portion of the anterolateral wall 36 of the left atrium 16 from which a taper originates to form the pouch-like structure of the left atrial appendage 18. The occlusive device 30 may include an occlusive face 40 that is arranged near the ostium 38 of the left atrial appendage 18. As discussed in further detail below (e.g., with reference to FIG. 6A-B), the control catheter 22 may releasably couple to the occlusive device 30 via a hub or center frame portion or a plug (or the like) inserted into the center frame portion arranged centrally within the occlusive face 40 of the occlusive device 300.

After emerging from the constraining confines of the delivery system 20, the occlusive device 30 can reconfigure to an expanded configuration. The occlusive device 30 may expand to conform to the contours of the space defined within the left atrial appendage 18. In certain instances, positioning of the occlusive device 30 relative to the ostium 38 of the left atrial appendage 18 may be enhanced and ensures that the occlusive device 30 prevents thrombus from embolizing from the left atrial appendage 18. More specifically, the occlusive face 40 may be arranged within the left atrial appendage 18 such that the occlusive face 40 connects portions of the anterolateral wall 36 on opposite sides of the ostium 38 to form a substantially uniform surface. In certain instances, blood may collect or stagnate along the face of a device implanted therein if the occlusive face is non-uniform (e.g., a device having a hub that protrudes beyond other portions of the occlusive face; a device having a occlusive face that is concave, partially concave, or includes depressions, a device having a occlusive face that is concave, partially concave, or includes depressions and a covering attached thereto that may drape or wrinkle as a result of the non-uniform face) relative to the ostium 38 of the left atrial appendage 18 or the occlusive face includes protuberances. In these instances, thrombus may occur along the face of the occlusive device as a non-uniform surface may alter/disrupt the blood flow within the left atrium 18. Thus, a patient may remain susceptible to blood coagulation and thrombus formation if an occlusive device includes a non-uniform surface as the result of improper positioning or the design of the device.

After proper positioning and delivery of the occlusive device 30, the control catheter 22 can be decoupled from the occlusive device 30, and the delivery system 20 and control catheter 22 can be removed from the patient. With the occlusive device 30 deployed as shown, the space defined within the left atrial appendage 18 is essentially separated from the left atrium 16 by virtue of the physical barrier provided by the occlusive device 30. In this manner, stagnant blood within the LAA 18 that is susceptible to coagulating and forming thrombi may be prevented from entering the left atrium 16, and thereby prevented from potentially causing an embolic stroke. In addition, positioning of the occlusive face 40 of the occlusive device 30 relative to the ostium 38 of the left atrial appendage 18 may help prevent blood collecting or stagnating along the face of the occlusive device 30.

Figure 1C:
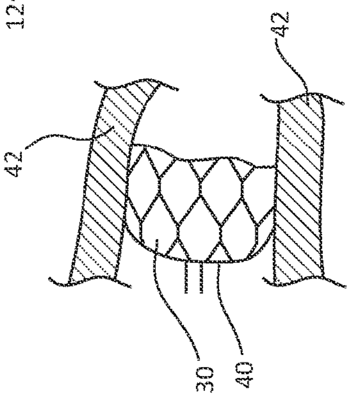
FIG. 1C shows the configuration of FIG. 1A with the occlusive device deployed from the delivery system and positioned within a vessel, in accordance with various aspects of the present disclosure.

As noted above, the occlusive devices provided herein can be used in many different areas of the body, and that deployment of the occlusive device 30 into the left atrial appendage 18 is merely one example implementation. More specifically, FIG. 1C shows the configuration of FIG. 1A with the occlusive device 30 deployed from the delivery system and positioned within a vessel between the vessel walls 42, in accordance with various aspects of the present disclosure.

Figure 2:
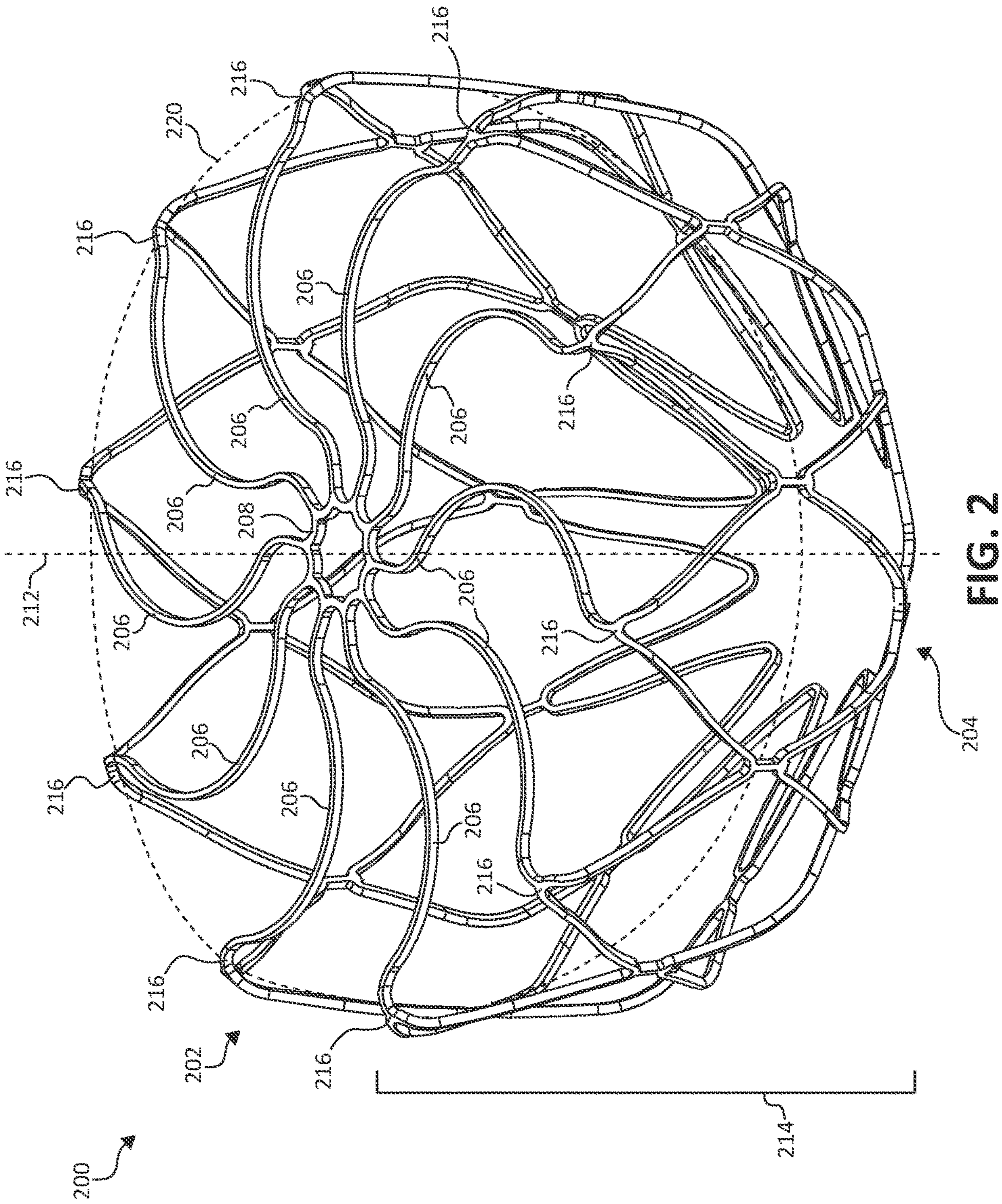
FIG. 2 is a perspective view of an example frame for an occlusive device, in accordance with various aspects of the present disclosure.

FIG. 2 is a perspective view of an example frame 200 for an occlusive device. As shown, the frame 200 may include a proximal end 202 and a distal end 204, and may be unitary and self-expanding. In addition, the frame 200 may include a plurality of elongate members 206 and a center frame portion 208 arranged at the proximal end 202 of the frame 200. The plurality of elongate members 206 may extend from the center frame portion 208. Together, the combination of the plurality of elongate members 206 and the center frame portion 208 form a face portion 220. In addition, the frame 200 may include a body portion 214. The frame 200, including the plurality of elongate members 206 and the center frame portion 208, is shown in a pre-loaded flat configuration. In certain instances and as discussed in further detail relative to FIGS. 5A-B, the frame 200 may be slightly bowed as a result of being loaded into and deployed from a delivery system. In the pre-loaded flat configuration and as shown, the plurality of elongate members 206 and the center frame portion 208 (the face portion 220) form a substantially planar surface (e.g., between 0 mm and 1 mm outward deflection measured from transition portions 216). In certain instances, the center frame portion 208 is a hole having an inner and outer circumference and a plurality of elongate members 206 radiate outward from the outer circumference of the center frame portion 208.

The face portion 220 may be formed by the center frame portion 208 and plurality of elongate members 206. A boundary of the face portion 220 may be considered to be at transition portions 216 of the frame 200. As shown, the transition portions 216 are arranged around a periphery of the face portion 220. The transition portions 216 transition the frame 200 between the plurality of elongate members 206 and the body portion 214 are external to the face portion 220. More specifically, the body portion 214 of the frame 200 extends from the plurality of elongate members 206, and the transition portions 216 transitions the plurality of elongate members 206 of the frame 200 to the body portion 214 of the frame 200. As discussed in further detail below and in certain embodiments, transition portions 216 may be configured as a landing zone that contact the walls of the appendage or vessel into which the frame 200 (as part of an occlusive device) is implanted. The transition portions 216 may enhance conformability of the frame 200 relative to the walls of the appendage or vessel.

The body portion 214 may include any number of rows and cells. The body portion 214 may bifurcate to form multiple cells in a row, or the body portion 214 may extend directly to the distal end 204 of the frame. In certain embodiments, the body portion 214 may include cells formed of a five-sided shape, a six-sided shape, or other shapes such as, but not limited to, polygonal, square, rectangular, parallelogram-shaped, rhomboidal, trapezoidal, diamond-shaped, chevron-shaped, octagonal, triangular, and the like. Different shapes and arrangements of the body portion 214 are shown, for example, in FIGS. 13-18.

In certain instances, the plurality of elongate members 206 are configured to flex and mitigate longitudinal movement (relative to a longitudinal axis 212 of the frame 200)

of the face portion 220 in response to a compressive force applied to the body portion 214 of the frame 200. In some embodiments, the force is applied to the transition portions 216. The plurality of elongate members 206 may enhance fatigue resistance of the frame 200 by functioning as stress relief features that absorb flexure and/or torque, and the like, in response to one or more forces being applied to the frame 200. In certain instances and as disused in further detail below with respect to FIGS. 5A-B, the plurality of elongate members 206 configured to mitigate movement of the face portion 220 substantially outward from the plane, and movement outward from the plane may include outward deflection of the face portion 220.

As shown, the face portion 220 is a substantially uniform (proximal) surface formed by the plurality of elongate members 206 and the center frame portion 208. The plurality of elongate members 206 and the center frame portion 208 may include an equal and constant surface across the face portion 220. In addition, the plurality of elongate members 206 and the center frame portion 208 may be formed without protrusions outward from the face portion 220. In certain instances, the plurality of elongate members 206 and the center frame portion 208 may include approximately equal thickness (relative to the longitudinal axis 212) across the face portion 220. As discussed in further detail below, the face portion 220 having a substantially uniform surface or a surface without protrusions outward therefrom may enhance performance of an occlusive device that includes the frame 200 by mitigating the opportunity for thrombus formation. In certain instances, the substantially uniform surface of the face portion 220 may be planar.

As noted above, the plurality of elongate members 206 are configured to bend or flex substantially in a plane (formed by the face portion 220) orthogonal to the longitudinal axis 212 to mitigate longitudinal movement (relative to the longitudinal axis 212 of the frame 200) of the face portion 220 in response to a compressive force applied to the body portion 214 of the frame 200. The force may be considered a compressive force, and the compressive force may be applied to one or more locations on the body portion 214 of the frame 200. In certain instances, the compressive force may be non-uniform relative to the frame 200, and in other instances the force may be considered a radial force, which may be defined as a force, or a component of a force, that is directed inwardly from one or more locations relative to the frame 200. In all or any of these instances, the force applied to one or more locations on the body portion 214 is directed along the body portion 214 toward the plurality of elongate members 206. The plurality of elongate members 206 may absorb the applied force(s), and balance and/or share the applied force(s) throughout the frame 200. As a result, the plurality of elongate members 206 bend or flex substantially in the plane orthogonal to the longitudinal axis 212 to mitigate movement of the face portion 220 (the combination of the plurality of elongate members 206 and the center frame portion 208) relative to the longitudinal axis 212 in response to a force applied to the frame 200. In addition and in certain instances, the plurality of elongate members 206 flex and mitigate movement of the face portion 220 independent of the shape or arrangement of the body portion 214 of the frame 200.

Mitigating movement of the face portion 220 of the frame 200 may enhance performance of the frame 200 when implanted in a vessel or opening in a body. More specifically, when the frame 200 (or an occlusive device that includes the frame 200) is positioned within, for example, the contours of the space defined within a left atrial appendage (e.g., left atrial appendage 18 shown in FIGS. 1A-B or within a vessel as shown in FIG. 1C), thrombosis may occur along an occlusive device in instances where a non-uniform surface alters a blood flow across the face of the device. Mitigating movement of the face portion 220 longitudinally decreases the opportunity for thrombus formation by avoiding disruption of the blood flow. In addition, the face portion 220 having a substantially uniform surface or a surface without protrusions outward therefrom similarly enhances performance by avoiding disruption of the blood flow. In addition, occlusive devices having an occlusive face with depressions (e.g., curvature of at least a portion of the occlusive face inwardly) may not only disrupt blood flow by allowing blood to pool along the occlusive face but blood may collect within the depressions. Each of these instances may contribute to thrombus formation. In certain instances, such a device that includes depressions in the occlusive face may utilize a membrane to attempt to provide a uniform surface. The membrane may dip within the depression or wrinkle as a result of the non-uniform surface, and therefore disrupt blood flow across the occlusive face. Thus, the frame 200 including a uniform face portion 220 and also mitigating against movement of the face portion 220 in response to forces applied to the frame 200 may enhance performance of an occlusive device that includes the frame 200 by mitigating the opportunity for thrombus formation.

In addition, the plurality of elongate members 206 being configured to flex and mitigate movement of the face portion 220 longitudinally relative to the longitudinal axis 212 may enhance the conformability of the frame 200. More specifically, the plurality of elongate members 206 may facilitate the ability of the frame 200, and more particularly the body portion 214, to conform to irregular tissue topographies and/or dynamically variable tissue topographies. When the frame 200 is implanted into variable tissue topography, force applied from the tissue topography may be directed to one or more locations on the body portion 214 and/or the transition portions 216. In certain instances, this force is directed along a length of the body portion 214 toward the plurality of elongate members 206, and the plurality of elongate members 206 absorb the applied force(s), and balance and/or share the applied force(s) throughout the frame 200. As a result, portions of the frame 200 that contact the variable tissue topography may conform thereto (as opposed to a frame forcing the variable tissue topography to conform to the shape of the frame). In addition, the transition portions 216 of the frame 200 may conform to the shape of an ostium when implanted. In certain instances, the frame 200 (which may include a membrane attached thereto) may be positioned within a left atrial appendage to help prevent thrombus from embolizing from the left atrial appendage (e.g., as shown above in FIG. 1B). After implantation, portions of the frame 200 that contact the left atrial appendage conform thereto, and forces that are applied via the left atrial appendage may be absorbed by the plurality of elongate members 206. Under physiological conditions of the heart the plurality of elongate members 206 are configured to maintain the face portion 220 on opposite sides of an ostium of the left atrial appendage to form and maintain a substantially uniform surface closing off the ostium while allowing the transition portions 216 and portions of the body portion 214 that contact the appendage are configured to conform to the shape of the appendage.

Such conformability characteristics can be advantageous for providing substantial occlusion (sealing) and durable occlusion. Conformability can also enhance the fatigue resistance of the occlusive devices. Further, occlusive devices with substantial conformability are less traumatic to the patient and may tend to resist in situ migration better than occlusive devices with less conformability. In some embodiments of the occlusive devices provided herein, some portions of the devices are designed to be more conformable than other portions of the same device. That is, the conformability of a single occlusive device can be designed to be different at various areas of the device. Additionally, in some embodiments frame material selection, heat treatments and other treatments can be used to attain a desired extent of conformability. In certain instances, the frame 200 may be formed from nitinol (NiTi). In certain more specific embodiments, the frame 200 may be formed from a single unitary piece of nitinol.

To deliver the frame 200 to locations within the body, the frame 200 may be reconfigured to a low-profile (elongated) configuration for loading into a delivery catheter (e.g., such as the control catheter 22 shown in FIGS. 1-B) used for transcatheter deployment of the occlusive device. After emerging from the constraining confines of a delivery system, the frame 200 is configured to self-expand and reconfigure to the configuration shown in FIG. 2. The frame 200, for example, may be expanded to conform to the contours of the space defined within the body (e.g., left atrial appendage 18 shown in FIGS. 1A-B or within a vessel as shown in FIG. 1C). As noted above, the center frame portion 208 may serve as the connection point to a control catheter for transcatheter deployment of the occlusive device. As a result, the frame 200 (and the occlusive device that includes the frame 200) may have a face portion 220 that is hubless (e.g., no addition structure or element beyond that of the center frame portion 208, lacking in additional thickness beyond that of the center frame portion 208, rimless, or lacking in dimension beyond a maximum thickness of the plurality of elongate members 206 and the center frame portion 208). The face portion 220 lacking a hub (e.g., such as any eyelet that extends beyond the face portion 220) provides for an approximately uniform surface formed by the plurality of elongate members 206 and the center frame portion 208.

The illustrative components shown in FIG. 2 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 2 may be, in embodiments, integrated with various other components depicted therein (and/or components not illustrated), all of which are considered to be within the ambit of the disclosed subject matter. For example, the frame 200 described with reference to FIG. 2 may be used in connection with delivery system 20 (shown in FIGS. 1A-B). More specifically, the frame 200 may form a portion of occlusive device 30 (e.g., with the plurality of elongate members 206 and the center frame portion 208 forming a portion of the occlusive face 40). In addition, the frame 200 may include a membrane attached thereto (e.g., as shown and discussed with reference to FIG. 7).

Figure 3:
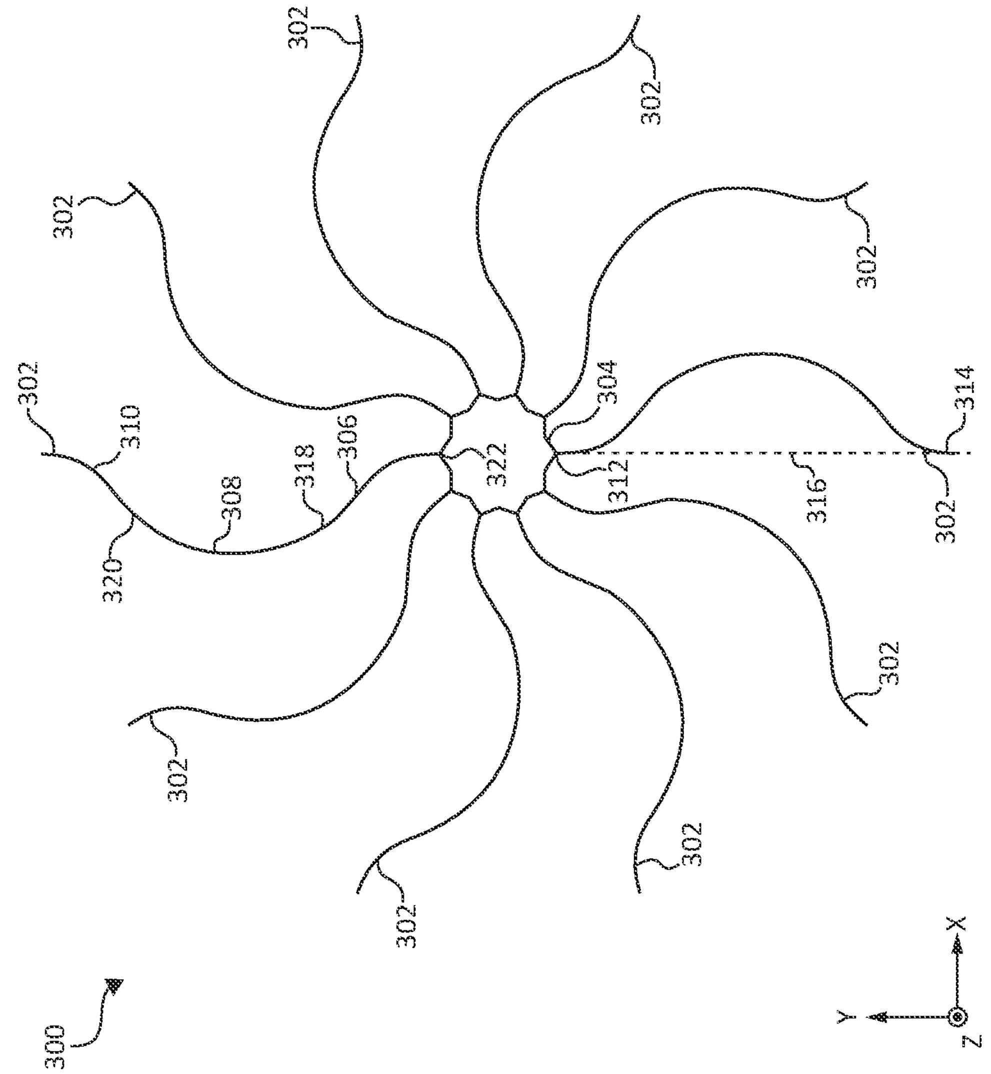
FIG. 3 is a top view of an illustration of an example face portion of an occlusive device, in accordance with various aspects of the present disclosure.
Figure 8:
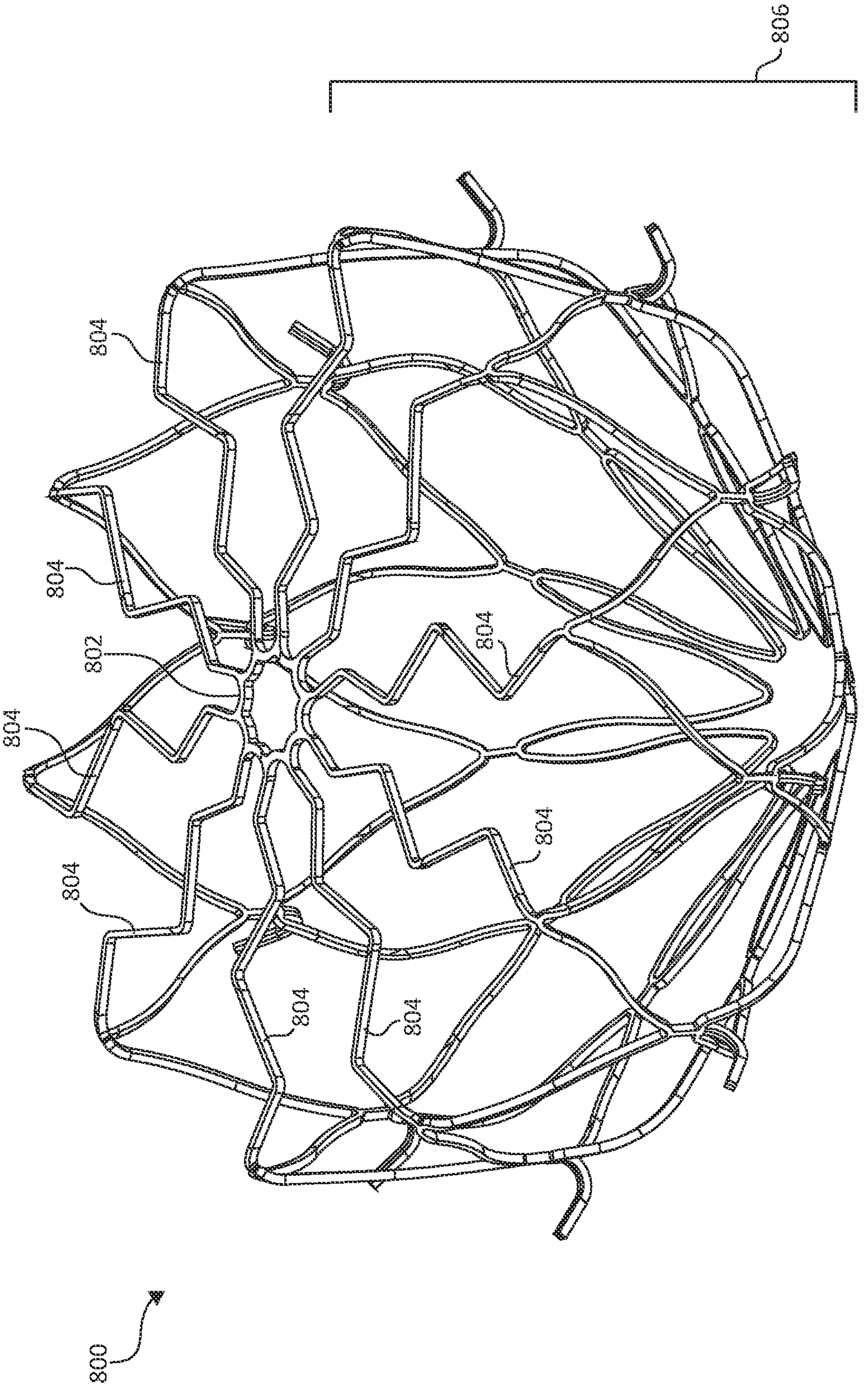
FIG. 8 is a perspective view of another example frame for an occlusive device, in accordance with various aspects of the present disclosure.

FIG. 3 is a top view of an illustration of an example face portion 300 of an occlusive device, in accordance with various aspects of the present disclosure. The face portion 300 includes a plurality of elongate members 302 and a center frame portion 304. As shown, the plurality of elongate members 302 may extend from the center frame portion 304 and include a common curvature within the face portion 300, which is formed substantially within a common plane (e.g., the x-y plane, as shown). The common curvature may provide for the plurality of elongate members 302 to be non-overlapping within the face portion 300. In certain instances, the plurality of elongate members 302 may have a zig-zag pattern (e.g., as shown in FIG. 8).

The plurality of elongate members 302 may include any number of curvature or semi-curved patterns. Other curvature patterns are shown, for example, in FIGS. 8-11. As shown, each of the plurality of elongate members 302 includes multiple curved sections. For illustrative purposes, the curved sections are highlighted for one of the plurality of elongate members 302 in FIG. 3. The plurality of elongate members 302 may include a first curved section 306, a second curved section 308, and a third curved section 310. In certain instances, the first curved section 306 and the third curved section 310 are curved in a first direction, and the second curved section 308 is curved in a second direction that is opposite that of the first direction. As a result, the plurality of elongate members 302 may include a first inflection point 318 between the first curved section 306 and the second curved section 308, and a second inflection point 320 between the second curved section 308 and the third curved section 310. The first inflection point 318 and the second inflection point 320 alter the curvature of the plurality of elongate members 302.

In addition, each of the first curved section 306, the second curved section 308, and the third curved section 310 are arranged within the common plane. Thus, the plurality of elongate members 302, and the curvature formed by the first curved section 306, the second curved section 308, and the third curved section 310 occurs substantially within the x-y plane. More specifically, each of the first curved section 306, the second curved section 308, and the third curved section 310 are curved within the x-y plane. The center frame portion 304 may also be arranged with the x-y plane. When the face portion 300 is included with an occlusive device, the plurality of elongate members 302 and the center frame portion 304 may be arranged within a common plane. In addition and when the face portion 300 is included with an occlusive device, the plurality of elongate members 302 are configured to flex and mitigate longitudinal movement (orthogonal to the x-y plane) of the face portion 300 in response to a compressive force applied to another portion of the occlusive device (e.g., as discussed above in detail with reference to FIG. 2). The plurality of elongate members 302 are configured to flex or bend substantially within the x-y plane to mitigate longitudinal movement (orthogonal to the x-y plane) of the face portion 300.

In certain instances, each of the first curved section 306, the second curved section 308, and the third curved section 310 may include equal radiuses of curvature. In other instances, the first curved section 306 and the third curved section 310 may include a first radius of curvature, the second curved section 308 may include a second (and different) radius of curvature. The (first) radius of curvature of the first curved section 306 and the third curved section 310 may be larger than the (second) radius of curvature of the third curved section 310. In addition and in certain instances, the first curved section 306 and the third curved section 310 may include approximately equal lengths. The second curved section 308 may include a length that is equal to or greater than the first curved section 306 and the third curved section 310. In addition, the first curved section 306 and the third curved section 310 may include lengths greater than the length of the second curved section 308. As shown, the length of the second curved section 308 is greater than the first curved section 306 and the third curved section 310, which are substantially equal in length.

As noted above, the plurality of elongate members 302 extend from the center frame portion 304. Thus, a start point 312 for the plurality of elongate members 302 is arranged at the center frame portion 304, and an end point 314 for the plurality of elongate members 302 is arranged at a periphery of the face portion 300. For illustrative purposes, the start point 312 and the end point 314 is shown for one of the plurality of elongate members 302 in FIG. 3. In certain instances, the start point 312 and the end point 314 may be symmetrically arranged with respect to the face portion 300. More specifically, a tangent 316 formed between the start point 312 and the end point 314 may be substantially linear. The pattern of the curvature of the plurality of elongate members 302 may be symmetric such that the plurality of elongate members 302 include a curvature (having one or more inflection points) in a direction from the start point 312 and back in another direction to the end point 314.

In the depicted embodiment, the face portion 300 includes ten of the plurality of elongate members 302. In some embodiments, the face portion 300 may include two, three, four, five, six, seven, eight, nine, eleven, twelve, thirteen, fourteen, fifteen, sixteen, or more than sixteen of the plurality of elongate members 302. In addition, the center frame portion 304 is shown to include ten peaks 322 that correspond to each of the plurality of elongate members 302. The center frame portion 304 may include an equal number of peaks to the number of the plurality of elongate members 302 included with the face portion 300. In other instances, the center frame portion 304 may include a substantially circular shape.

The illustrative components shown in FIG. 3 are not intended to suggest any limitation as to the scope of use or functionality of embodiments of the disclosed subject matter. Neither should the illustrative components be interpreted as having any dependency or requirement related to any single component or combination of components illustrated therein. The face portion 300 may be integrated with various other occlusive devices depicted herein (and/or components not illustrated), all of which are considered to be within the ambit of the disclosed subject matter. For example, the face portion 300 may be used in connection with the frame 200 shown in FIG. 2.

Figure 4A:
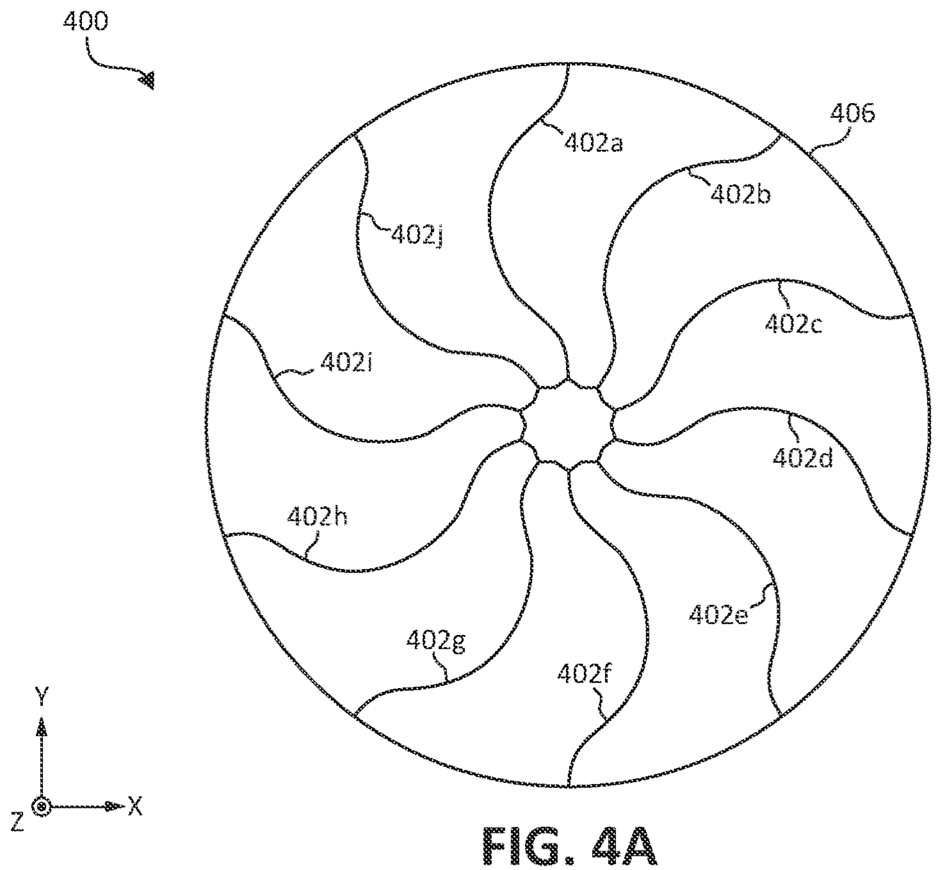
FIG. 4A is a schematic representation of a top view of an example face portion of an occlusive device in a first configuration prior to a force being applied, in accordance with various aspects of the present disclosure.

FIG. 4A is a schematic representation of a top view of an example face portion 400 of an occlusive device in a first configuration prior to a force being applied, in accordance with various aspects of the present disclosure. The face portion 400 includes a plurality of elongate members 402*a-j* and a center frame portion 404. The plurality of elongate members 402*a-j* extend from the center frame portion 404. The center frame portion 404 and the plurality of elongate members 402*a-j* are arranged within an x-y plane. The plurality of elongate members 402*a-j* and the center frame portion 404 may be formed from a unitary frame. The unitary frame may be formed by laser cutting (e.g., a tube or flat sheet), etching, wire forming, or other processes.

In addition, the face portion 400 may be a substantially uniform surface or thickness. The plurality of elongate members 402*a-j* and a center frame portion 404 may include an equal and constant surface across the face portion 400 such that the face portion 400 is without protrusions (e.g., relative to the z-axis). The face portion 400 having a substantially uniform surface or a surface without protrusions outward therefrom may enhance performance of an occlusive device that includes the frame 400 by mitigating against the disruption of blood flow across the face portion 400 thereby reducing the opportunity for thrombus formation.

For illustrative purposes, a peripheral boundary 406 of the face portion 400 is shown. In certain instances, the peripheral boundary 406 may be considered a non-physical boundary that is formed by end portions of the plurality of elongate members 402*a-j* (e.g., the face portion 220 formed around the transition portions 216 as shown in FIG. 2). In other instances, the peripheral boundary 406 may be a physical boundary formed by portions of a frame that form the face portion 400. In either instance and as discussed in further detail below with respect to FIG. 7, the face portion 400 may include a membrane attached thereto. Membranes are attached to provide a barrier for thrombus being embolized from appendage or vessel as well as to enhance sealing. Membranes suitable for use include occlusive or semi-occlusive materials. Embodiments with semi-occlusive materials may allow passage of some fluids/blood components while inhibiting the passage of thrombus. In these instances, the peripheral boundary 406 may be formed by the boundary of the membrane.

The face portion 400 may be incorporated with an occlusive device (e.g., via the frame 200 shown and discussed above with reference to FIG. 2). The occlusive device that includes the face portion 400 may include a longitudinal axis that is parallel to the z-axis shown in FIG. 4A. Thus, the occlusive device that includes the face portion 400 has the center frame portion 404 and the plurality of elongate members 402*a-j* arranged in a plane (the x-y plane) orthogonal to the longitudinal axis of the occlusive device. The face portion 400 of such an occlusive device (e.g., as shown in FIG. 2) may be considered a first portion of the occlusive device with a body portion of the occlusive device arranged substantially external and/or orthogonal to the face portion 400 and the x-y plane.

As shown in FIG. 4A, the plurality of elongate members 402*a-j* and the center frame portion 404 are arranged in an initial configuration in which no forces are applied thereto. The plurality of elongate members 402*a-j* may be non-overlapping in the first configuration, and may include a common curvature. In addition, the plurality of elongate members 402*a-j* and the center frame portion 404 are uniform in addition to being arranged within the x-y plane.

Figure 4B:
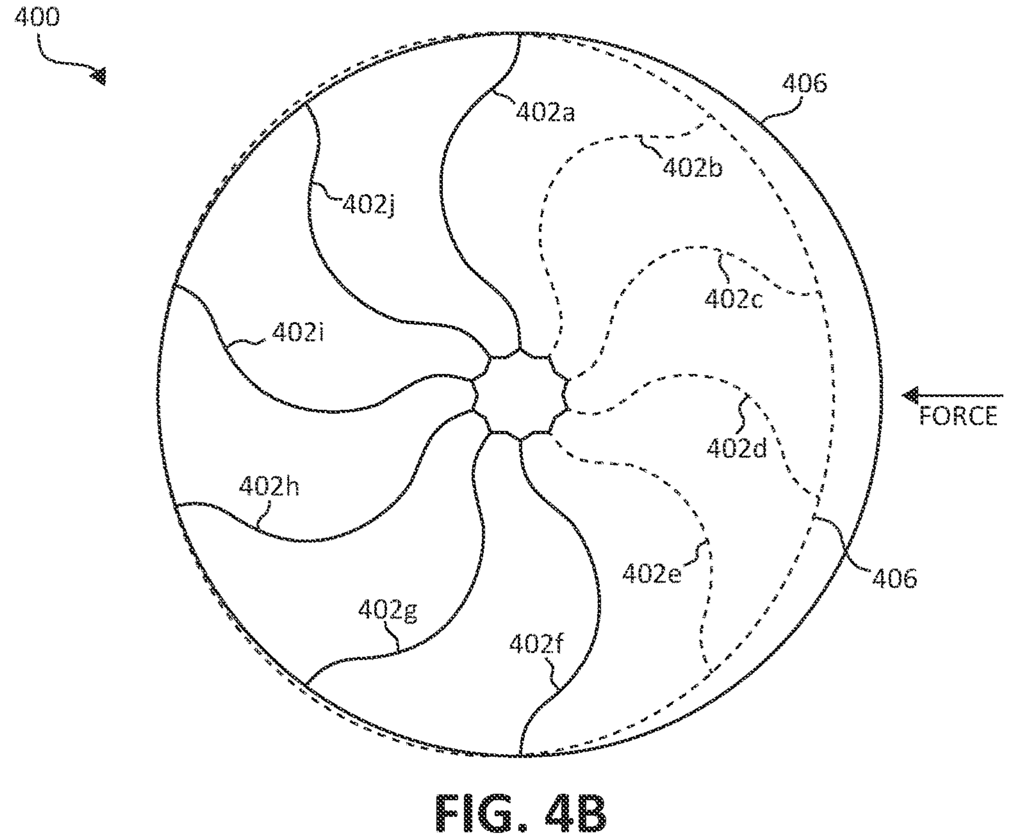
FIG. 4B is a top view of an illustration of the example face portion, shown in FIG. 4A, in a second configuration in response to the force being applied, in accordance with various aspects of the present disclosure.

FIG. 4B is a top view of an illustration of the face portion 400 in a second configuration in response to the force being applied, in accordance with various aspects of the present disclosure. In response to the applied force (shown for illustrative purposes), the plurality of elongate members 402*a-j* are configured to flex and mitigate movement of the face portion 400 relative to the x-y plane. In addition, the plurality of elongate members 402*a-j* are configured to flex or bend substantially within the x-y plane to mitigate longitudinal movement of the face portion 400 relative to the x-y plane. As noted above, the face portion 400 may be incorporated with an occlusive device (e.g., via the frame 200 shown and discussed above with reference to FIG. 2). The applied force, shown in FIG. 4B, may be a compressive force applied to a portion of the occlusive device that is arranged external to the x-y plane. In various implementations, the compressive force corresponds to that associated with portions the device complying with body anatomy (e.g., the heart), including movement of the anatomy. The compressive force may be directed toward the occlusive device non-uniformly from one or more sides of occlusive device. In addition, the compressive force may be directed toward the occlusive device at an angle with respect to the z-axis from one or more sides of occlusive device.

As shown in FIG. 4B and in response to the force applied, one or more of the plurality of elongate members 402*a-j* flex/bend. In certain instances, the plurality of elongate members 402*a-j* are configured such that one or more of the plurality of elongate members 402*a-j* located nearest the compressive force bend to a greater degree than one or more of the plurality of elongate members 402*a-j* that are located further therefrom. More specifically and as shown, the plurality of elongate members 402*b-e* flex/bend (within the x-y plane), whereas the plurality of elongate members 402*a* and 402*f-j* flex/bend to a lesser degree or not at all (within the x-y plane). The plurality of elongate members 402*a* and 402*f-j* may pass the force applied along a length thereof to share the applied force among the plurality of elongate members 402*a* and 402*f-j*. As a result, the flexure of the plurality of elongate members 402*a-j* occurs substantially within the x-y plane in order to mitigate movement of the plurality of elongate members 402*a-j* and the center frame portion 404 external to the x-y plane (in the z direction or perpendicular to the x-y plane).

In certain instances, an occlusive device that includes the face portion 400 may be implanted into variable tissue topography. The forces applied from the tissue topography may be directed to one or more locations. The face portion 400 may be formed as part of a frame of the occlusive device, which may conform to the variable tissue topography. In certain instances, the occlusive device may be positioned within a left atrial appendage to help prevent thrombus from embolizing from the left atrial appendage (e.g., as shown above in FIG. 1B). After implantation, forces that are applied via the left atrial appendage may be absorbed by the plurality of elongate members 402*a-j*. The plurality of elongate members 402*a-j* maintain the face portion 400 within the x-y plane on opposite sides of an ostium of the left atrial appendage to form and maintain the uniformity of the face portion 400 to close off the ostium while allowing the remaining portions of the occlusive device to conform to the shape of the appendage in some embodiments. In other embodiments, only portions of the body portion of the occlusive device that contact the vessel or appendage are configured to conform. The peripheral boundary 406 of the face portion 400 may conform to the shape of the ostium in response to forces applied via the left atrial appendage. For example and as shown comparing FIG. 4A and FIG. 4B, the peripheral boundary 406 may alter its shape in response to forces applied to the occlusive device. The peripheral boundary 406 maintains closure of the ostium of the left atrial appendage while the plurality of elongate members 402*a-j* mitigate against movement of the face portion 400 and maintain the uniformity thereof to avoid thrombus formation.

In each of the first configuration (FIG. 4A) and the second configuration (FIG. 4B), the face portion 400 maintains the substantially uniform surface within the x-y plane. In certain instances, the face portion 400 also maintains a planar surface within the x-y plane. The plurality of elongate members 402*a-j* may also be non-overlapping in each of the first configuration (FIG. 4A) and the second configuration (FIG. 4B).

The illustrative components shown in FIGS. 4A-B are not intended to suggest any limitation as to the scope of use or functionality of embodiments of the disclosed subject matter. Neither should the illustrative components be interpreted as having any dependency or requirement related to any single component or combination of components illustrated therein. The face portion 400 may be integrated with various other occlusive devices depicted herein (and/or components not illustrated), all of which are considered to be within the ambit of the disclosed subject matter. For example, the face portion 400 may be used in connection with the frame 200 shown in FIG. 2.

Figure 5A:
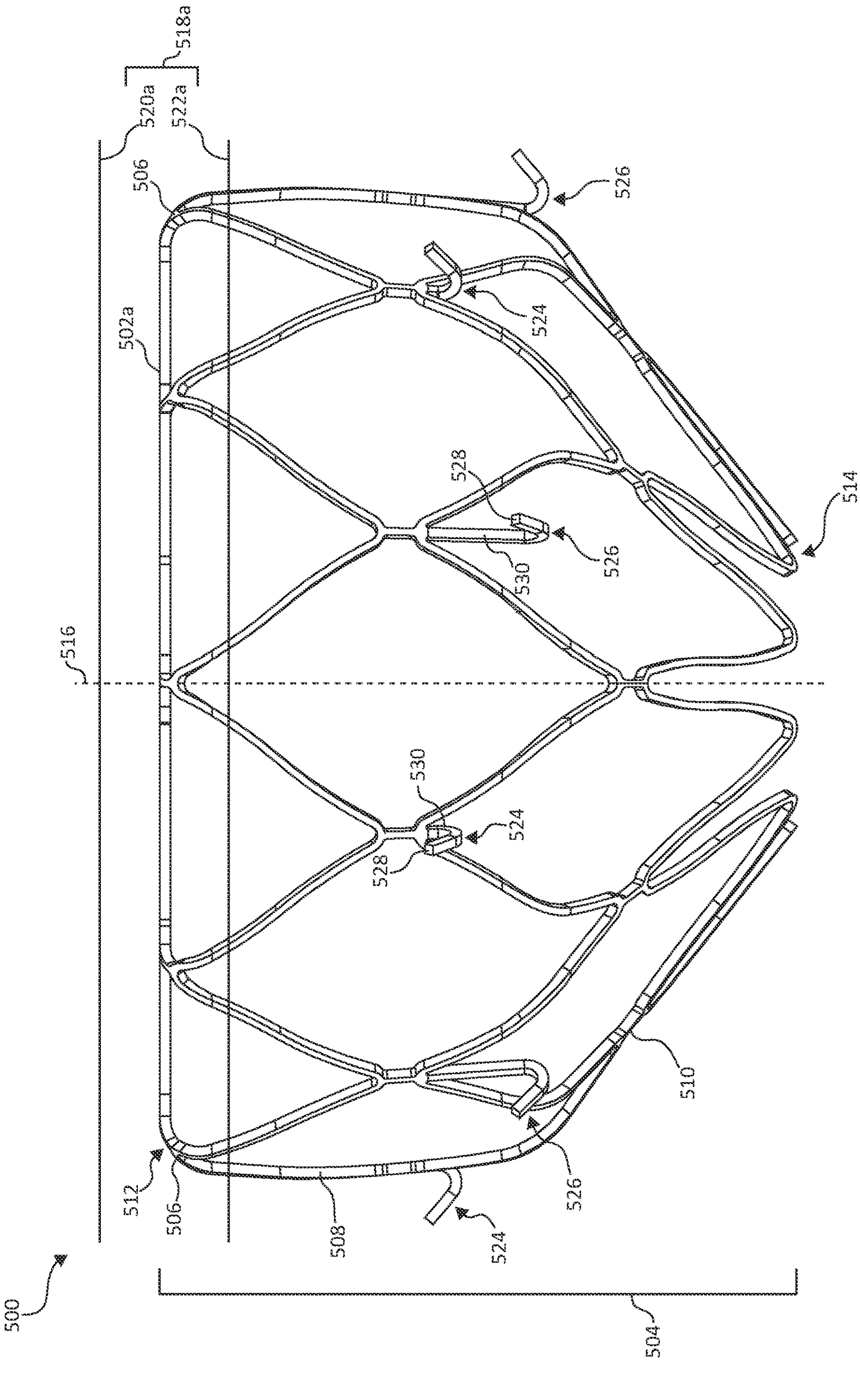
FIG. 5A is a side view of an illustration of another example frame of an occlusive device, in accordance with various aspects of the present disclosure.

FIG. 5A is a side view of an illustration of another example frame 500 of an occlusive device, in accordance with various aspects of the present disclosure. The frame 500 may include a face portion (502*a* and 502*b*) and a body portion 504. Although not shown, the face portion (502*a* and 502*b*) may include a center frame portion and a plurality of elongate members. The center frame portion may be formed consistent with the aspects shown and described with reference to FIGS. 2-4 or FIG. 6A-B, and the plurality of elongate members may be formed consistent with the aspects shown and described with reference to FIGS. 2-4.

The face portion 502*a* is arranged at a proximal end 512 of the frame 500. In addition, the face portion 502*a* may be arranged in a plane 518*a* that is perpendicular or orthogonal to a longitudinal axis 516 of the frame 500. The plane 518*a* may include an upper bound 520*a* and a lower bound 522*a*. In addition, the frame 500 may also include transition portions 506 arranged between the face portion 502*a* (and the plurality of elongate members) and the body portion 504. The transition portions 506 include a curvature to transition the frame 500 from the plane 518 to the body portion 504. In certain instances, the face portion 502*a* may be substantially planar (e.g., orthogonal to the longitudinal axis 516 of the frame 500). In addition, the face portion 502*a* may include a uniform surface. More specifically, the face portion 502*a* has a surface without protrusions external to that of the face portion 502*a*.

Figure 5B:
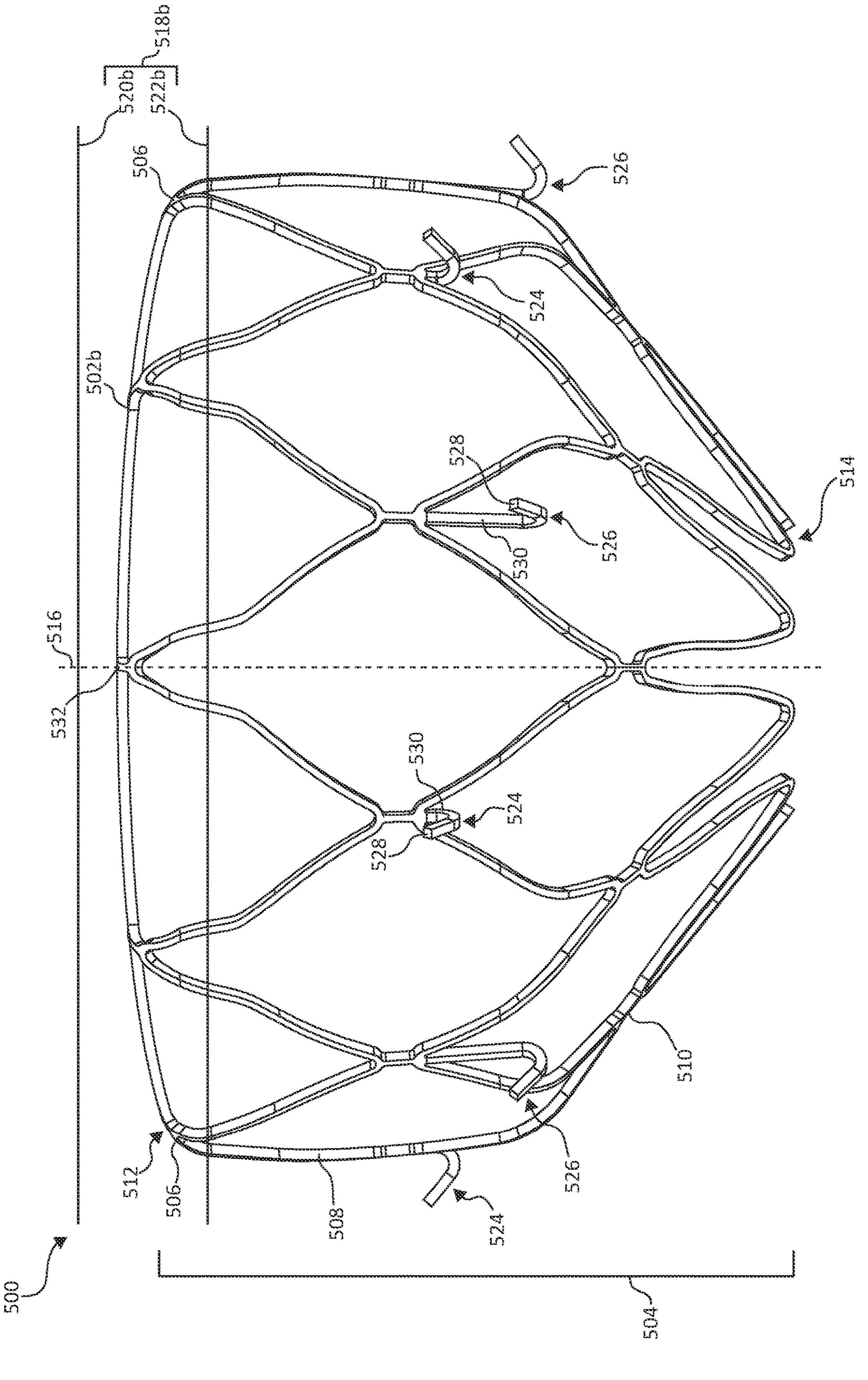
FIG. 5B is a side view of the example frame of an occlusive device with a curvature in the face portion, in accordance with various aspects of the present disclosure.

In certain instances and as shown in FIG. 5B, the frame 500 may include a curvature in the face portion 502*b*, in accordance with various aspects of the present disclosure. The curvature may result from the frame 500 being loaded and unloaded into a delivery system (e.g., as shown and discussed above in FIGS. 1A-B). FIG. 5A shows the frame 500 in a pre-loaded flat configuration. Once loaded and unloaded, a peak 532 of the curvature may be between approximately 1 mm and 3 mm higher or lower than transition portions 506. In the pre-loaded flat configuration shown in FIG. 5A, the face portion is 502*a* is substantially flat or planar (e.g., a peak of curvature of less than 1 mm as measured from the transition portions 506). As with the substantially orthogonal face portion 502*b*, the face portion 502*b* is arranged within the plane 518*b*. In these instances, the plane 518*b* may be parallel to a peak 532 of the curvature of the face portion 502*b*. The plane 518*b* may include an upper bound 520*b* and a lower bound 522*b*. In certain instances, the curvature of the face portion 502*b* may be outward from the frame 500 (as shown) or the curvature of the face portion 502*b* may be inward. Similar to the face portion 502*a*, the face portion 502*b* may include a uniform surface. More specifically, the face portion 502*b* has a surface without protrusions external to that of the face portion 502*b*. More specifically, the face portion 502*b* may be without protrusions relative to the surface of the face portion 502*b* that includes the curvature.

Both the face portion 502*a* and the face portion 502*b* include a plurality of elongate members. As discussed in detail above (e.g., with reference to FIGS. 2-4), the plurality of elongate members are configured to are configured to flex or bend substantially within the plane (518*a* and 518*b*) to mitigate movement of the face portion 502*a* and face portion 502*b* relative to the longitudinal axis 516 in response to a compressive force applied to the body portion 504 of the frame 500. In certain instances, the plurality of elongate members are configured to flex or bend substantially within the plane (518*a* and 518*b*) to mitigate movement of the face portion (502*a* or 502*b*) substantially outward from the plane (518*a* and 518*b*), and movement outward from the plane (518*a* or 518*b*) includes deflection of the face portion (502*a* or 502*b*) of less than 15% outward (15% of an outer diameter of the body portion 214) in response to a the 25% compression of the body portion 504.

The 15% outward deflection is represented by the upper bound (520*a* and 520*b*) of the plane (518*a* or 518*b*). More specifically, the face portion (502*a* and 502*b*) deflects outward from the plane (518*a* or 518*b*) if the deflection is greater than the upper bound (520*a* and 520*b*). As a result and in certain instances, the plurality of elongate members are configured to flex and mitigate movement of the face portion (502*a* and 502*b*) substantially outward from the plane (518*a* or 518*b*) in response to a compressive force applied to the body portion 504 of the frame 500 such that the face portion (502*a* or 502*b*) remains within the upper bound (520*a* and 520*b*) and the lower bound (522*a* and 522*b*).

The force may be considered a compressive force, and the compressive force may be applied to one or more locations on the body portion 504 of the frame 500. In certain instances, the compressive force may be non-uniform relative to the frame 500, and in other instances the force may be considered a radial force, which may be defined as a force, or a component of a force, that is directed inwardly from one or more locations relative to the body portion 504.

In certain instances, the frame 500 may be implanted in a patient. More specifically, when the frame 500 (or an occlusive device that includes the frame 500) is positioned within, for example, the contours of the space defined within a left atrial appendage (e.g., left atrial appendage 18 shown in FIGS. 1A-B), thrombus may occur along an occlusive device in instances where a non-uniform (e.g., having protrusions) surface alters a blood flow across the face of the device. After implantation, forces that are applied to the body portion 504 of the frame via the left atrial appendage may be absorbed by the plurality of elongate members that are included in the face portion (502*a* or 502*b*). The plurality of elongate members are configured to mitigate movement of the face portion (502*a* and 502*b*) longitudinally relative to the longitudinal axis 516 on opposite sides of an ostium of the left atrial appendage to form and maintain a substantially protrusion-free surface that closes off the ostium of the left atrial appendage while allowing the remaining portions (e.g., the body portion 504) of the occlusive device to conform to the shape of the appendage. Mitigating movement of the face portion (502*a* and 502*b*) longitudinally decreases the opportunity for thrombus formation by mitigating against disruption of the blood flow by maintaining a substantially uniform surface across the ostium of the left atrial appendage.

In certain instances, the body portion 504 of the frame 500 may be tapered toward a distal end 514. In some instances, the body portion 504 of the frame 500 may include a first tapered section 508 and a second tapered section 510. The first tapered section 508 and the second tapered section 510 may decrease in circumference at different rates. For example and as shown in FIG. 5A and FIG. 5B, the first tapered section 508 decreases at a rate that is less than a rate at which the second tapered section 510 tapers. The first tapered section 508 may taper at an angle between 0 and 10 degrees, or 0 to 20 degrees, or 0 to 30 degrees from the face portion (502*a* and 502*b*). The second tapered section 510 may taper at an angle between 40 and 75 degrees, 30 and 80 degrees, or 30 and 85 degrees. The frame 500 may include a single taper or multiple tapered sections (first tapered section 508 and second tapered section 510) depending on the intended implantation for an occlusive device that includes the frame 500. The first tapered section 508 and the second tapered section 510 may be manufactured and sized to the specific anatomy of the left atrial appendage.

Some embodiments of the frame 500 are resistant to pleating. For example, certain embodiments of occlusive devices provided herein generally exhibit more resistance to pleating when loading or reloading the devices into a delivery catheter. Pleating is type of deformation such as the folding, curving, kinking, or overlapping of a portion of an occlusive device (e.g., the distal portion) that makes the device configured non-uniformly. Pleating can cause an occlusive device to experience structural entanglement and/or damage, resistance to loading, poor sealing performance, and the like. The “acorn” shape of the frame 500 enhances the resistance of the frame 500 to pleating. It has been found that these such embodiments may be better at prevention of patient trauma in part due to the acorn shape, a membrane with full or fuller coverage of the frame, improved conformability and sealing, better fatigue resistance, and the ePTFE material of the covering which enhances in growth.

In addition, the body portion 504 of the frame 500 may be another shape such as cylindrical, conical, frustoconical, hemispherical, a spherical cap, pyramidal, truncated pyramidal, and the like, and combinations thereof. Any and all combinations and sub-combinations of such varying shapes and varying geometries of shapes are envisioned and within the scope of this disclosure.

In certain instances, the face portion (502*a* or 502*b*), the body portion 504, and the transition portions 506 of the frame 500 are formed from a unitary and self-expanding structure. In certain instances, the frame 500 may be constructed of a unitary piece of material. Therefore, it can be said that in some embodiments the frame 500 include a seamless construction. In addition, the material of the frame 500 may be of a single thickness and/or width through the entirety of the frame 500. In some embodiments, the material of the frame 500 may vary in thickness and/or width so as to facilitate variations in the radial force that is exerted by the frame 500 in specific regions thereof, to increase or decrease the stiffness or flexibility of the frame 500 in certain regions, to enhance migration resistance, and/or to control the process of loading (and/or reloading) the frame 500 into a delivery catheter in preparation for deployment (and/or repositioning and redeployment) of an occlusive device made of frame 500. However, in some embodiments the frame 500 can be constructed differently such that the frame 500 includes two or more portions that are formed separately of each other.

In addition, nitinol (NiTi) may be used as the material of the frame 500 (and any of the frames discussed herein), but other materials such as stainless steel, L605 steel, polymers, MP35N steel, polymeric materials, Pyhnox, Elgiloy, or any other appropriate biocompatible material, and combinations thereof, can be used as the material of the frame 500. The super-elastic properties and softness of NiTi may enhance the conformability of the frame 500. In addition, NiTi can be shape-set into a desired shape. That is, NiTi can be shape-set so that the frame 500 tends to self-expand into a desired shape when the frame 500 is unconstrained, such as when the frame 500 is deployed out from a delivery system. More specifically, the frame 500 (made of NiTi) may have a spring nature that allows the frame 500 to be elastically collapsed or "crushed" to a low-profile delivery configuration for loading in a delivery system (e.g., as shown and discussed with reference to FIG. 1A), and then to reconfigure to the expanded configuration, as shown in FIG. 5A and FIG. 5B, upon emergence from the delivery system. The frame 500 may be generally conformable, fatigue resistant, and elastic such that the frame 500 can conform to the topography of the surrounding tissue when the occlusive device is deployed in a patient. In certain embodiments, bioresorbable or bioabsorbable materials may be used for the frame 500 or a portion thereof, including for example, a bioresorbable or bioabsorbable polymer.

In some embodiments, some portions or the entirety of the frame 500 (and the frames of the other devices provided herein) are coated (e.g., sputter-coated) with a radiopaque coating for enhanced radiographic visibility. For example, in some such embodiments, portions or the entirety of the frame 500 can be coated with a noble metal such as, but not limited to, tantalum, platinum, and the like. In some embodiments the frame 500 is formed from nitinol tubing or sheets of nitinol.

In some embodiments, the frame 500 can be processed using various electro-polishing techniques. In some embodiments, such electro-polishing is performed while the frame 500 is in a cut-tube configuration (prior to diametrical expansion). In some embodiments, such electro-polishing is performed while the frame 500 is in a diametrically expanded and shape-set configuration. In some embodiments, the frame 500 can be processed using various heat treating techniques. The use of such techniques can enhance some desirable performance characteristics of the occlusive devices provided herein such as, but not limited to, increased conformability, increased fatigue resistance, and the reduction of patient trauma from the devices.

The frame 500 may also include one or more anchors 524, 526 arranged with the body portion 504. As shown in FIG. 5A and FIG. 5B, the frame includes a first group of anchors 524 and a second group of anchors 526. Although a single one of each of the first group of anchors 524 and the second group of anchors is highlighted, each of the anchors 524, 526 include an anchoring portion 528 (which may contact a vessel or appendage wall to hold the frame 500 and accompanying occlusive device in place) and an arm 530. In certain instances, the first group of anchors 524 and the second group of anchors 526 may be arranged at the same height, relative to the distal end 514, around a circumference of the frame 500. In other instances, the anchoring portions 528 of the first group of anchors 524 is arranged at a first height, relative to the distal end 514, and the anchoring portions 528 of the second group of anchors 526 is arranged at a second height, relative to the distal end 514, with and the first height being greater than the second height. The heights of the anchoring portions 528 of the first group of anchors 524 and the second group of anchors 526 may be altered by arranging the first group of anchors 524 and the second group of anchors 526 at different heights on the frame 500. In other instances, the heights of the anchoring portions 528 of the first group of anchors 524 and the second group of anchors 526 may be altered by altering lengths of the arm 530. More specifically and as shown, the arm 530 of the first group of anchors 524 may be shorter than the arm 530 of the second group of anchors 526. The difference in height of the first group of anchors 524 and the second group of anchors 526 may be the difference between the lengths of the arm 530 of the first group of anchors 524 and the arm 530 of the second group of anchors 526. In certain instances, the first group of anchors 524 and the second group of anchors 526 and the remaining portions of the frame 500 may be unitary. More specifically, the first group of anchors 524 and the second group of anchors 526 may also be formed from the same unitary piece of material as the remaining portions of the frame 500.

In certain instances, staggering the first group of anchors 524 and the second group of anchors 526 may decrease the amount of force required to transition the frame 500 between the deployed configuration (as shown) and an elongated or delivery configuration via a delivery system. The frame may be positioned within the delivery system (e.g., as shown in FIG. 1A) by withdrawing the frame 500 into a portion (delivery sheath) of the delivery system. In the process of withdrawing the frame 500 into the delivery system, the forced needed to position the frame 500 within the delivery system increases when contacting protrusions (such as anchors). Thus, staggering the first group of anchors 524 and the second group of anchors 526 at different heights also staggers the amount of forced needed to withdraw the anchors 524 and 526 into the delivery system by approximately half relative to a plurality of anchors located at the same height around a frame.

The illustrative components shown in FIG. 5A and FIG. 5B are not intended to suggest any limitation as to the scope of use or functionality of embodiments of the disclosed subject matter. Neither should the illustrative components be interpreted as having any dependency or requirement related to any single component or combination of components illustrated therein. The frame 500 may be integrated with various other occlusive devices depicted herein (and/or components not illustrated), all of which are considered to be within the ambit of the disclosed subject matter. For example, the frame 500 may include a membrane attached thereto (e.g., as shown and discussed with reference to FIG. 7) or the frame 500 may be used in place of the frame 708 included with the occlusive device 700. In addition, the face portions 220, 300, 400 may be incorporated in place of the face portion (502*a* or 502*b*).

Figure 6A:
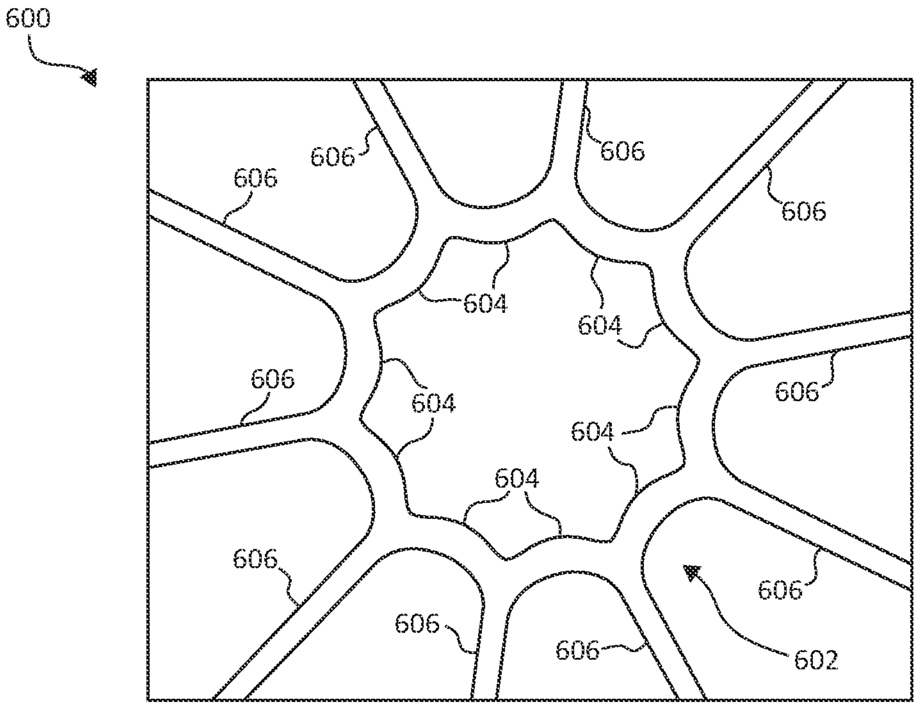
FIG. 6A is a top view of an illustration of a portion of an example frame and center frame portion that may be included with an occlusive device, in accordance with various aspects of the present disclosure.

FIG. 6A is a top view of an illustration of a portion of an example frame 600 and center frame portion 602 that may be included with an occlusive device, in accordance with various aspects of the present disclosure. The frame 600 may be formed from a nitinol material in certain instances. In addition, the frame 600 may be unitary and self-expanding. The center frame portion 602 may include a plurality of arcs 604 arranged around a circumference of the center frame portion 602. The center frame portion 602 may be arranged as a center section of the frame 600 that may be used with an occlusive device, consistent with various aspects of the present disclosure. The frame 600 may be formed from a unitary structure, such as a tube. The tube may be cut in to form the frame 600, which includes the center frame portion 602 and the plurality of arcs 604. The frame 600 also includes a plurality of elongate members 606, which may form a face portion and a body portion of the frame 600.

Figure 6B:
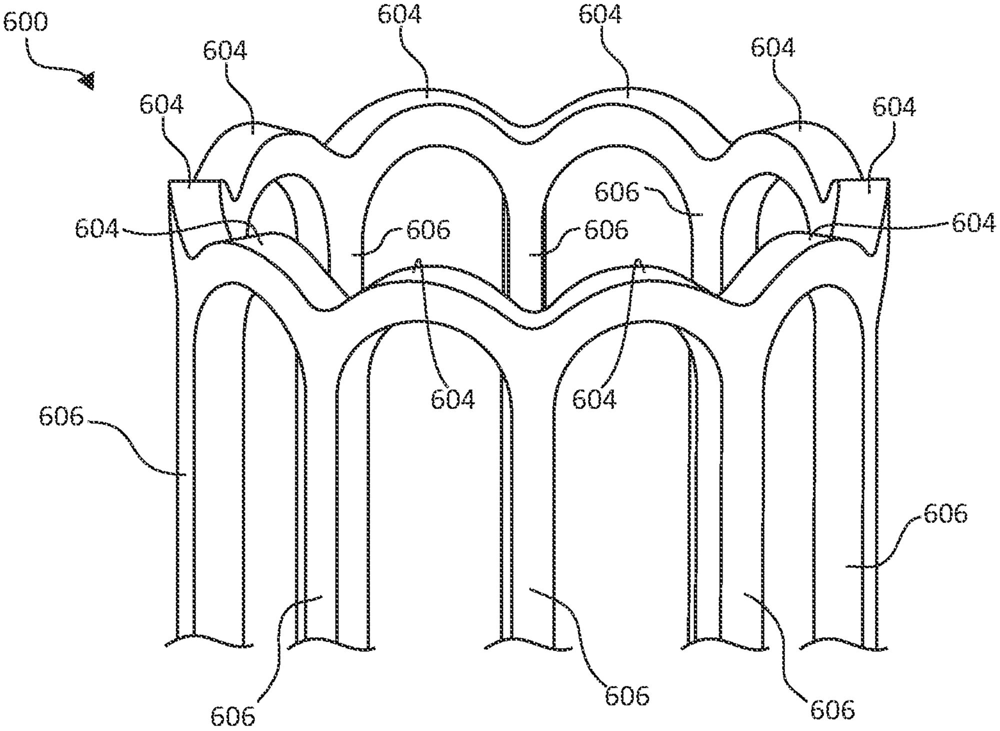
FIG. 6B is a perspective view of the example frame and center frame portion shown in FIG. 6A, prior to flattening and similar to the as-loaded condition in the delivery system in accordance with various aspects of the present disclosure.

The center frame portion 602 and the plurality of elongate members 606 are substantially planar. Forming the frame 600 from a cut tube allows the center frame portion 602 to be substantially flat. In order to arrange the center frame portion 602 and the plurality of elongate members 606 from a tube to a planar configuration, the cut-tube must be flattened from a manufactured configuration as shown in FIG. 6B. As discussed in further detail below, the plurality of arcs 604 may be configured to distribute strain about the center frame portion 602 in transitioning from the manufactured configuration to the flattened configuration as shown in FIG. 6A. The plurality of arcs 604 may be similarly configured to distribute strain about the center frame portion 602 in transitioning the frame 600 from an elongated configuration (e.g., the frame 600 disposed within a delivery system) and a deployed configuration. In the deployed configuration, the portion of the frame 600 shown in FIG. 6A may be a central section of a face portion (e.g., the face portions 220, 300, 400 shown in FIGS. 2-4).

The center frame portion 602 may be configured to attach to a delivery system (e.g., the delivery system discussed in FIGS. 1A-B) for delivering an occlusive device that includes the frame 600 to a target location in a patient. In addition, the frame 600 may be withdrawn into the delivery system by way of the attachment to the center frame portion 602 from the deployed/flattened configuration shown in FIG. 6A, to an elongated configuration within the delivery system. The strains applied to the frame through the transitioning between configurations are distributed by the plurality of arcs 604 about the center frame portion 602.

In addition, the plurality of elongate members 606 may be configured to bend and mitigate movement of the center frame portion 602 and the plurality of elongate members 606 substantially outward from the planar profile shown in FIG. 6A. Although only a portion of the plurality of elongate members 606 is shown in FIG. 6A, the plurality of elongate members 606 may include a curvature to absorb forces that may be applied to portions of the frame 600 (not shown) external to the planar profile of the center frame portion 602 and the plurality of elongate members 606.

FIG. 6B is a perspective view the frame 600 and the center frame portion 602 shown in FIG. 6A, prior to flattening in accordance with various aspects of the present disclosure. The frame 600 is shown in a manufactured configuration after the frame is formed from, for example, a cut-tube or flat-sheet to include the plurality of arcs 604. The plurality of arcs 604 enhance the ability of the frame 600 to flatten into the planar profile shown in FIG. 6A. The plurality of arcs 604 may provide flexibility during the transition of tube to flattened. In addition, the plurality of arcs 604 may transition and distribute the strain that arises from flattening the frame 600 from the manufactured configuration about the center frame portion 602. Stresses accumulate at the peaks or the plurality of arcs 604 and/or at the transitions of the plurality of arcs 604 and the plurality of elongate members 606. The curvature of the plurality of arcs 604 provide an optimized area for the stresses to distribute as compared to a substantially circular or rectangular center area.

In certain instances, the curvature of the plurality of arcs 604 may be reversed from the curvature shown in FIG. 6A. In addition, widths of the plurality of arcs 604 may be equal to widths of the plurality of elongate members 606. In other instances, widths of the plurality of arcs 604 may be between 101% and 160% greater than widths of the plurality of elongate members 606.

The illustrative components shown in FIGS. 6A-B are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 6A-B may be, in embodiments, integrated with various other components depicted therein (and/or components not illustrated), all of which are considered to be within the ambit of the disclosed subject matter. For example, the frame 600 described with reference to FIG. 6A-B may be used in connection with delivery system 20 and form a portion of occlusive device 30, shown in FIGS. 1A-B (e.g., with the plurality of elongate members 606 and the center frame portion 602 forming a portion of the occlusive face 40). In addition, the frame 200 may include a membrane attached thereto (e.g., as shown and discussed with reference to FIG. 7).

Figure 7:
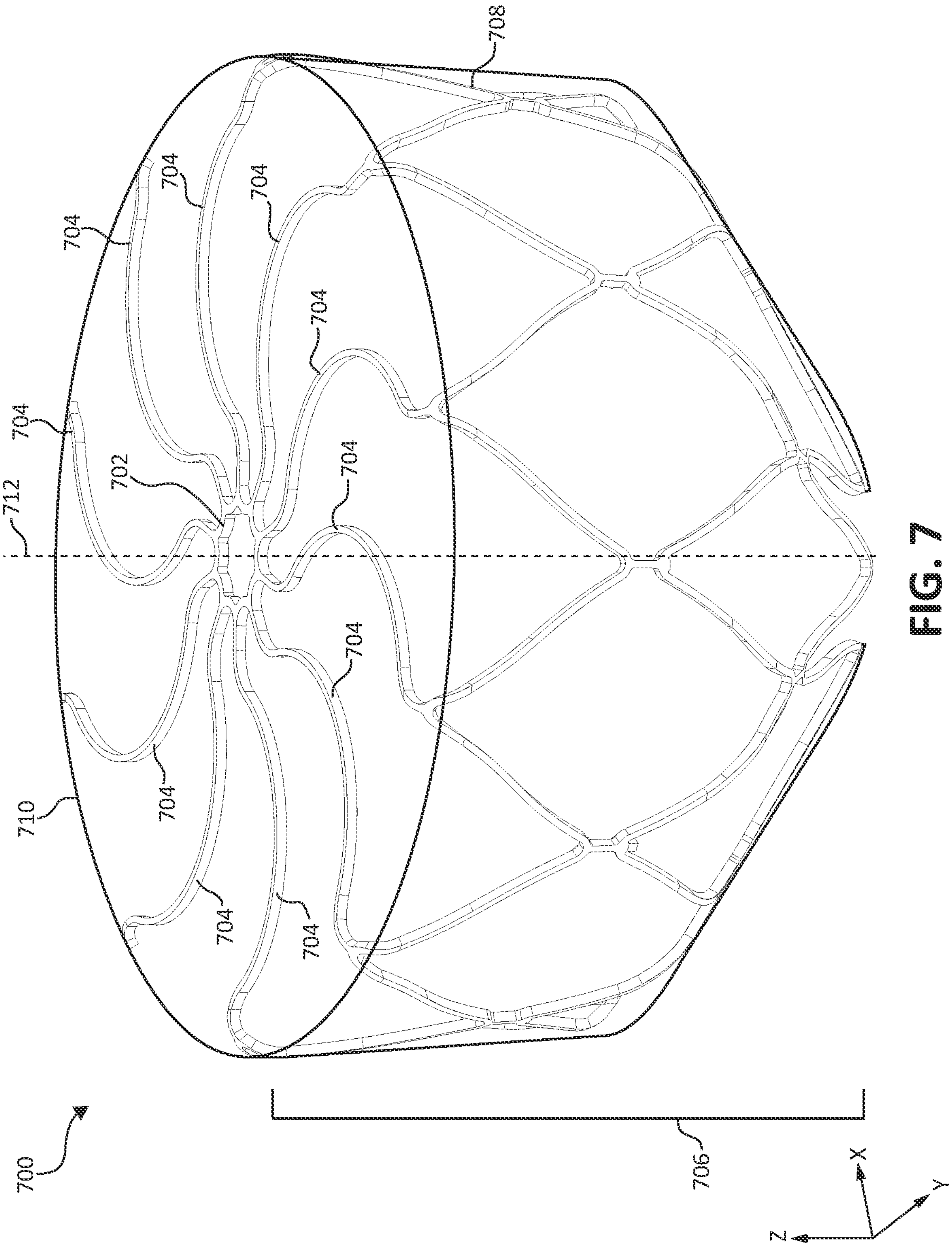
FIG. 7 is a perspective view of an example occlusive device, in accordance with various aspects of the present disclosure.

FIG. 7 is a perspective view of an example occlusive device 700, in accordance with various aspects of the present disclosure. The occlusive device 700 may include a center frame portion 702, a plurality of elongate members 704 that extend from the center frame portion 702, and a body portion 706. The center frame portion 702, the plurality of elongate members 704, and the body portion 706 collectively form a frame 708 of the occlusive device. In certain instances, the frame 708 may be unitary (e.g., formed from a single structure, or a single piece of material) and self-expanding. In addition, the center frame portion 702 and the plurality of elongate members 704 are arranged in a common plane that is orthogonal to a longitudinal axis 712 of the occlusive device 700. The center frame portion 702 and the plurality of elongate members 704 may be within an x-y plane. The body portion 706 of the frame 708, however, may be arranged external to the x-y plane. In certain instances, the plurality of elongate members 704 may bend and mitigate movement of the center frame portion 702 and the plurality of elongate members 704 longitudinally relative to the x-y in response to a compressive force applied to the body portion 706. As shown, the plurality of elongate members 704 include a common curvature that extends from the center frame portion 702 of the frame 708 within the x-y plane.

The occlusive device 700 may also include a membrane arranged on the frame 708. The occlusive device 700, in combination with the center frame portion 702 and the plurality of elongate members 704 (the face portion of the frame 708) may together define an occlusive face of the occlusive device 700. In addition, the center frame portion 702 and the plurality of elongate members 704 being arranged within a common plane may enhance the attachment of the membrane 710 thereto. In certain instances, the center frame portion 702 and the plurality of elongate members may be planar. In addition, the center frame portion 702 and the plurality of elongate members 704 (the face portion of the frame 708) may be a substantially uniform (proximal) surface. The center frame portion 702 and the plurality of elongate members 704 may include an equal and constant surface. In addition, the center frame portion 702 and the plurality of elongate members 704 may be formed without protrusions outward therefrom. In certain instances, the center frame portion 702 and the plurality of elongate members 704 may include approximately equal thickness (relative to y-axis) across the face portion 220. The center frame portion 702 and the plurality of elongate members 704 having a substantially uniform surface or a surface without protrusions outward therefrom may enhance performance of the occlusive device 700 by mitigating the opportunity for thrombus formation.

As shown, the membrane 710 may cover the center frame portion 702. The center frame portion 702 may be an aperture in the frame 708 (e.g., as shown in FIGS. 2-4 and 6A). The membrane 710 may cover or partially cover the center frame portion 702 to seal off the face portion of the frame 708. The membrane 710 may partially extend within the center frame portion 702 to provide sealing. In addition, the membrane 710 may be attached to the external portion of the frame 700 to entirely cover the frame 700 (e.g., such that the frame 700, which may be composed of nitinol, is not exposed to blood or tissue in situ).

As noted above, the plurality of elongate members 704 may be configured to bend and mitigate movement of the center frame portion 702 and the plurality of elongate members 704 longitudinally in response to a compressive force applied to the body portion 706. When the occlusive device 700 is implanted in a patient, the plurality of elongate members 704 may facilitate the ability of the frame 708 to adapt and conform to irregular tissue topographies and/or dynamically variable tissue topographies. Forces may be applied from the tissue topography and directed to one or more locations on the body portion 706. In certain instances, this force is directed along a length of the body portion 706 toward the plurality of elongate members 704, and the plurality of elongate members 704 deform and absorb the applied force(s), and balance and/or share the applied force(s) throughout the frame 708. In certain instances, the occlusive device 700 may be positioned within a left atrial appendage to help prevent thrombus from embolizing from the left atrial appendage (e.g., as shown above in FIG. 1B). After implantation, the occlusive device 700 conforms to the left atrial appendage, and forces that are applied via the left atrial appendage may be absorbed by the plurality of elongate members 704. The plurality of elongate members 704 maintain a planar occlusive face in a common plane on opposite sides of an ostium of the left atrial appendage. The bending of the plurality of elongate members 704, in response to forces applied to the body portion 706, maintain a substantially uniform surface (substantially planar and/or without protrusions) and close off the ostium to help prevent thrombus from embolizing from the left atrial appendage and without disrupting blood flow along the occlusive face.

The center frame portion 702 and the plurality of elongate members 704 being arranged and the flex or bend being maintained within a common plane (e.g., planar) orthogonal to the longitudinal axis 712 may provide structural stability for the membrane 710 when the occlusive device 700 is implanted. As noted above, thrombus may occur along the face of the occlusive device 700 due to a non-uniform surface altering the blood flow. As noted above, the center frame portion 702 and the plurality of elongate members 704 may be uniform and not include protrusions. The lack of protrusions may also enhance the mitigation of thrombosis by not altering the blood flow. Thus, a patient may remain susceptible to blood coagulation and thrombus formation if an occlusive device does not maintain a planar and/or uniform face. If a frame that supports a membrane does not include a planar face and/or uniform face, the membrane may conform to the non-planar face and/or non-uniform face and provide a device that has a non-uniform surface or a face that includes protrusions, which may alter blood flow thereacross. As a result, the center frame portion 702 and the plurality of elongate members 704 may enhance structural stability of the membrane 710, and maintain a planar and/or uniform occlusive face for the occlusive device 700.

In embodiments, a biocompatible material for the membrane is used. In certain embodiments, the membrane 710 may include a fluoropolymer, such as a polytetrafluoroethylene (PTFE) polymer or an expanded polytetrafluoroethylene (ePTFE) polymer. In some embodiments, the membrane 710 may be formed of a polyester, a silicone, a urethane, a polyethylene terephthalate, or another biocompatible polymer, or combinations thereof. In some embodiments, bioresorbable or bioabsorbable materials may be used, for example a bioresorbable or bioabsorbable polymer. In some embodiments, the membrane 710 can comprise a fluoropolymer, such as described in one or more of U.S. Pat. Nos. 7,049,380; 7,462,675; and 8,048,440, the contents of which are each incorporated by reference herein. In some embodiments, the membrane 710 can comprise Dacron, polyolefins, carboxy methylcellulose fabrics, polyurethanes, or other woven or film elastomers. In some embodiments, the membrane 710 can comprise knits or fibers. The membrane 710 may be woven or non-woven in various embodiments including wires for example. In some embodiments, the membrane 710 may be formed of a copolymer of fluoropolymers or blends thereof.

In some embodiments, the membrane 710 is configured to inhibit, filter, modulate, or substantially modulate the passage of fluids and/or materials (such as blood and/or thrombus) through the membrane 710. In some embodiments, the membrane 710 is configured to induce rapid tissue ingrowth therein. In an embodiment, the membrane 710 provides for a blood or body fluid impermeable membrane that occludes the flow of blood or bodily fluids through the membrane yet promotes the ingrowth and endothelialization. The membrane 710 can have a microporous structure that provides a tissue ingrowth scaffold for durable occlusion and supplemental anchoring strength of the occlusive device 700. In some embodiments, the membrane 710 is a porous member. Pores of the membrane 710 may be sized to substantially, or in some examples completely, help prevent passage of blood, other bodily fluids, and emboli. In some implementations, the membrane 710 prevents or substantially prevents passage of blood, other bodily fluids, thrombi, emboli, or other bodily materials through the membrane 710.

In some embodiments, the membrane 710 is configured such that the desired modulation of fluid and/or blood component passage through the membrane 710 is immediate and does not rely on a thrombotic process. In some embodiments, the membrane 710 can be modified by one or more chemical or physical processes that enhance certain physical properties of the membrane 710. For example, a hydrophilic coating may be applied to the membrane 710 to improve the wettability and echo translucency of the membrane 710. In some embodiments, the membrane 710 may be modified with chemical moieties that promote one or more of endothelial cell attachment, endothelial cell migration, endothelial cell proliferation, and resistance to thrombosis. In some embodiments, the membrane 710 may be modified with covalently attached heparin or impregnated with one or more drug substances that are released in situ to promote wound healing or reduce tissue inflammation. In some embodiments, the drug may be a corticosteroid, a human growth factor, an anti-mitotic agent, an antithrombotic agent, or dexamethasone sodium phosphate.

In some embodiments, the membrane 710 is pre-perforated to modulate fluid flow through the membrane 710, to create filtering properties, and/or to affect the propensity for tissue ingrowth to the membrane 710. In some embodiments, portions or all of the membrane 710 are treated to make the membrane 710 elastic. For example, in some embodiments, the membrane is treated with silicone or elastic fluoropolymers to provide elasticity to portions or all of the membrane 710. In some embodiments, the membrane 710 is treated to make the membrane 710 stiffer or to add surface texture. For example, in some embodiments the membrane 710 is treated with fluorinated ethylene propylene (FEP) to provide a stiffened membrane 710 or roughened surface on the membrane 710. Other membrane 710 material treatment techniques can also be employed to provide beneficial mechanical properties and tissue response interactions. Such materials and techniques can be used for any of the occlusive devices provided herein.

In the certain embodiments, the membrane 710 conforms to the contours of the frame 708. In some embodiments the membrane 710 may be attached to an outer periphery of the frame 708 and suspended therebetween (like a drum skin).

In some embodiments, the membrane 710 is attached to selected regions of the frame 708 and not attached to other regions of the frame 708. This technique can facilitate enhanced conformability of the occlusive device 700 to the topography of a patient's anatomy at the implant site, and/or enhanced catheter loading in some embodiments. In other embodiments the membrane 710 is attached to all portions of the frame 708. In some embodiments, the membrane 710 may include pleats, folds, crimps, openings, corrugations, and the like. In other embodiments pleats, folds, or the like on the membrane 710 are avoided on the center frame portion 702 and the plurality of elongate members 704, as a result of the uniform surface thereof, which may minimizes blood flow disruptions thereacross. In some embodiments, the membrane 710 is an elastic member that can elastically stretch and retract to accommodate the expandability and loadability of the frame 708. Such features and techniques can also be incorporated with other embodiments of occlusive devices provided herein.

In some embodiments, the membrane 710 is attached to the frame 708 using an adhesive. In some embodiments, FEP is used as an adhesive to attach the membrane 710 to the frame 708, or portions thereof. For example, an FEP coating can be applied to some or all portions of the frame 708, and the FEP can act as a bonding agent to adhere the membrane 710 to the frame 708.

The illustrative components shown in FIG. 7 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 7 may be, in embodiments, integrated with various other components depicted therein (and/or components not illustrated), all of which are considered to be within the ambit of the disclosed subject matter. For example, the occlusive device 700 described with reference to FIG. 7 may be used in connection with delivery system 20 (shown in FIGS. 1A-B) in place of the occlusive device 30. In addition, the center frame portion 702 and the plurality of elongate members 704 may be replaced with the center frame portion and the plurality of elongate members as described with reference to FIGS. 2-4. In addition the occlusive device 700 may include anchors (e.g., as shown in FIGS. 5A-B). Further yet, the center frame portion 702 may be replaced with the center frame portion 602 as shown in FIGS. 6A-B.

FIG. 8 is a perspective view of another example frame 800 for an occlusive device, in accordance with various aspects of the present disclosure. The frame 800 may include a center frame portion 802 and a plurality of elongate members 804. The center frame portion 802 and the plurality of elongate members 804 are arranged within a common plane that is perpendicular to a longitudinal axis (not illustrated) of the frame 800.

The frame 800 also includes a portion 806 that is non-planar with respect to the center frame portion 802 and the plurality of elongate members 804. The plurality of elongate members 804 may include a common formation. As shown, the plurality of elongate members 804 include a zig-zag pattern that act as a spring element and absorb and distributes forces that are applied to the frame 800. The plurality of elongate members 804 may enhance fatigue resistance of the frame 800 by functioning as stress relief features that absorb displacement, flexure and/or torque, and the like, in response to a force being applied to the frame 800. The plurality of elongate members 804 are configured to bend within the common plane to mitigate movement of the center frame portion 802 and the plurality of elongate members 804 in the longitudinal plane in response to a force applied to frame 800.

Figure 9A:
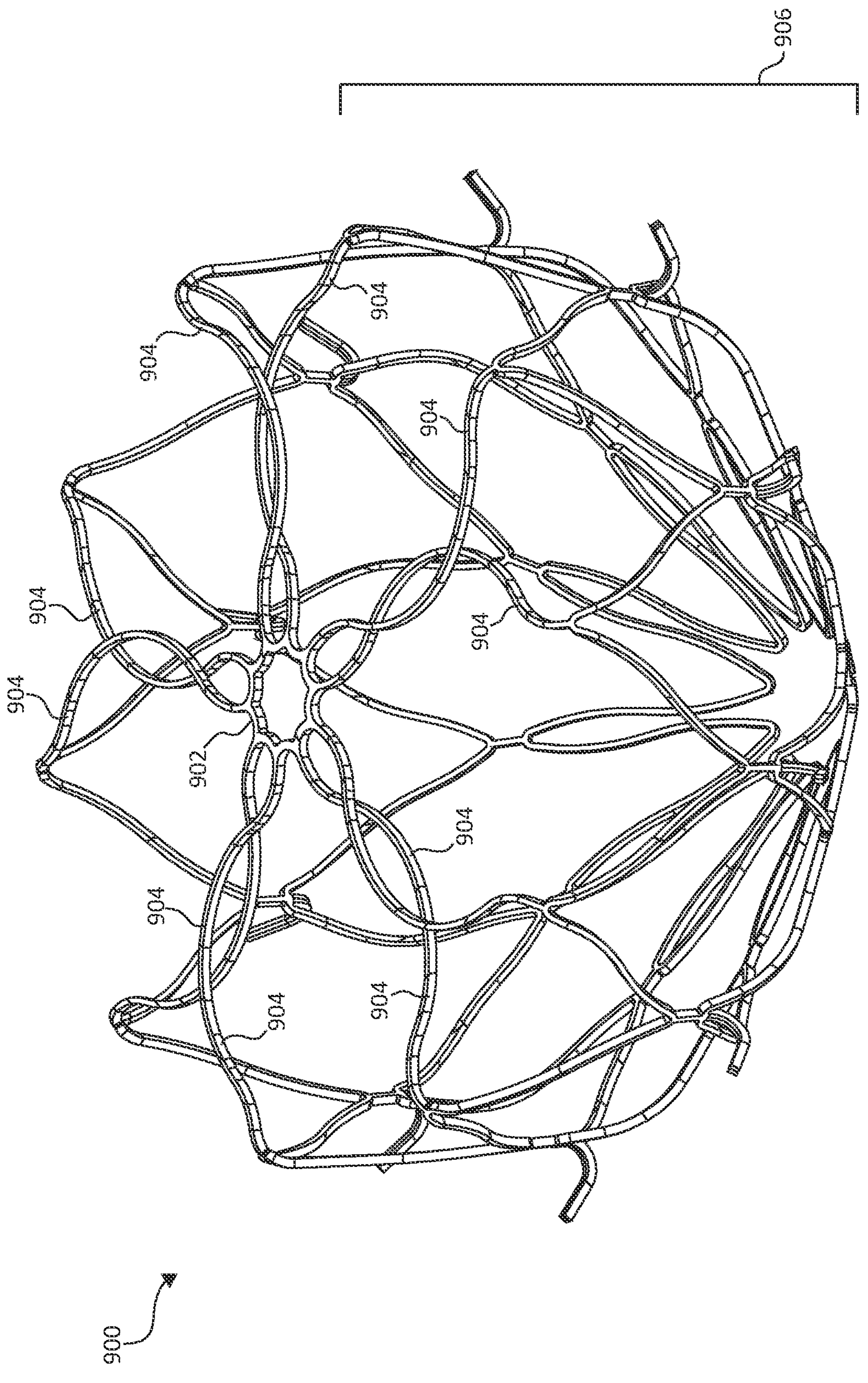
FIG. 9A is a perspective view of another example frame for an occlusive device in a shape set configuration, in accordance with various aspects of the present disclosure.

FIG. 9A is a perspective view of another example frame 900 for an occlusive device in a shape set configuration, in accordance with various aspects of the present disclosure. The frame 900 may include a center frame portion 902 and a plurality of elongate members 904. The center frame portion 902 and the plurality of elongate members 904 are arranged within a common plane that is perpendicular to a longitudinal axis (not illustrated) of the frame 900. As shown in FIG. 9A, adjacent elongate members 904 of the plurality of elongate members 904 are overlapping. The plurality of elongate members 904 each include curvatures such that the plurality of elongate members 904 form common curvatures to provide the overlapping pattern shown. The center frame portion 902 and the plurality of elongate members 904 may be considered to be arranged within the common plane, with the common plane being bounded by a thickness of the center frame portion 902 and the plurality of elongate members 904 forming a face of the frame 900.

The frame 900 also includes a body portion 906 that is non-planar with respect to the center frame portion 902 and the plurality of elongate members 904. The body portion 906 may extend from the plurality of elongate members 904. The plurality of elongate members 904 may act as a spring element and absorb forces that are applied to the frame 900. The plurality of elongate members 904 may enhance fatigue resistance of the frame 900 by functioning as stress relief features that absorb displacement, flexure and/or torque, and the like, in response to a force being applied to the frame 900. The plurality of elongate members 904 are configured to bend within the common plane mitigate movement of the center frame portion 902 and the plurality of elongate members 904 longitudinally in response to a force applied to frame 900.

Figure 9B:
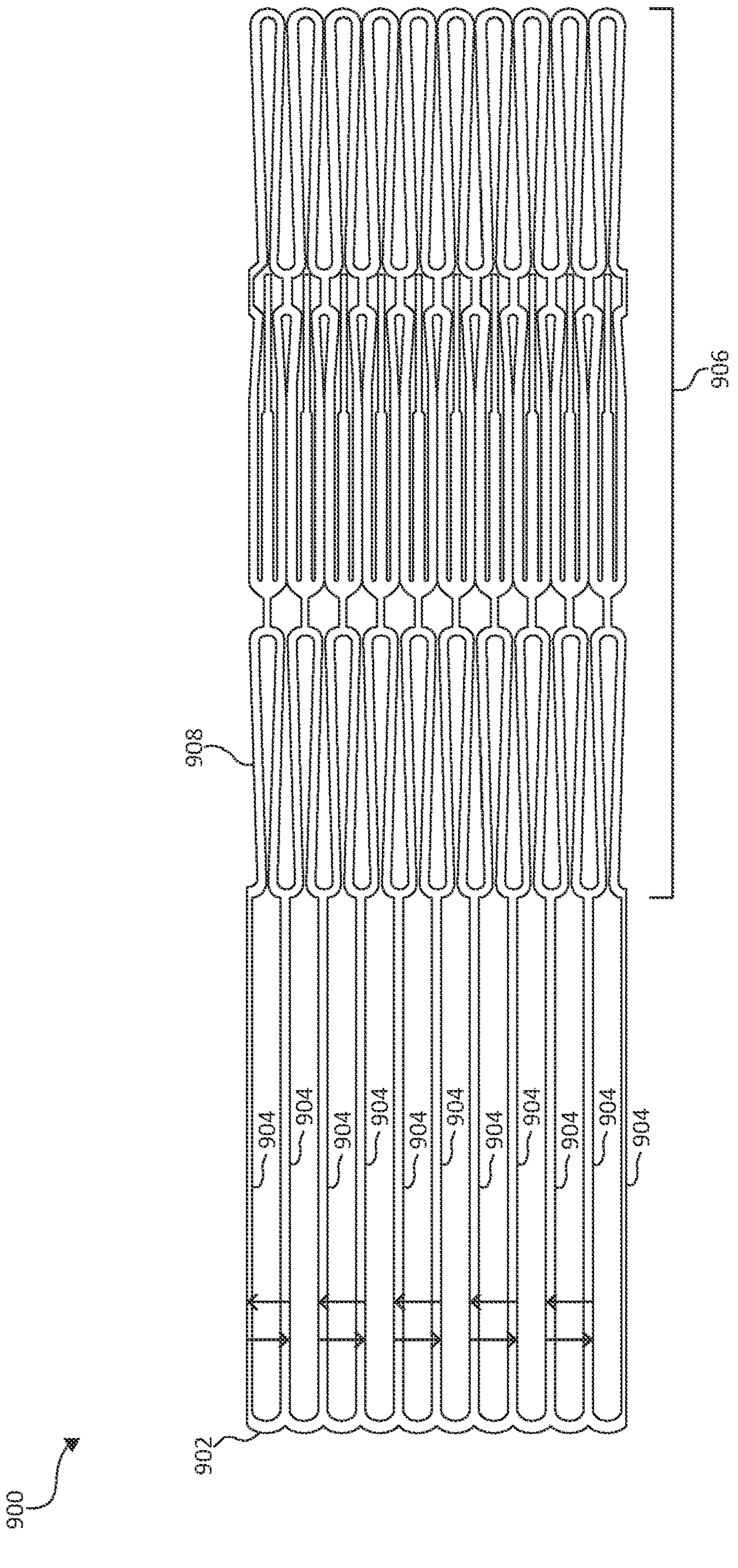
FIG. 9B is a side view of a strut cut pattern of the frame, shown in FIG. 9A, prior to deformation to the shape set configuration, in accordance with various aspects of the present disclosure.

FIG. 9B is a side view of a strut cut pattern 908 of the frame 900, shown in FIG. 9A, prior to deformation to the shape set configuration, in accordance with various aspects of the present disclosure. Prior to forming the frame 900 into the shape set configuration shown in FIG. 9A, the strut cut pattern 908 may be formed by laser cutting a tube. As shown in FIG. 9B, the strut cut pattern 908 includes the center frame portion 902, the plurality of elongate members 904, and the body portion 906. In shaping the strut cut pattern 908 into the configuration shown in FIG. 9A, the body portion 906 may be arranged into an acorn-like shape, and adjacent sets of the plurality of elongate members 904 are overlaid with one another to form as illustrated by the arrows in FIG. 9B.

Figure 10:
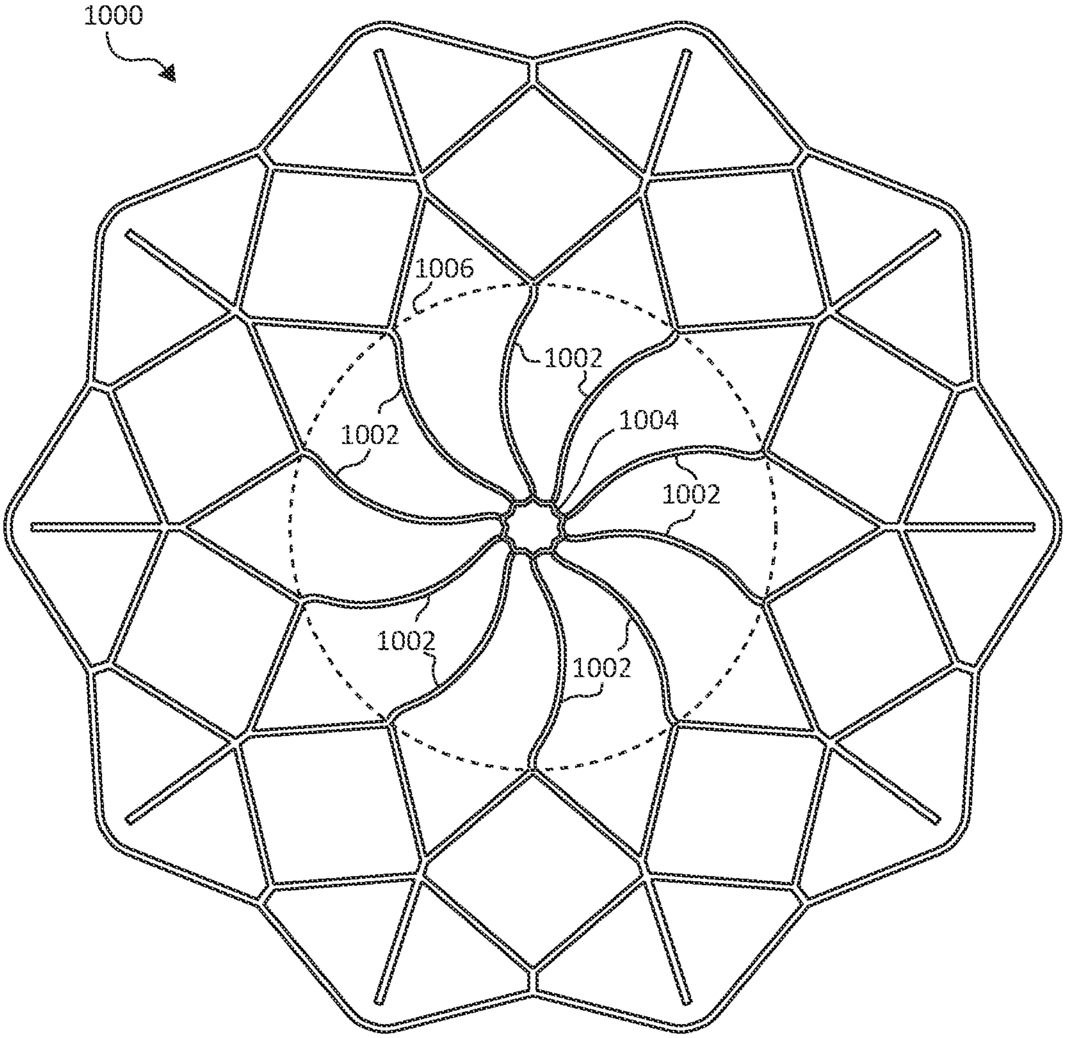
FIG. 10 is example flat pattern that can be used for forming a sheet material to create a frame of an occlusive device, in accordance with various aspects of the present disclosure.

FIG. 10 is an example flat pattern 1000 that can be used for forming a sheet material to create a frame of an occlusive device, in accordance with various aspects of the present disclosure. A nitinol sheet material may be utilized. Pattern 1000 results in occlusive device frames with no protuberances related to a center frame portion 1004 from the outer surface of the frames. The flat pattern 1000 can also be used to form a plurality of elongate members with curved portions corresponding to material portions 1002 of pattern 1000. A boundary 1006 shown in FIG. 10 may correspond to a boundary of a face portion of the frame of an occlusive device.

The flat pattern 1000 of FIG. 10, for example, can be used to form a plurality of elongate members corresponding to material portions 1002 of pattern 1000 that include curved portions (and other non-linear shapes). Such curved portions may be directed to enhancing fatigue resistance by providing elements such as, but not limited to, stress relief features, portions designed to absorb displacement, flexure and/or torque, and the like, and combinations of such features. The flat pattern 1000 can also be used to form an occlusive device frame. Hence, it can be appreciated that by cutting a sheet material using a flat pattern, and by using the techniques described above, a wide variety of occlusive device frame design features are attainable.

Figure 11:
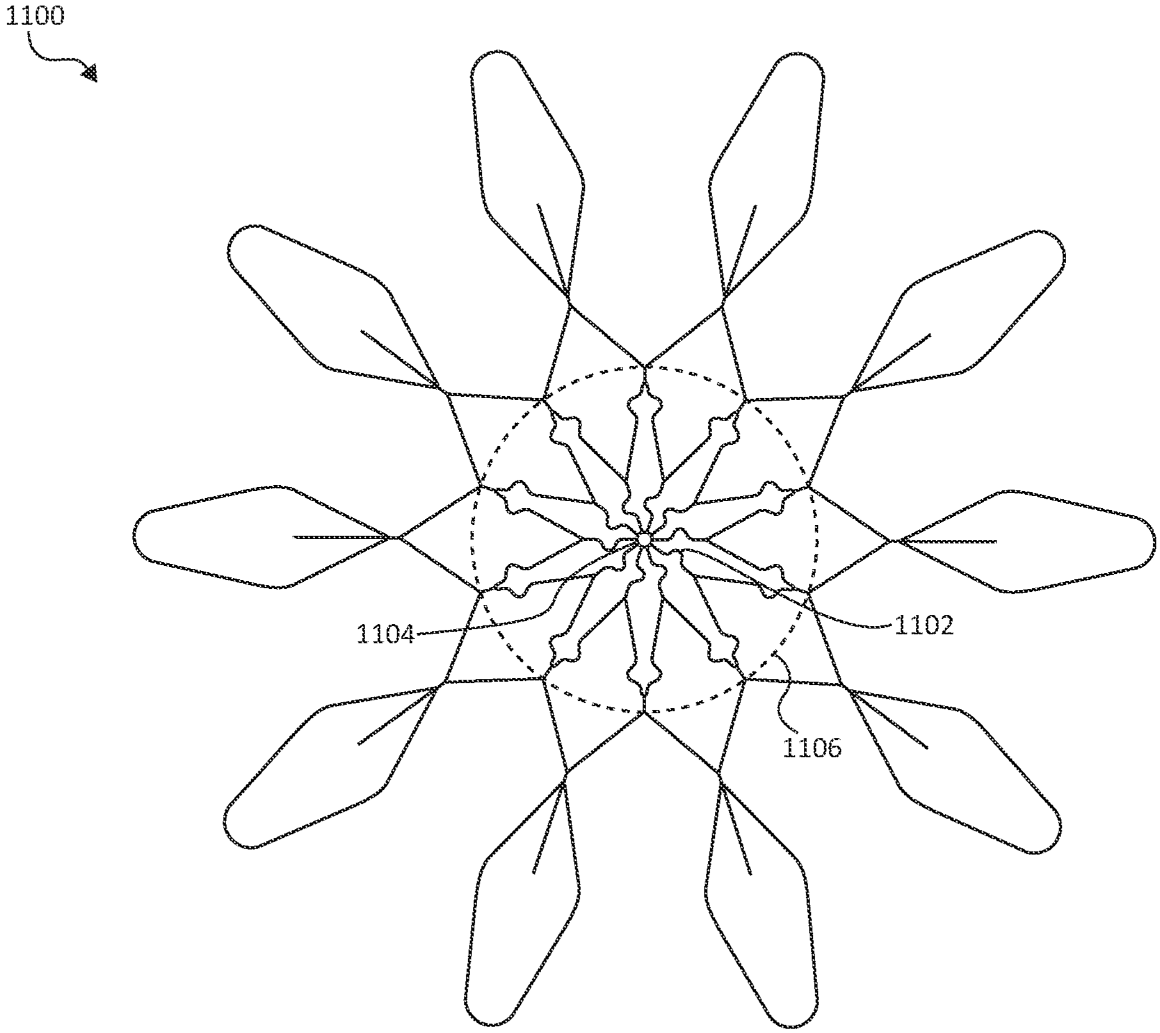
FIG. 11 is another example flat pattern that can be used for forming a sheet material to create a frame of an occlusive device, in accordance with various aspects of the present disclosure.

FIG. 11 is another example flat pattern 1100 that can be used for forming a sheet material to create a frame of an occlusive device, in accordance with various aspects of the present disclosure. Pattern 1100 results in occlusive device frames with no protuberances related to a center frame portion 1104 from the outer surface of the frames. The flat pattern 1100 can also be used to form branch elongate members with curved portions corresponding to material portions 1102 of pattern 1100. A boundary 1106 shown in FIG. 10 may correspond to a boundary of a face portion of the frame of an occlusive device.

The flat pattern 1100 of FIG. 11, for example, can be used to form a plurality of elongate members corresponding to portions of pattern 1100 that include wavy portions (and other non-linear shapes). Such wavy portions may be directed to enhancing fatigue resistance by providing elements such as, but not limited to, stress relief features, portions designed to absorb displacement, flexure and/or torque, and the like, and combinations of such features. Hence, it can be appreciated that by cutting a sheet material using a flat pattern, and by using the techniques described above, a wide variety of occlusive device frame design features are attainable.

Figure 12:
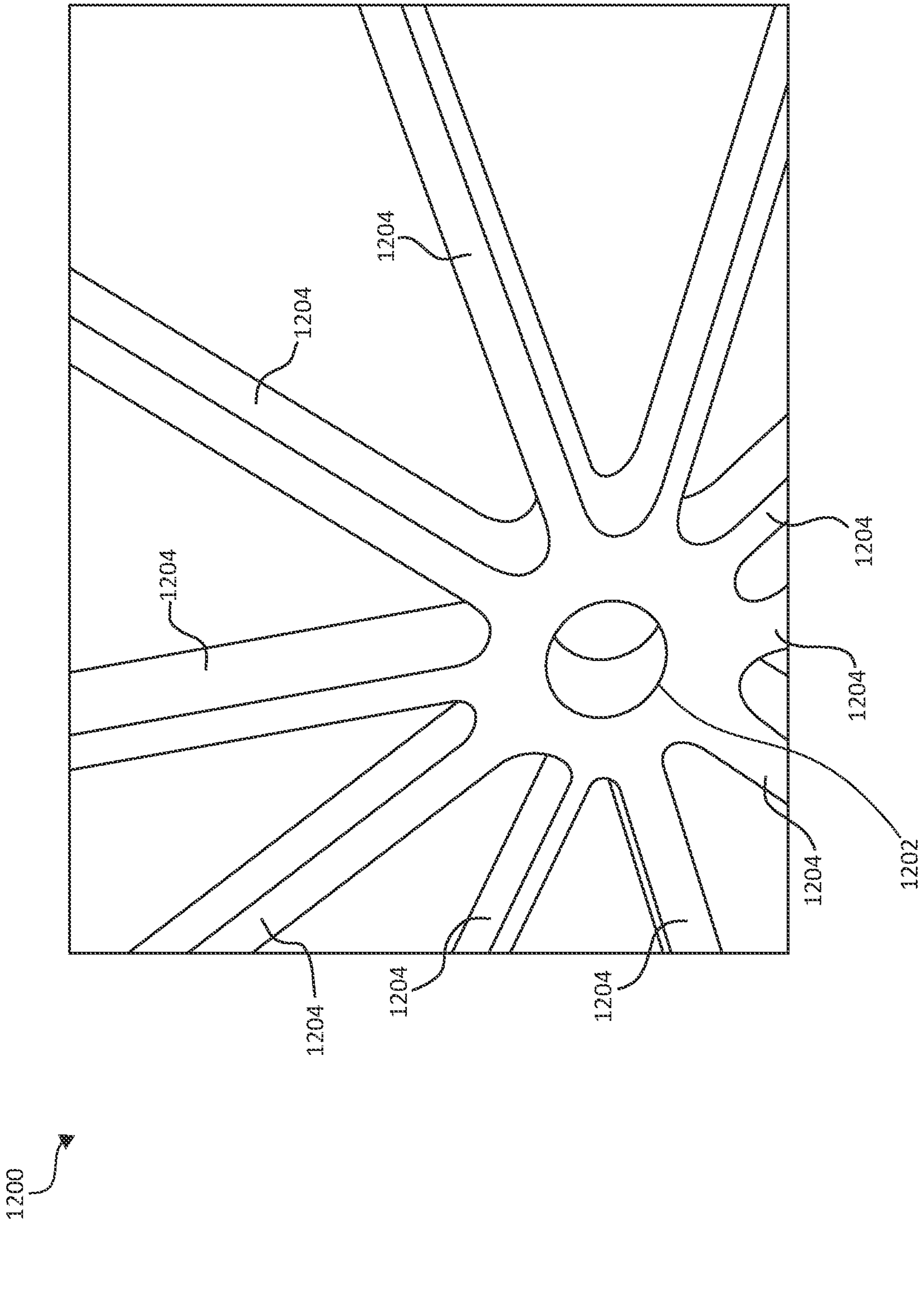
FIG. 12 is a top view of an example center frame portion that may be included with an occlusive device, in accordance with various aspects of the present disclosure.

FIG. 12 is a top view of an example center frame portion 1202 that may be included with an occlusive device, in accordance with various aspects of the present disclosure. The center frame portion 1202 does not protrude from the outer surface defined by the frame 1200. Rather, the frame material that defines the center frame portion 1202 is flush with the outer surface defined by the frame 1200. In certain instances and as shown, the center frame portion 1202 is a hole having an inner and outer circumference and a plurality of elongate members 1204 radiate outward from the outer circumference of the center frame portion 1202. Accordingly, the frame 1200 includes the center frame portion 1202 while not initiating or contributing to the potential for in situ flow disruptions and/or thrombus formation.

In some embodiments, the center frame portion 1202 provides an attachment location that a delivery and/or retrieval device (e.g., a catheter and the like) can use to releasably couple with the frame 1200. In some embodiments, the center frame portion 1202 defines a round through-hole (as shown). In some embodiments, the center frame portion 1202 defines structural features having a different shape such as, but not limited to, ovular, square, rectangular, triangular, key-hole shaped, reniform, and the like, and combinations thereof. In some embodiments, the center frame portion 1202 can include or define threads, one or more keyways, tabs, deformable elements, and the like, and combinations thereof.

In some embodiments, additional structure on the internal side of the frame 1200 can be added in the region of the center frame portion 1202 that can be used for releasable attachment with a delivery and/or retrieval device. For example, a collar (or other physical member, e.g., a coiled member, a socket, screw fitting, etc.) can be included that extends distally from the center frame portion 1202 into what is, or will be, the interior of the frame 1200 while maintaining a uniform external surface of the frame 1200. Such a collar can have various physical shapes and features as desired to facilitate releasable attachment with a delivery and/or retrieval device. In some embodiments, no through-hole is included as part of the occlusive device frame 1200. Such features and techniques can also be incorporated with other embodiments of occlusive devices provided herein.

The illustrative components shown in FIGS. 13-18 are not intended to suggest any limitation as to the scope of use or functionality of embodiments of the disclosed subject matter. FIGS. 13-18 describe and show alternate body portions that may be arranged with one or more of the face portions described above (e.g., face portions 220, 300, 400, 502*a*, 502*b*). Neither should the illustrative components be interpreted as having any dependency or requirement related to any single component or combination of components illustrated therein. Additionally, any one or more of the components depicted in any of FIGS. 13-18 may be, in embodiments, integrated with various other components depicted therein (and/or components not illustrated), all of which are considered to be within the ambit of the disclosed subject matter.

Figure 13:
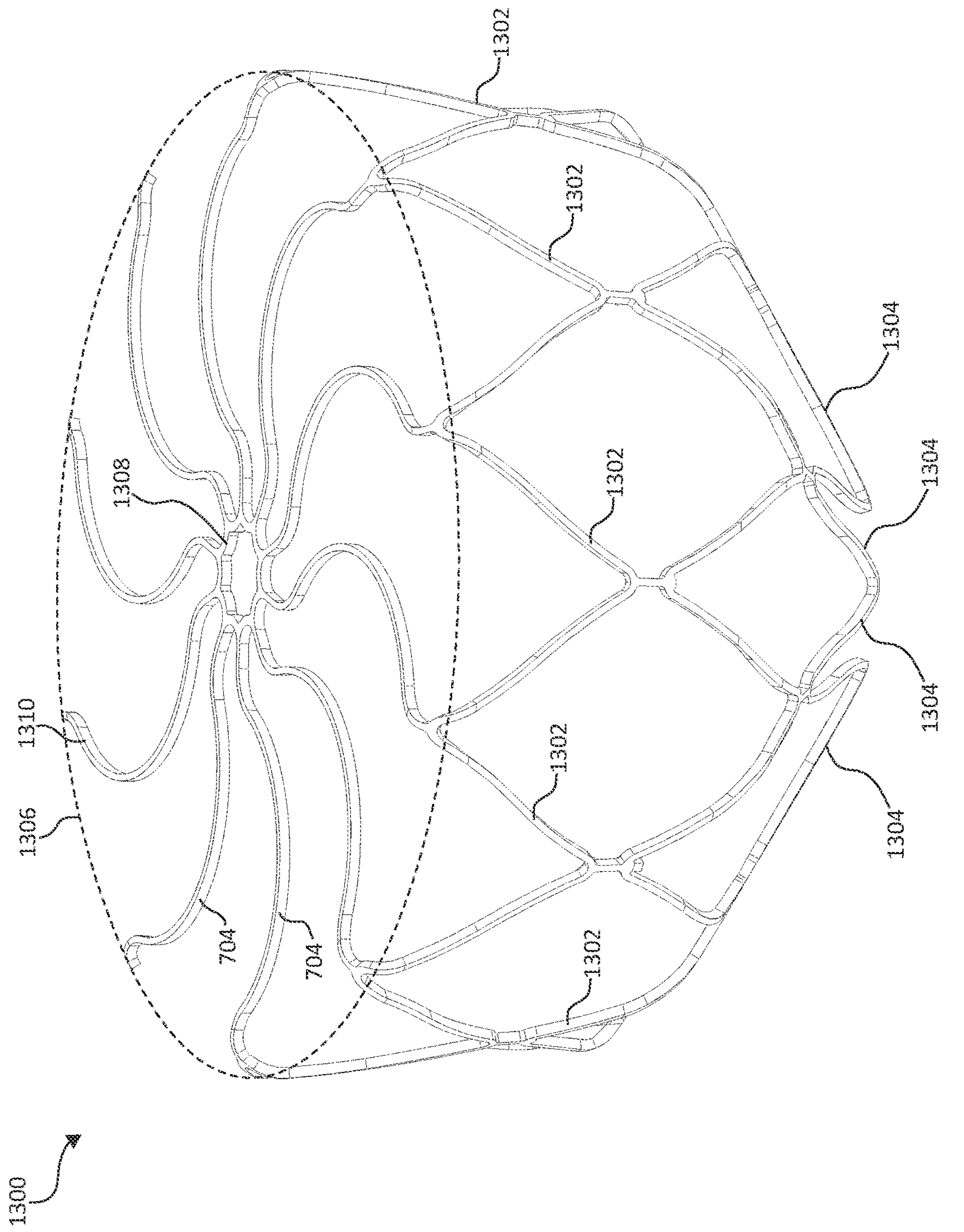
FIG. 13 is a perspective view of an alternate design of an example frame for an occlusive device, in accordance with various aspects of the present disclosure.

FIG. 13 is a perspective view of an alternate design of an example frame 1300 for an occlusive device, in accordance with various aspects of the present disclosure. The frame 1300 includes a first set of cells 1302 and a second set of cells 1304. The first set of cells 1302 and the second set of cells 1304 may be substantially diamond shaped. In addition and as shown, the first set of cells 1302 and the second set of cells 1304 may longitudinally overlap with one another to form the frame 1300. The first set of cells 1302 and the second set of cells 1304 may include equal areas, or one of the first set of cells 1302 and the second set of cells 1304 may be greater in area than the other of the first set of cells 1302 and the second set of cells 1304.

The frame 1300 may also include a face portion 1306. The face portion 1306 may include a center frame portion 1308 and a plurality of elongate members 1310. As discussed above in detail with reference to FIGS. 2-5, the plurality of elongate members 1310 may enhance fatigue resistance of the frame 1300 by functioning as stress relief features that absorb displacement, flexure and/or torque, and the like, in response to a force being applied to the first set of cells 1302 and/or the second set of cells 1304. Thus, the plurality of elongate members 1310 may be configured to configured to flex or bend substantially within plane, in which the plurality of elongate members 1310 and the center frame portion 1308 are arranged, to mitigate longitudinal movement of the face portion 1306 substantially outward from the plane in response to a force applied to the first set of cells 1302 and/or the second set of cells 1304.

The illustrative components shown in FIG. 13 are not intended to suggest any limitation as to the scope of use or functionality of embodiments of the disclosed subject matter. Neither should the illustrative components be interpreted as having any dependency or requirement related to any single component or combination of components illustrated therein. In certain instances, for example, face portions 220, 300, 400, 502*a* or 502*b* may be incorporated in place of the face portion 1306.

Figure 14:
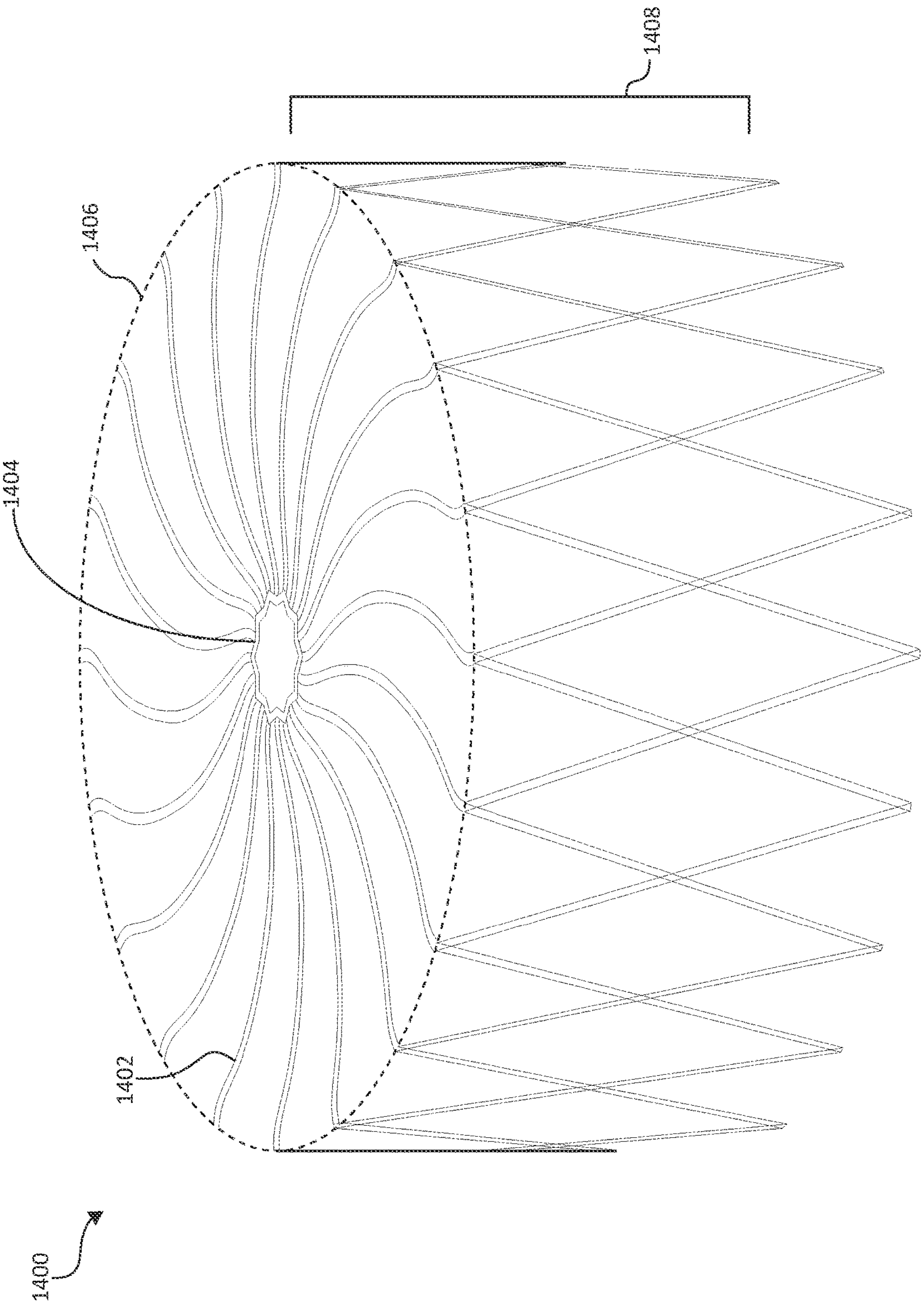
FIG. 14 is a perspective view of an alternate design of another example frame for an occlusive device, in accordance with various aspects of the present disclosure.

FIG. 14 is a perspective view of an alternate design of another example frame 1400 for an occlusive device, in accordance with various aspects of the present disclosure. The frame 1400 may include a body portion 1408 and a face portion 1406 that is used to block off the target location into which the body portion 1408 is implanted. As shown, the body portion 1408 may be formed by a plurality of struts or wires that are interwoven together.

The face portion 1406 may include a center frame portion 1404 and a plurality of elongate members 1402. As discussed above in detail with reference to FIGS. 2-5, the plurality of elongate members 1402 may enhance fatigue resistance of the frame 1400 by functioning as stress relief features that absorb displacement, flexure and/or torque, and the like, in response to a force being applied to the body portion 1408. Thus, the plurality of elongate members 1402 may be configured to configured to flex or bend substantially within plane, in which the plurality of elongate members 1402 and the center frame portion 1404 are arranged, to mitigate longitudinal movement of the face portion 1406 substantially outward from the plane in response to a force applied to one or more portions of the body portion 1408.

The illustrative components shown in FIG. 14 are not intended to suggest any limitation as to the scope of use or functionality of embodiments of the disclosed subject matter. Neither should the illustrative components be interpreted as having any dependency or requirement related to any single component or combination of components illustrated therein. In certain instances, for example, face portions 220, 300, 400, 502*a* or 502*b* may be incorporated in place of the face portion 1406.

Figure 15:
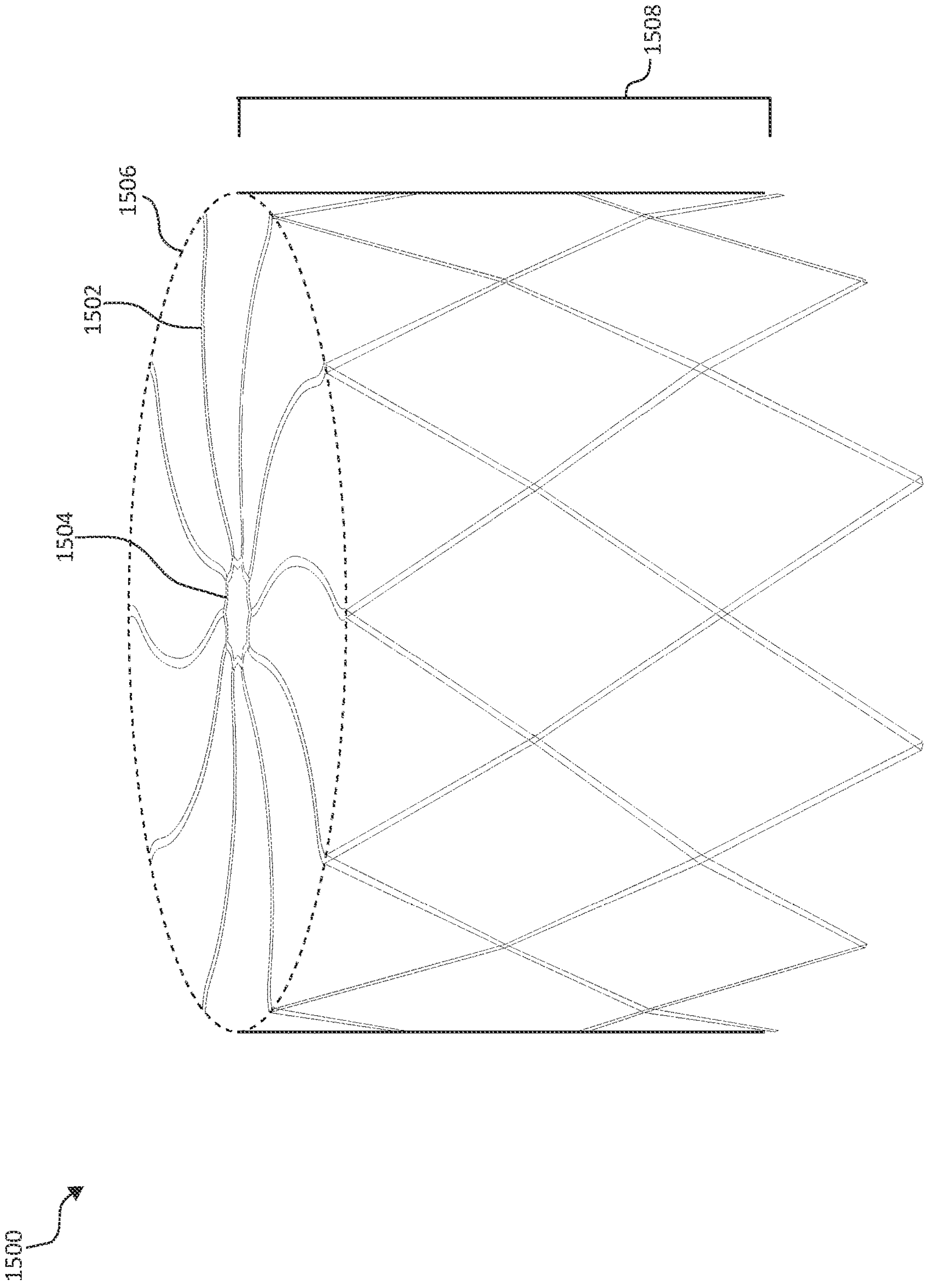
FIG. 15 is a perspective view of an alternate design of another example frame for an occlusive device, in accordance with various aspects of the present disclosure.

FIG. 15 is a perspective view of an alternate design of another example frame 1500 for an occlusive device, in accordance with various aspects of the present disclosure. The frame 1500 may include a body portion 1508 and a face portion 1506 that is used to block off the target location into which the body portion 1508 is implanted. As shown, the body portion 1508 may be a cylindrical shape formed by a plurality of struts or wires with diamond shaped cells that include approximately equal areas.

The face portion 1506 may include a center frame portion 1504 and a plurality of elongate members 1502. As discussed above in detail with reference to FIGS. 2-5, the plurality of elongate members 1502 may enhance fatigue resistance of the frame 1500 by functioning as stress relief features that absorb displacement, flexure and/or torque, and the like, in response to a force being applied to the body portion 1508. Thus, the plurality of elongate members 1502 may be configured to configured to flex or bend substantially within plane, in which the plurality of elongate members 1502 and the center frame portion 1504 are arranged, to mitigate longitudinal movement of the face portion 1506 substantially outward from the plane in response to a force applied to one or more portions of the body portion 1508.

The illustrative components shown in FIG. 15 are not intended to suggest any limitation as to the scope of use or functionality of embodiments of the disclosed subject matter. Neither should the illustrative components be interpreted as having any dependency or requirement related to any single component or combination of components illustrated therein. In certain instances, for example, face portions 220, 300, 400, 502*a* or 502*b* may be incorporated in place of the face portion 1506.

Figure 16:
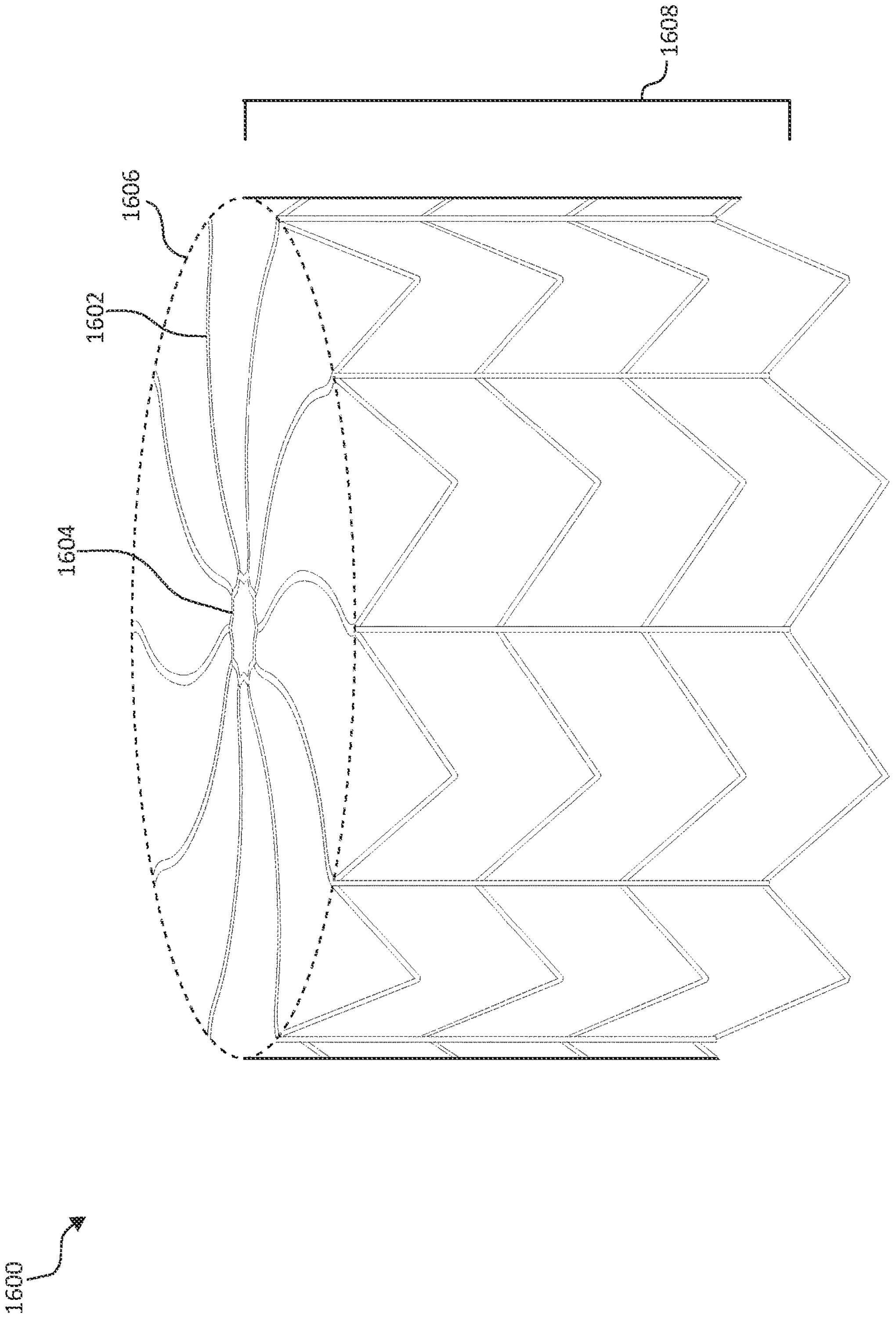
FIG. 16 is a perspective view of an alternate design of another example frame for an occlusive device, in accordance with various aspects of the present disclosure.

FIG. 16 is a perspective view of an alternate design of another example frame 1600 for an occlusive device, in accordance with various aspects of the present disclosure. The frame 1600 may include a body portion 1608 and a face portion 1606 that is used to block off the target location into which the body portion 1608 is implanted. As shown, the body portion 1608 may be a cylindrical shape formed by a plurality of struts or wires with a plurality of rows having zig-zag formation around a circumference of the body portion 1608.

The face portion 1606 may include a center frame portion 1604 and a plurality of elongate members 1602. As discussed above in detail with reference to FIGS. 2-5, the plurality of elongate members 1602 may enhance fatigue resistance of the frame 1600 by functioning as stress relief features that absorb displacement, flexure and/or torque, and the like, in response to a force being applied to the body portion 1608. Thus, the plurality of elongate members 1602 may be configured to configured to flex or bend substantially within plane, in which the plurality of elongate members 1602 and the center frame portion 1604 are arranged, to mitigate longitudinal movement of the face portion 1606 substantially outward from the plane in response to a force applied to one or more portions of the body portion 1608.

The illustrative components shown in FIG. 16 are not intended to suggest any limitation as to the scope of use or functionality of embodiments of the disclosed subject matter. Neither should the illustrative components be interpreted as having any dependency or requirement related to any single component or combination of components illustrated therein. In certain instances, for example, face portions 220, 300, 400, 502*a* or 502*b* may be incorporated in place of the face portion 1606.

Figure 17:
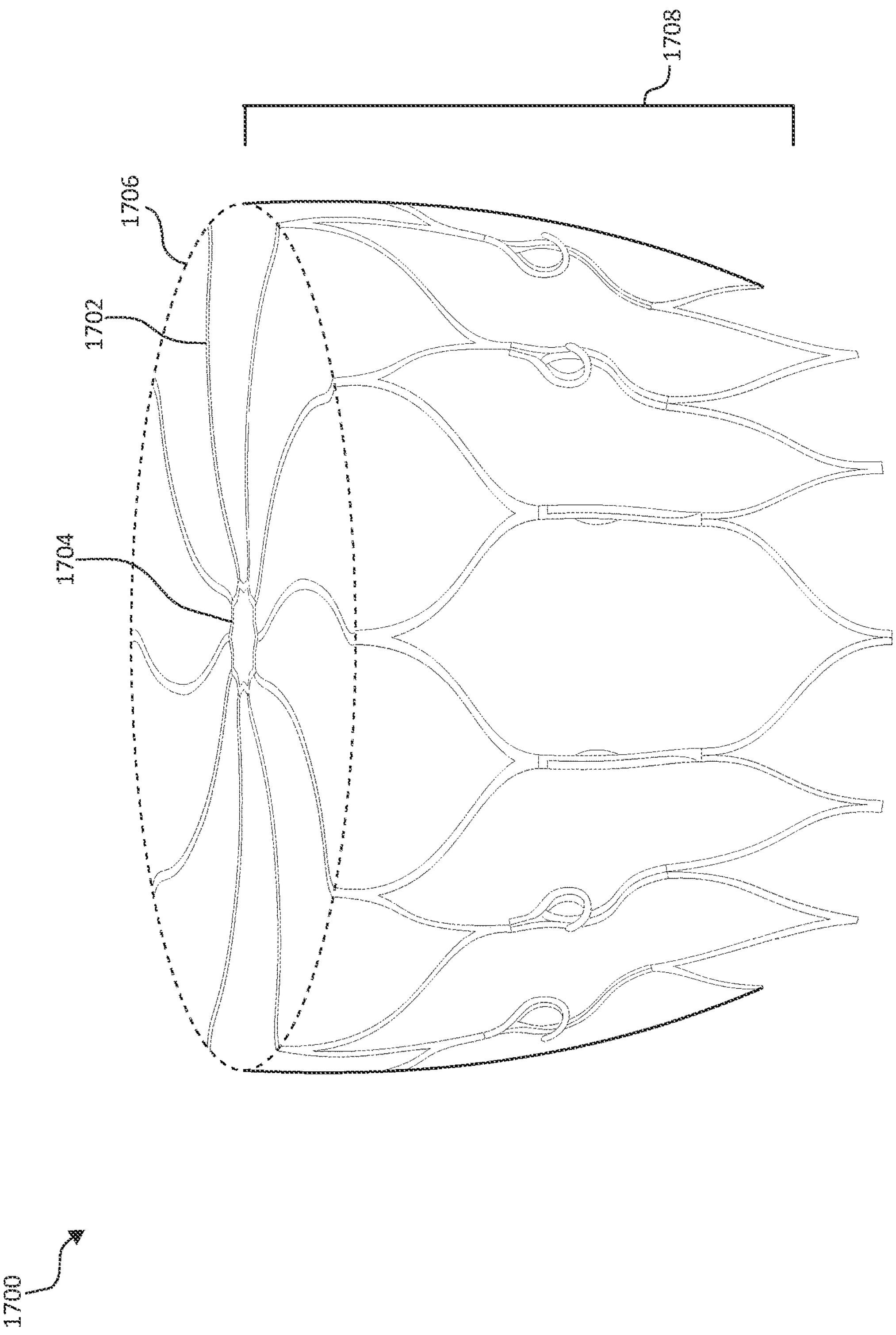
FIG. 17 is a perspective view of an alternate design of another example frame for an occlusive device, in accordance with various aspects of the present disclosure.

FIG. 17 is a perspective view of an alternate design of another example frame 1700 for an occlusive device, in accordance with various aspects of the present disclosure. The frame 1700 may include a body portion 1708 and a face portion 1706 that is used to block off the target location into which the body portion 1708 is implanted. As shown, the body portion 1708 may be a cylindrical shape formed by a plurality of struts or wires with approximately diamond shaped cells that include approximately different areas in each row.

The face portion 1706 may include a center frame portion 1704 and a plurality of elongate members 1702. As discussed above in detail with reference to FIGS. 2-5, the plurality of elongate members 1702 may enhance fatigue resistance of the frame 1700 by functioning as stress relief features that absorb displacement, flexure and/or torque, and the like, in response to a force being applied to the body portion 1708. Thus, the plurality of elongate members 1702 may be configured to configured to flex or bend substantially within plane, in which the plurality of elongate members 1702 and the center frame portion 1704 are arranged, to mitigate longitudinal movement of the face portion 1706 substantially outward from the plane in response to a force applied to one or more portions of the body portion 1708.

The illustrative components shown in FIG. 17 are not intended to suggest any limitation as to the scope of use or functionality of embodiments of the disclosed subject matter. Neither should the illustrative components be interpreted as having any dependency or requirement related to any single component or combination of components illustrated therein. In certain instances, for example, face portions 220, 300, 400, 502*a* or 502*b* may be incorporated in place of the face portion 1706.

Figure 18:
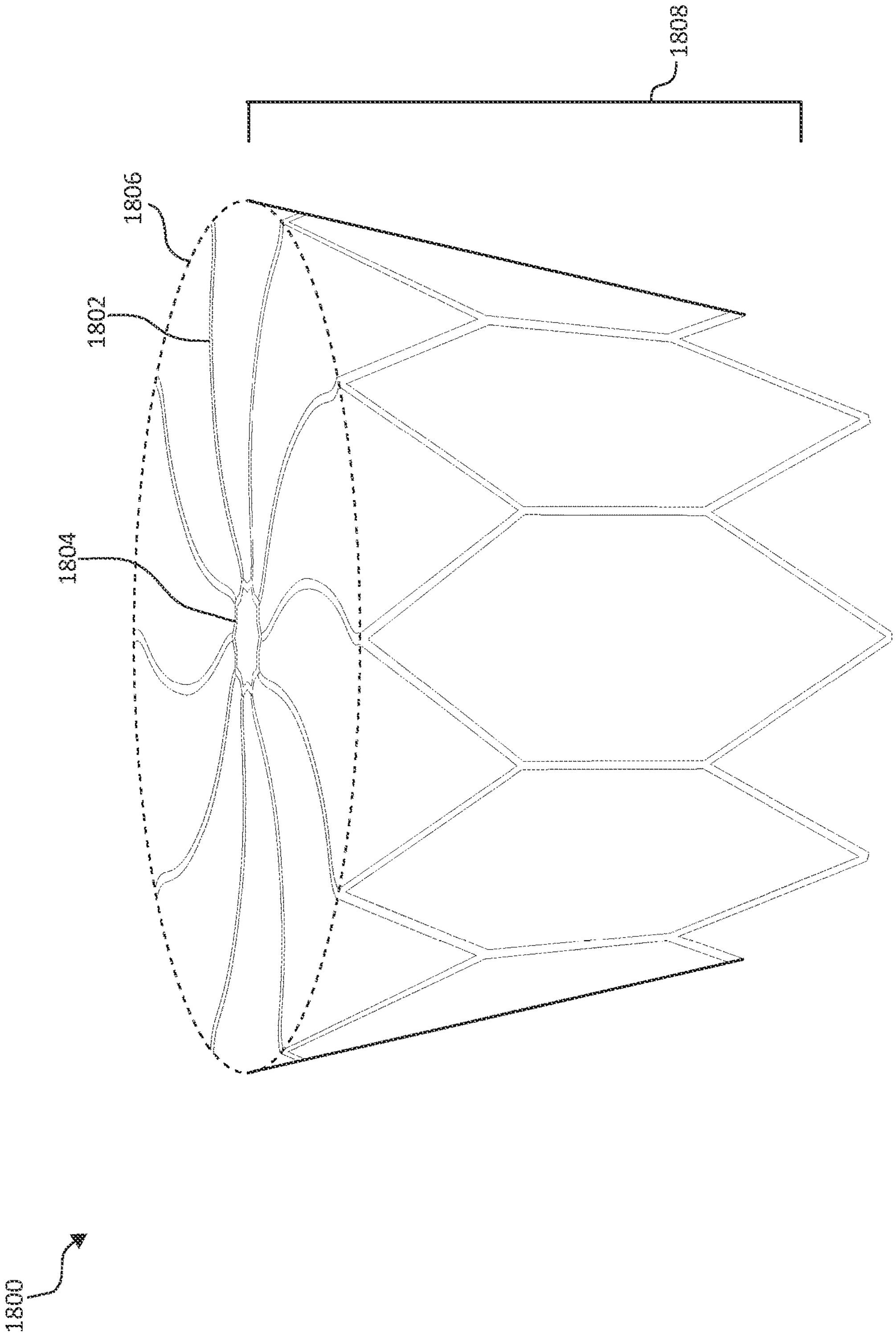
FIG. 18 is a perspective view of an alternate design of another example frame for an occlusive device, in accordance with various aspects of the present disclosure.

FIG. 18 is a perspective view of an alternate design of another example frame 1800 for an occlusive device, in accordance with various aspects of the present disclosure. The frame 1800 may include a body portion 1808 and a face portion 1806 that is used to block off the target location into which the body portion 1808 is implanted. As shown, the body portion 1808 may be formed by a plurality of struts or wires that form a diamond shape row.

The face portion 1806 may include a center frame portion 1804 and a plurality of elongate members 1802. As discussed above in detail with reference to FIGS. 2-5, the plurality of elongate members 1802 may enhance fatigue resistance of the frame 1800 by functioning as stress relief features that absorb displacement, flexure and/or torque, and the like, in response to a force being applied to the body portion 1808. Thus, the plurality of elongate members 1802 may be configured to configured to flex or bend substantially within plane, in which the plurality of elongate members 1802 and the center frame portion 1804 are arranged, to mitigate longitudinal movement of the face portion 1806 substantially outward from the plane in response to a force applied to one or more portions of the body portion 1808.

The illustrative components shown in FIG. 18 are not intended to suggest any limitation as to the scope of use or functionality of embodiments of the disclosed subject matter. Neither should the illustrative components be interpreted as having any dependency or requirement related to any single component or combination of components illustrated therein. In certain instances, for example, face portions 220, 300, 400, 502*a* or 502*b* may be incorporated in place of the face portion 1806.

In general, it can be observed that certain embodiments of the occlusive devices provided herein are more conformable (less stiff) than the commercially available occlusive devices. Such enhanced conformability can provide better sealing (more consistent contact between the occlusive device and surrounding tissue), improved fatigue resistance, less trauma to the patient, and more stable positioning, to provide some example benefits. It can also be said that the embodiments of the occlusive devices provided herein are not designed to “drive” tissue into conformance with the occlusive devices. Rather, the occlusive devices are generally intended to conform themselves to the native topography of the surrounding tissue.

It has been found that certain embodiments of the occlusive devices provided herein are more capable of being recaptured and reloaded into a delivery sheath without causing damage to the surrounding tissue. For example, in some embodiments the anchor members of the occlusive devices are more capable of deflection during recapture and reloading. Additionally, in certain embodiments, the anchor members allow the occlusion device to fully reload into the delivery system without damage to the occlusion device and delivery system. Consequently, embodiments of the occlusive devices provided herein may be removed from tissue essentially atraumatically.

While the anchors of the occlusive devices provided herein are capable of atraumatic deflection during recapture and reloading, the anchors provide stable in vivo positioning. Some geometric parameters of the anchors are significant in respect to migration resistance. Such factors include, the tip angle, number of anchors on an occlusive device, the tip length, and width and thickness of the elongate anchor member.

LAA closure effectiveness can be assessed by contrast injection and by color flow Doppler during transesophageal echocardiography (TEE). Contrast injection is used procedurally to primarily assess the occlusive device position in relation to the surrounding tissue, but can also be utilized to give an indication of LAA closure. Fluoroscopic measurements can be taken where contrast passes past the occluder to quantify the size of the leak, however the maximum diameter of the leak can be difficult to assess with this method. Color flow Doppler is the preferred modality to measure leaks past a LAA occluder. The TEE probe position is varied until the maximum leak is seen. The image is captured, and a measurement of the leak is taken on the TEE workstation. “Substantial occlusion” and “substantial closure” in the context of TEE means that there is no discernable flow through or around the occlusive device.

This application claims priority to Provisional Application No. 62/161,742, filed May 14, 2015, which is herein incorporated by reference in its entirety. More specifically, FIGS. 1-29 of Provisional Application No. 62/161,742 relate to example occlusive devices and aspects thereof, and are specifically incorporated herein for their teachings and related structural aspects.

As the terms are used herein with respect to ranges of measurements (such as those disclosed immediately above), “about” and “approximately” may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Several implantable occlusive device and frame embodiments have been described herein. It should be understood that one or more of the features described in the context of a particular device may be combined with one or more features of any other device or multiple devices described herein. That is, the features of the occlusive devices and frames described herein may be mixed and matched to provide hybrid occlusive device and device frame embodiments, and such hybrid occlusive device and device frame embodiments are within the scope of this disclosure. In some examples, one or more features described with respect to a particular device or frame may replace or be substituted for one or more features of another device or frame. In some examples, one or more features described with respect to a particular device or frame may be added to or included with another device or frame. Also, various combinations or sub-combinations of any of the features described herein may generally be used with any of the devices or frames described herein. It should be understood that the occlusive devices and occlusive device frames provided herein are scalable to a broad range of sizes so that the occlusive devices can be used in a variety of different anatomies, implant sites, and types of implementations.

Several characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shapes, sizes, and arrangements of parts including combinations within the principles described herein, to the full extent indicated by the broad, general meaning of the terms in which the appended claims are expressed. To the extent that these various modifications depart from the spirit and scope of the appended claims, they are intended to be encompassed therein. All references, publications, and patents referred to herein, including the figures and drawings included therewith, are incorporated by reference in their entirety.

What is claimed is:

1. A device for placement in vessels, appendages, and openings in a body, the device comprising:
- a unitary self-expanding frame having a proximal end, a distal end, and a longitudinal axis, the unitary self-expanding frame including:
  - a face portion having a pre-loaded flat configuration and (i) a center frame portion arranged at the proximal end and (ii) a plurality of elongate members extending from the center frame portion, and
  - a body portion; and
- a membrane attached to the unitary self-expanding frame;
  - wherein the plurality of elongate members are configured to bend or flex substantially in a plane orthogonal to the longitudinal axis and mitigate longitudinal movement of the face portion in response to a compressive force applied to the body portion of the unitary self-expanding frame.

2. The device of claim 1, wherein the center frame portion is a hole having an inner and outer circumference and the plurality of elongate members radiate outward from the outer circumference of the center frame portion.

3. The device of claim 2, wherein the center frame portion further includes a plurality of arcs arranged around the inner circumference of the center frame portion.

4. The device of claim 1, wherein a thickness, relative to the longitudinal axis, of the plurality of elongate members is approximately equal to a thickness, relative to the longitudinal axis, of the center frame portion.

5. The device of claim 1, wherein the center frame portion and the plurality of elongate members are arranged within a first plane substantially orthogonal to the longitudinal axis.

6. The device of claim 1, wherein the membrane comprises an occlusive material configured to at least partially inhibit passage of fluid and passage of thrombus therethrough.

7. The device of claim 1, wherein the unitary self-expanding frame further comprises transition portions arranged between the plurality of elongate members and the body portion, and wherein the transition portions include a curvature to transition the plurality of elongate members toward the body portion.

8. The device of claim 1, wherein the plurality of elongate members include a first curved section, a second curved section, and a third curved section, a first inflection point between the first curved section and the second curved section, and a second inflection point between the second curved section and the third curved section.

9. The device of claim 8, wherein the first curved section and the third curved section comprise a curvature in a first direction, the second curved section comprises a curvature in a second direction, and the first direction is opposite of the second direction.

10. The device of claim 1, wherein the body portion includes a first tapered section and a second tapered section, the first tapered section decreases in circumference at a first rate, the second tapered section decreases in circumference at a second rate, and the first rate is less than the second rate.

11. The device of claim 1, wherein the body portion further comprises a plurality of anchors, and each of the plurality of anchors includes an anchoring portion and an arm.

12. The device of claim 11, wherein
- the plurality of anchors includes a first group of anchors and a second group of anchors, the arm of the first group of anchors includes a first length, the arm of the second group of anchors includes a second length, and the second length is greater than the first length, and
- the anchoring portion of the first group of anchors is arranged at a first height, relative to the distal end, the anchoring portion of the second group of anchors is arranged at a second height, relative to the distal end, and the first height is greater than the second height.

13. A device for placement in vessels, appendages, and openings in a body having an elongated configuration and a deployed configuration, the device comprising:
- a nitinol cut-tube frame having a proximal end and a distal end, the nitinol cut-tube frame including:
  - a face portion having
    - a center frame portion arranged at the proximal end and including a plurality of arcs arranged around a circumference of the center frame portion, and
    - a plurality of elongate members extending from the center frame portion, and
  - a body portion; and
- a membrane attached to the nitinol cut-tube frame;
  - wherein the center frame portion and the plurality of elongate members form a substantially uniform surface, wherein the plurality of elongate members are configured to bend or flex in a plane that is substantially orthogonal to a longitudinal axis of the nitinol cut-tube frame to mitigate longitudinal movement of the face portion in response to a compressive force applied to the body portion of the nitinol cut-tube frame, and the center frame portion is configured to provide an attachment point for a delivery system for the device.

14. The device of claim 13, wherein the center frame portion includes a thickness that is approximately equal to a thickness of the plurality of elongate members.

15. The device of claim 13, wherein the face portion comprises a surface without protrusions external to the face portion.

16. The device of claim 13, wherein the body portion further comprises a plurality of anchors, and each of the plurality of anchors includes an anchoring portion and an arm.

17. The device of claim 13, wherein the plurality of elongate members include a first curved section, a second curved section, and a third curved section, a first inflection point between the first curved section and the second curved section, and a second inflection point between the second curved section and the third curved section.

18. The device of claim 13, wherein the plurality of arcs arranged around a circumference of the center frame portion configured to distribute strain about the center frame portion in transitioning between the elongated configuration and the deployed configuration.

19. A method of reducing thrombus formation in treatment of left atrial appendage of a patient, the method comprising:
- positioning a transcatheter assembly through an ostium of the left atrial appendage;

deploying a device from the transcatheter assembly, the device comprising: a unitary self-expanding frame having a proximal end, a distal end, and a longitudinal axis, the unitary self-expanding frame including a face portion having a center frame portion arranged at the proximal end and a plurality of elongate members extending from the center frame portion, a body portion arranged substantially orthogonal to the face portion, and a membrane attached to the unitary self-expanding frame, wherein the face portion and the membrane define an occlusive face of the device; and absorbing one or more forces from the left atrial appendage with thereby flexing the plurality of elongate members in a plane orthogonal to the longitudinal axis to mitigate longitudinal movement of the face portion in response thereto.

20. The method of claim 19, wherein absorbing one or more forces from the left atrial appendage comprises mitigating thrombosis formation by maintaining a substantially planar occlusive face.

* * * * *